(12) United States Patent
Jin

(10) Patent No.: US 9,440,977 B2
(45) Date of Patent: Sep. 13, 2016

(54) COMPOSITIONS, USES AND METHODS FOR THEIR PREPARATION

(71) Applicant: Bohan Jin, San Diego, CA (US)

(72) Inventor: Bohan Jin, San Diego, CA (US)

( * ) Notice: Subject to any disclaimer, the term of this patent is extended or adjusted under 35 U.S.C. 154(b) by 0 days.

(21) Appl. No.: 15/024,681

(22) PCT Filed: Oct. 14, 2014

(86) PCT No.: PCT/US2014/060468
§ 371 (c)(1),
(2) Date: Mar. 24, 2016

(87) PCT Pub. No.: WO2015/057695
PCT Pub. Date: Apr. 23, 2015

(65) Prior Publication Data
US 2016/0229855 A1    Aug. 11, 2016

Related U.S. Application Data

(60) Provisional application No. 61/891,252, filed on Oct. 15, 2013.

(51) Int. Cl.
*C07D 471/16*    (2006.01)

(52) U.S. Cl.
CPC .................................. *C07D 471/16* (2013.01)

(58) Field of Classification Search
None
See application file for complete search history.

(56) References Cited

FOREIGN PATENT DOCUMENTS

| WO | WO-2005/044194 A2 | 5/2005 |
| WO | WO-2011/025889 A1 | 3/2011 |
| WO | WO-2012/135631 A1 | 10/2012 |

OTHER PUBLICATIONS

International Search Report and Written Opinion issued in International Application No. PCT/US2014/060468, dated Feb. 12, 2015.

*Primary Examiner* — Brian J Davis
(74) *Attorney, Agent, or Firm* — Venable LLP; Toni-Junell Herbert; Aubrey A. Haddach

(57) ABSTRACT

The present invention relates to novel compounds and pharmaceutical compositions thereof which may be useful in the treatment and/or prevention of various conditions. The present invention also provides methods of preparing such compounds and compositions, and methods of using the same.

7 Claims, No Drawings

COMPOSITIONS, USES AND METHODS FOR THEIR PREPARATION

CROSS-REFERENCE TO RELATED APPLICATIONS

This application claims priority to PCT Application No. PCT/US2014/060468, filed Oct. 14, 2015, which claimed priority to U.S. Provisional Patent Application No. 61/891,252, filed Oct. 15, 2013, each of which is hereby incorporated by reference in their entirety.

FIELD OF THE INVENTION

The present invention relates to novel compounds and pharmaceutical compositions thereof which may be useful in the treatment and/or prevention of various conditions. The present invention also provides methods of preparing such compounds and compositions, and methods of using the same.

BACKGROUND OF THE INVENTION

A need exists for new drug therapies having greater receptor selectivity for the treatment of subjects suffering from or susceptible to the diseases, disorders or conditions described herein. In addition, a need still exists for new drugs having one or more improved properties either alone or when combined with other agents (such as safety profile, efficacy, or physical properties) relative to those therapies currently available.

SUMMARY OF THE INVENTION

In various embodiments, provided herein are compounds of Formula I, Formula II, or Formula III, or pharmaceutically acceptable salt, solvate, analog, prodrug, isomer or tautomer thereof:

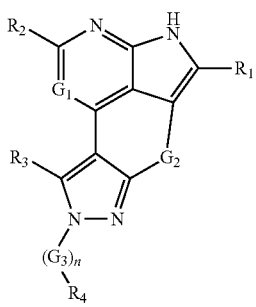

I

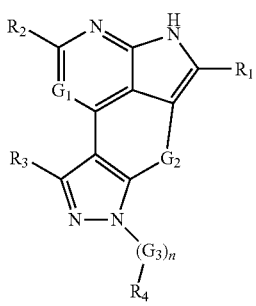

II

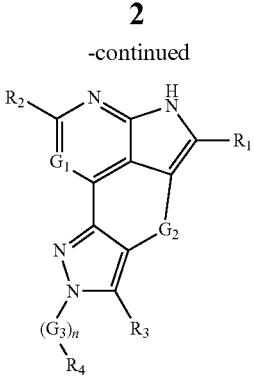

III wherein $G_1$ is N or $CR_5$; $G_2$ is —$NR_8$—, C=O, —C(O)—$NR_8$—, —$NR_8C(O)$—, or —$CR_6R_7$; $G_3$ is a bond, hydrogen, —C(O)—, —C(O)—NH—, —C(O)N—$R_8$, —$SO_2$—, —S(O)—, optionally substituted $C_{1-6}$ alkyl, optionally substituted $C_{3-8}$ cycloalkyl, optionally substituted $C_{3-6}$ heterocycloalkyl, optionally substituted $C_{4-14}$ aryl, or optionally substituted $C_{1-10}$ heteroaryl; n is 0, 1, 2, 3, or 4; $R_1$ is hydrogen, optionally substituted $C_{1-4}$ alkyl, optionally substituted $C_{3-8}$ cycloalkyl, optionally substituted $C_{3-8}$ heterocycloalkyl, or halogen; $R_2$ is hydrogen, optionally substituted $C_{1-4}$ alkyl, optionally substituted $C_{1-4}$ alkoxy, optionally substituted $C_{3-8}$cycloalkyl, optionally substituted $C_{3-8}$ heterocycloalkyl, halogen, hydroxy, or amino; $R_3$ and $R_5$ are each independently hydrogen, optionally substituted $C_{1-6}$ alkyl, optionally substituted $C_{1-4}$ alkoxy, $C_{1-9}$ amide, $C_{1-5}$ oxycarbonyl, cyano, optionally substituted $C_{3-8}$ cycloalkyl, optionally substituted $C_{4-14}$ aryl, optionally substituted $C_{1-10}$ heteroaryl, or halogen; $R_8$ is -$(G_3)$n-$R_4$, optionally substituted $C_{1-4}$ alkyl, optionally substituted $C_{3-8}$ cycloalkyl, optionally substituted $C_{3-6}$ heterocycloalkyl, optionally substituted $C_{4-14}$ aryl, or optionally substituted $C_{1-10}$ heteroaryl; $R_4$ is optionally substituted $C_{1-4}$ alkyl, optionally substituted $C_{3-8}$ cycloalkyl, optionally substituted $C_{3-6}$ heterocycloalkyl, optionally substituted $C_{4-14}$ aryl, or optionally substituted $C_{1-10}$ heteroaryl; wherein $R_4$ and $R_8$ can be joined to form a ring; and $R_6$ and $R_7$ are each independently —$OR_3$, —$NHR_3$, —$NR_3R_3$, hydrogen, halo, optionally substituted $C_{1-4}$ alkyl, optionally substituted $C_{3-8}$ cycloalkyl, or optionally substituted $C_{3-8}$ heterocycloalkyl; wherein $R_6$ and $R_7$ can be joined to form a ring.

In some specific embodiments, the compounds have the following structures, or pharmaceutically acceptable salt, solvate, analog, prodrug, isomer or tautomer thereof:

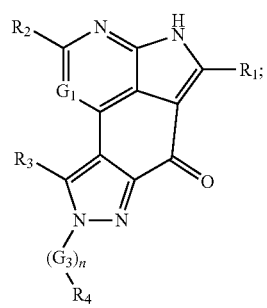

Ia

-continued
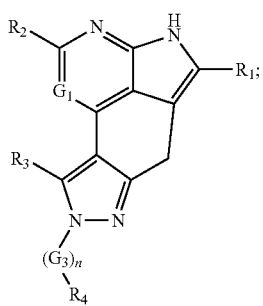
Ib
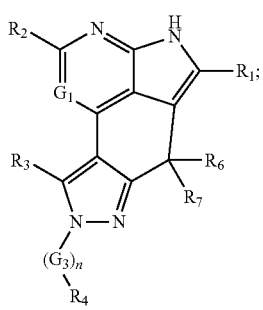
Ic
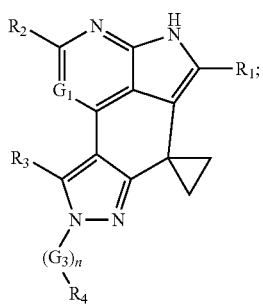
Id
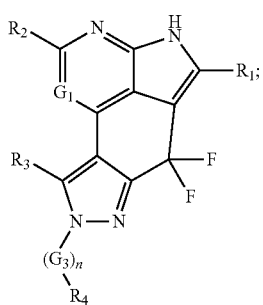
Ie
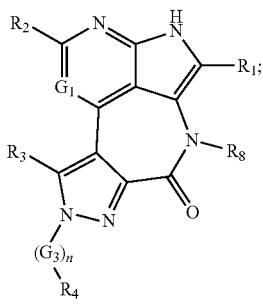
If
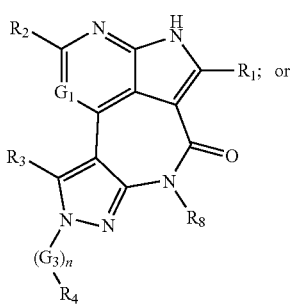
Ig
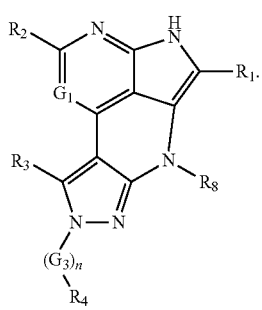
Ih
In some specific embodiments, the compounds have the following structures, or pharmaceutically acceptable salt, solvate, analog, prodrug, isomer or tautomer thereof:
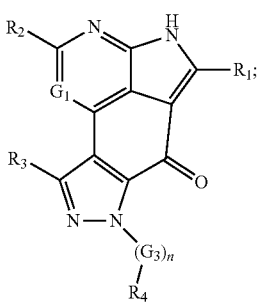
IIa
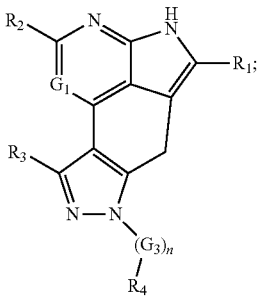
IIb
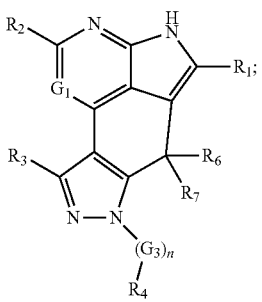
IIc -continued
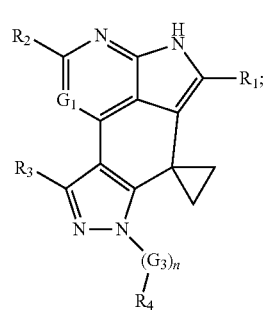
IId
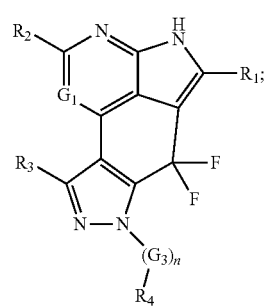
IIe
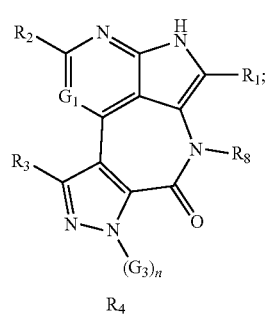
IIf
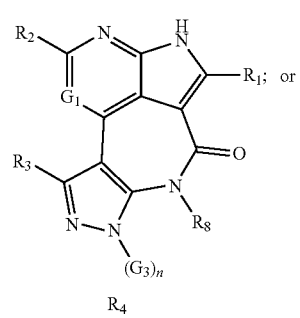
IIg
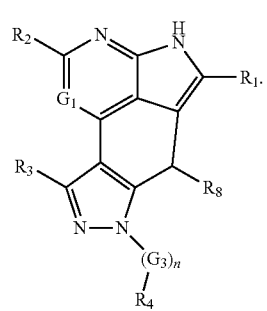
IIh
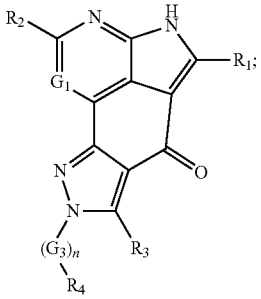
IIIa
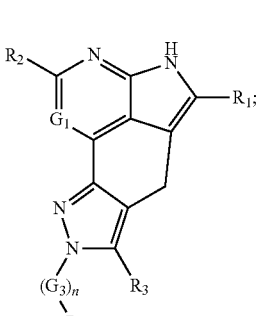
IIIb
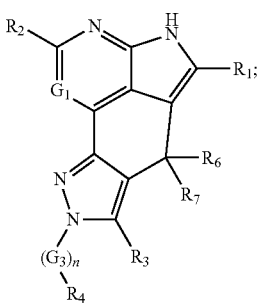
IIIc
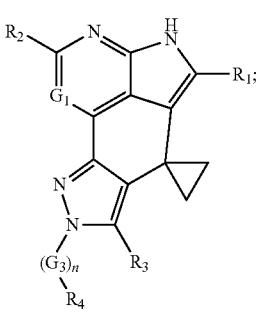
IIId
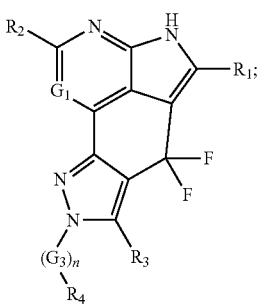
IIIe
In some specific embodiments, the compounds have the following structures, or pharmaceutically acceptable salt, solvate, analog, prodrug, isomer or tautomer thereof:

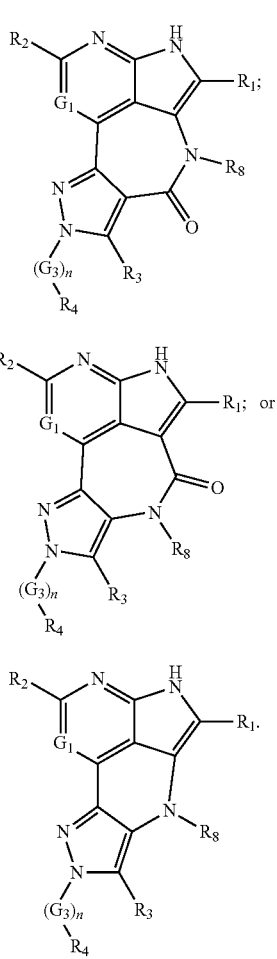

In various embodiments, provided herein are compounds of Formula IV or Formula V, or pharmaceutically acceptable salt, solvate, analog, prodrug, isomer or tautomer thereof:

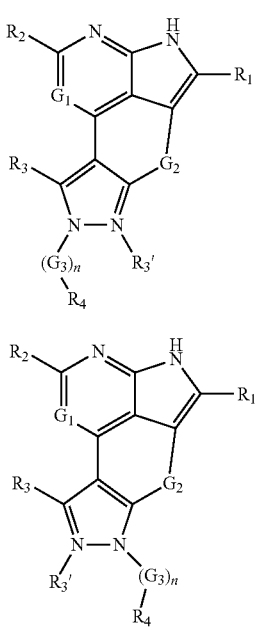

wherein $G_1$ is N or $CR_5$; $G_2$ is $-NR_8-$, C=O, $-C(O)-NR_8-$, $-NR_8C(O)-$, or $-CR_6R_7$; wherein $R_6$ and $R_7$ are each independently $-OR_3$, $-NHR_3$, or $-NR_3R_{3'}$, and can be joined to form a ring; $G_3$ is a bond, hydrogen, $-C(O)-$, $-C(O)-NH-$, $-C(O)N-R_8$, $-SO_2-$, $-S(O)-$, optionally substituted $C_{1-6}$ alkyl, optionally substituted $C_{3-8}$ cycloalkyl, optionally substituted $C_{3-6}$ heterocycloalkyl, optionally substituted $C_{4-14}$ aryl, or optionally substituted $C_{1-10}$ heteroaryl; n is 0, 1, 2, 3, or 4; $R_1$ is hydrogen, optionally substituted $C_{1-4}$ alkyl, optionally substituted $C_{3-8}$ cycloalkyl, optionally substituted $C_{3-8}$ heterocycloalkyl, or halogen; $R_2$ is hydrogen, optionally substituted $C_{1-4}$ alkyl, optionally substituted $C_{1-4}$ alkoxy, optionally substituted $C_{3-8}$ cycloalkyl, optionally substituted $C_{3-8}$ heterocycloalkyl, halogen, hydroxy, or amino; $R_3$ and $R_{3'}$ are each independently hydrogen, optionally substituted $C_{1-6}$ alkyl, optionally substituted $C_{1-4}$ alkoxy, $C_{1-9}$ amide, $C_{1-5}$ oxycarbonyl, cyano, optionally substituted $C_{3-8}$ cycloalkyl, optionally substituted $C_{4-14}$ aryl, optionally substituted $C_{1-10}$ heteroaryl, or halogen; $R_5$ is hydrogen, optionally substituted $C_{1-6}$ alkyl, optionally substituted $C_{1-4}$ alkoxy, $C_{1-9}$ amide, $C_{1-5}$ oxycarbonyl, cyano, optionally substituted $C_{3-8}$ cycloalkyl, optionally substituted $C_{4-14}$ aryl, optionally substituted $C_{1-10}$ heteroaryl, or halogen; $R_8$ is $-(G_3)n-R_4$, optionally substituted $C_{1-4}$ alkyl, optionally substituted $C_{3-8}$ cycloalkyl, optionally substituted $C_{3-6}$ heterocycloalkyl, optionally substituted $C_{4-14}$ aryl, or optionally substituted $C_{1-10}$ heteroaryl; $R_4$ is optionally substituted $C_{1-4}$ alkyl, optionally substituted $C_{3-8}$ cycloalkyl, optionally substituted $C_{3-6}$ heterocycloalkyl, optionally substituted $C_{4-14}$ aryl, or optionally substituted $C_{1-10}$ heteroaryl; wherein $R_4$ and $R_8$ can be joined to form a ring; and $R_6$ and $R_7$ are each independently $-OR_3$, $-NHR_3$, or $-NR_3R_{3'}$, hydrogen, halo, optionally substituted $C_{1-4}$ alkyl, optionally substituted $C_{3-8}$ cycloalkyl, or optionally substituted $C_{3-8}$ heterocycloalkyl; wherein $R_6$ and $R_7$ can be joined to form a ring.

In various embodiments, provided herein are compounds of Formula VI, Formula VII or Formula VIII, or pharmaceutically acceptable salt, solvate, analog, prodrug, isomer or tautomer thereof:

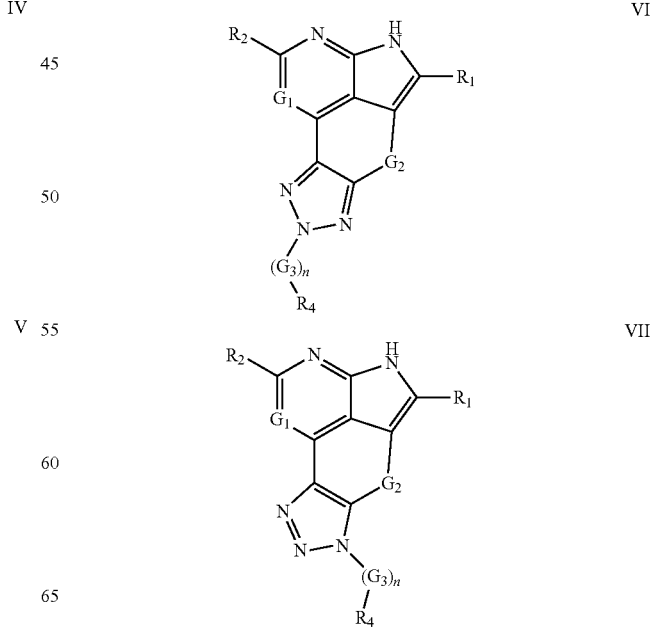

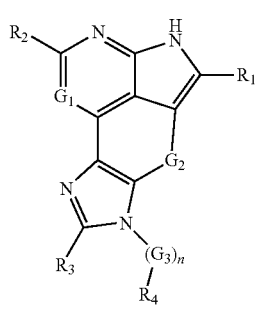

VIII wherein $G_1$ is N or $CR_5$; $G_2$ is —$NR_8$—, C=O, —C(O)—$NR_8$—, —$NR_8$C(O)—, or —$CR_6R_7$; wherein $R_6$ and $R_7$ are each independently —$OR_3$, —$NHR_3$, or —$NR_3R_3$, and can be joined to form a ring; $G_3$ is a bond, hydrogen, —C(O)—, —C(O)—NH—, —C(O)N—$R_8$, —$SO_2$—, —S(O)—, optionally substituted $C_{1-6}$ alkyl, optionally substituted $C_{3-8}$ cycloalkyl, optionally substituted $C_{3-6}$ heterocycloalkyl, optionally substituted $C_{4-14}$ aryl, or optionally substituted $C_{1-10}$ heteroaryl; n is 0, 1, 2, 3, or 4; $R_1$ is hydrogen, optionally substituted $C_{1-4}$ alkyl, optionally substituted $C_{3-8}$ cycloalkyl, optionally substituted $C_{3-8}$ heterocycloalkyl, or halogen; $R_2$ is hydrogen, optionally substituted $C_{1-4}$ alkyl, optionally substituted $C_{1-4}$ alkoxy, optionally substituted $C_{3-8}$ cycloalkyl, optionally substituted $C_{3-8}$ heterocycloalkyl, halogen, hydroxy, or amino; $R_5$ is hydrogen, optionally substituted $C_{1-6}$ alkyl, optionally substituted $C_{1-4}$ alkoxy, $C_{1-9}$ amide, $C_{1-5}$ oxycarbonyl, cyano, optionally substituted $C_{3-8}$ cycloalkyl, optionally substituted $C_{4-14}$ aryl, optionally substituted $C_{1-10}$ heteroaryl, or halogen; $R_8$ is -($G_3$)n-$R_4$, optionally substituted $C_{1-4}$ alkyl, optionally substituted $C_{3-8}$ cycloalkyl, optionally substituted $C_{3-6}$ heterocycloalkyl, optionally substituted $C_{4-14}$ aryl, or optionally substituted $C_{1-10}$ heteroaryl; $R_4$ is optionally substituted $C_{1-4}$ alkyl, optionally substituted $C_{3-8}$ cycloalkyl, optionally substituted $C_{3-6}$ heterocycloalkyl, optionally substituted $C_{4-14}$ aryl, or optionally substituted $C_{1-10}$ heteroaryl; wherein $R_4$ and $R_8$ can be joined to form a ring; and $R_6$ and $R_7$ are each independently —$OR_3$, —$NHR_3$, —$NR_3R_3$, hydrogen, halo, optionally substituted $C_{1-4}$ alkyl, optionally substituted $C_{3-8}$ cycloalkyl, or optionally substituted $C_{3-8}$ heterocycloalkyl; wherein $R_6$ and $R_7$ can be joined to form a ring.

In some specific embodiments, the compounds have the following structures, or pharmaceutically acceptable salt, solvate, analog, prodrug, isomer or tautomer thereof:

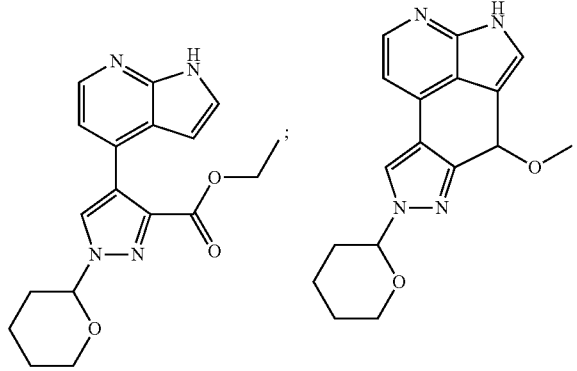

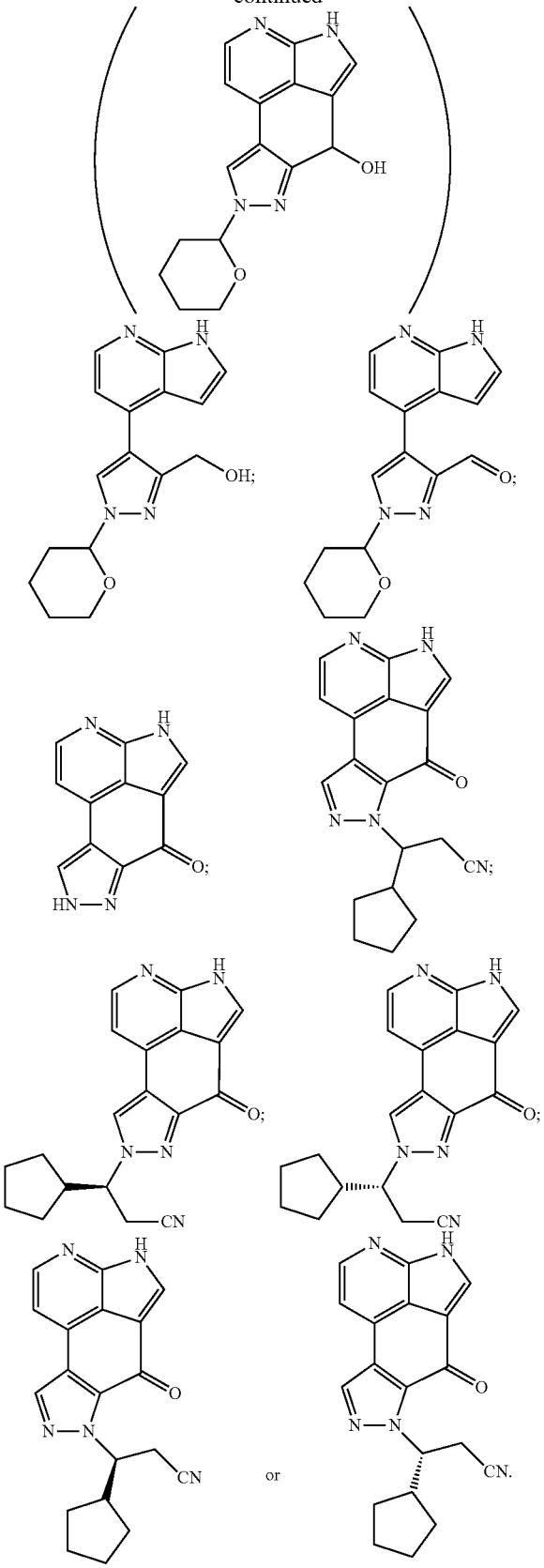

Also provided herein are pharmaceutical compositions comprising a therapeutically effective amount of a compound of Formula I, Formula Ia, Formula Ib, Formula Ic, Formula Id, Formula Ie, Formula If, Formula Ig, Formula Ih, Formula II, Formula IIa, Formula IIb, Formula IIc, Formula IId, Formula IIe, Formula IIf, Formula IIg, Formula IIh, Formula III, Formula IIIa, Formula IIIb, Formula IIIc, Formula IIId, Formula IIIe, Formula IIIf, Formula IIIg, Formula IIIh, Formula IV, Formula V, Formula VI, Formula VII, Formula VIII or a pharmaceutically acceptable salt, solvate, analog, prodrug, isomer or tautomer thereof, and at least one pharmaceutically acceptable inactive ingredient selected from pharmaceutically acceptable diluents, pharmaceutically acceptable excipients, and pharmaceutically acceptable carriers.

The details of additional embodiments are set forth in the accompanying drawings and the description below. Other features, objects, and advantages of the embodiments will be apparent from the drawings and detailed description, and from the claims.

DETAILED DESCRIPTION OF THE INVENTION

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein represent a presently preferred embodiment of the invention and are therefore representative of the subject matter which is broadly contemplated by the present invention. It is further understood that the scope of the present invention fully encompasses other embodiments that may become obvious to those skilled in the art and that the scope of the present invention is accordingly not limited.

The compounds of the invention can be prepared by a variety of procedures, some of which are described below. All substituents, unless otherwise indicated, are as previously defined. The products of each step can be recovered by conventional methods including extraction, evaporation, precipitation, chromatography, filtration, trituration, crystallization, and the like. The procedures may require protection of certain groups, for example hydroxy, amino, or carboxy groups to minimize unwanted reactions. The selection, use, and removal of protecting groups are well known and appreciated as standard practice, for example T. W. Greene and P. G. M. Wuts in Protective Groups in Organic Chemistry (John Wiley and Sons, 1991).

Certain Exemplary Terminology

Unless defined otherwise, all technical and scientific terms used herein have the same meaning as is commonly understood by one of skill in the art to which the claimed subject matter belongs. In the event that there is a plurality of definitions for terms herein, those in this section prevail. Where reference is made to a URL or other such identifier or address, it is understood that such identifiers can change and particular information on the internet can come and go, but equivalent information can be found by searching the internet. Reference thereto evidences the availability and public dissemination of such information.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless otherwise stated. Furthermore, use of the term "including" as well as other forms, such as "include", "includes," and "included," is not limiting.

The section headings used herein are for organizational purposes only and are not to be construed as limiting the subject matter described. All documents, or portions of documents, cited in the application including, but not limited to, patents, patent applications, articles, books, manuals, and treatises are hereby expressly incorporated by reference in their entirety for any purpose.

Definition of standard chemistry terms may be found in reference works, including Carey and Sundberg "ADVANCED ORGANIC CHEMISTRY 4.sup.TH ED." Vols. A (2000) and B (2001), Plenum Press, New York. Unless otherwise indicated, conventional methods of mass spectroscopy, NMR, HPLC, protein chemistry, biochemistry, recombinant DNA techniques and pharmacology, within the skill of the art are employed. Unless specific definitions are provided, the nomenclature employed in connection with, and the laboratory procedures and techniques of, analytical chemistry, synthetic organic chemistry, and medicinal and pharmaceutical chemistry described herein are those known in the art. Standard techniques can be used for chemical syntheses, chemical analyses, pharmaceutical preparation, formulation, and delivery, and treatment of patients. Reactions and purification techniques can be performed e.g., using kits of manufacturer's specifications or as commonly accomplished in the art or as described herein. The foregoing techniques and procedures can be generally performed of conventional methods well known in the art and as described in various general and more specific references that are cited and discussed throughout the present specification.

It is to be understood that the methods and compositions described herein are not limited to the particular methodology, protocols, cell lines, constructs, and reagents described herein and as such may vary. It is also to be understood that the terminology used herein is for the purpose of describing particular embodiments only, and is not intended to limit the scope of the methods and compositions described herein.

As used herein, $C_1$-$C_x$ includes $C_1$-$C_2$, $C_1$-$C_3$ . . . $C_1$-$C_x$.

An "alkyl" group refers to an aliphatic hydrocarbon group. The alkyl moiety may be a "saturated alkyl" group, which means that it does not contain any alkene or alkyne moieties. The alkyl moiety may also be an "unsaturated alkyl" moiety, which means that it contains at least one alkene or alkyne moiety. An "alkene" moiety refers to a group consisting of at least two carbon atoms and at least one carbon-carbon double bond, and an "alkyne" moiety refers to a group consisting of at least two carbon atoms and at least one carbon-carbon triple bond. The alkyl moiety, whether saturated or unsaturated, may be branched, straight chain, or cyclic. Depending on the structure, an alkyl group can be a monoradical or a diradical (i.e., an alkylene group).

The "alkyl" moiety may have 1 to 10 carbon atoms (whenever it appears herein, a numerical range such as "1 to 10" refers to each integer in the given range; e.g., "1 to 10 carbon atoms" means that the alkyl group may consist of 1 carbon atom, 2 carbon atoms, 3 carbon atoms, etc., up to and including 10 carbon atoms, although the present definition also covers the occurrence of the term "alkyl" where no numerical range is designated). The alkyl group could also be a "lower alkyl" having 1 to 6 carbon atoms.

The alkyl group of the compounds described herein may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, ethenyl, propenyl, butenyl, cyclopropyl, cyclobutyl, cyclopentyl, cyclohexyl, and the like.

An "alkoxy" group refers to a (alkyl)O— group, where alkyl is as defined herein. A "lower alkoxy" has 1 to 6 carbon atoms.

The term "alkenyl" refers to a type of alkyl group in which the first two atoms of the alkyl group form a double bond that is not part of an aromatic group. That is, an alkenyl group begins with the atoms —C(R)=CR$_2$, wherein R refers to the remaining portions of the alkenyl group, which may be the same or different. Non-limiting examples of an alkenyl group include —CH=CH$_2$, —C(CH$_3$)=CH$_2$, —CH=CHCH$_3$ and —C(CH$_3$)=CHCH$_3$. The alkenyl moiety may be branched, straight chain, or cyclic (in which case, it would also be known as a "cycloalkenyl" group). Depending on the structure, an alkenyl group can be a monoradical or a diradical (i.e., an alkenylene group). A "lower alkenyl" has 2 to 6 carbon atoms in the chain.

The term "alkylamine" refers to the —N(alkyl)$_x$H$_y$, group, where alkyl is as defined herein and x and y are selected from the group x=1, y=1 and x=2, y=0. When x=2, the alkyl groups taken together with the nitrogen atom to which they are attached can optionally form a heterocyclic ring system.

An "amide" is a chemical moiety with formula —C(=O)NHR or —NHC(=O)R, where R is selected from the group consisting of alkyl, cycloalkyl, aryl, heteroaryl (bonded through a ring carbon) and heteroalicyclic (bonded through a ring carbon). An amide may be an amino acid or a peptide molecule attached to a compound described herein, such as, for example, a compound of Formula (I), thereby forming a prodrug. Any amine or carboxyl side chain on the compounds described herein can be amidified. The procedures and specific groups to make such amides are known to those of skill in the art and can readily be found in reference sources such as Greene and Wuts, Protective Groups in Organic Synthesis, 3.sup.rd Ed., John Wiley & Sons, New York, N.Y., 1999, which is incorporated herein by reference in its entirety.

The term "ester" refers to a chemical moiety with formula —COOR, where R is selected from the group consisting of alkyl, cycloalkyl, aryl, heteroaryl (bonded through a ring carbon) and heteroalicyclic (bonded through a ring carbon). Any hydroxy, or carboxyl side chain on the compounds described herein can be esterified. The procedures and specific groups to make such esters are known to those of skill in the art and can readily be found in reference sources such as Greene and Wuts, Protective Groups in Organic Synthesis, 3.sup.rd Ed., John Wiley & Sons, New York, N.Y., 1999, which is incorporated herein by reference in its entirety.

As used herein, the term "ring" refers to any covalently closed structure. Rings include, for example, carbocycles (e.g., aryls and cycloalkyls), heterocycles (e.g., heteroaryls and non-aromatic heterocycles), aromatics (e.g. aryls and heteroaryls), and non-aromatics (e.g., cycloalkyls and non-aromatic heterocycles). Rings can be optionally substituted. Rings can be monocyclic or polycyclic.

As used herein, the term "ring system" refers to one, or more than one ring.

The term "membered ring" can embrace any cyclic structure. The term "membered" is meant to denote the number of skeletal atoms that constitute the ring. Thus, for example, cyclohexyl, pyridine, pyran and thiopyran are 6-membered rings and cyclopentyl, pyrrole, furan, and thiophene are 5-membered rings.

The term "fused" refers to structures in which two or more rings share one or more bonds.

The term "carbocyclic" or "carbocycle" refers to a ring wherein each of the atoms forming the ring is a carbon atom. Carbocycle includes aryl and cycloalkyl. The term thus distinguishes carbocycle from heterocycle ("heterocyclic") in which the ring backbone contains at least one atom which is different from carbon (i.e a heteroatom). Heterocycle includes heteroaryl and heterocycloalkyl. Carbocycles and heterocycles can be optionally substituted.

As used herein, the term "aryl" refers to an aromatic ring wherein each of the atoms forming the ring is a carbon atom. Aryl rings can be formed by five, six, seven, eight, nine, or more than nine carbon atoms. Aryl groups can be optionally substituted. Examples of aryl groups include, but are not limited to phenyl, naphthalenyl, phenanthrenyl, anthracenyl, fluorenyl, and indenyl. Depending on the structure, an aryl group can be a monoradical or a diradical (i.e., an arylene group).

The term "cycloalkyl" refers to a monocyclic or polycyclic non-aromatic radical, wherein each of the atoms forming the ring (i.e. skeletal atoms) is a carbon atom. Cycloalkyls may be saturated, or partially unsaturated. Cycloalkyl groups include groups having from 3 to 10 ring atoms. Depending on the structure, a cycloalkyl group can be a monoradical or a diradical (e.g., a cycloalkylene group). Monocyclic cycloalkyls include, but are not limited to, cyclopropyl, cyclobutyl, cyclopentyl, cyclohexyl, cycloheptyl, and cyclooctyl. A "lower cycloalkyl" has 3 to 8 ring carbon atoms.

A "cycloalkylalkyl" refers to an alkyl, as defined herein, substituted with a cycloalkyl, as defined herein. Cycloalkylalkyls include, but are not limited to, cyclopropylmethyl, cyclobutylmethyl, cyclopentylmethyl, cyclohexylmethyl, cycloheptylmethyl, and cyclooctylmethyl.

A "cycloalkoxy" refers to —O-(cycloalkyl), where cycloalkyl is as defined herein. A lower cycloalkoxy has 3 to 8 carbons.

The terms "heteroaryl" or, alternatively, "heteroaromatic" refers to an aryl group that includes one or more ring heteroatoms selected from nitrogen, oxygen and sulfur. An N-containing "heteroaromatic" or "heteroaryl" moiety refers to an aromatic group in which at least one of the skeletal atoms of the ring is a nitrogen atom. The polycyclic heteroaryl group may be fused or non-fused. Depending on the structure, a heteroaryl group can be a monoradical or a diradical (i.e., a heteroarylene group).

The term "heterocycle" refers to heteroaromatic and heteroalicyclic groups containing one to four heteroatoms each selected from O, S and N, wherein each heterocyclic group has from 4 to 10 atoms in its ring system, and with the proviso that the ring of said group does not contain two adjacent O or S atoms. Non-aromatic heterocyclic groups include groups having only 3 atoms in their ring system, but aromatic heterocyclic groups must have at least 5 atoms in their ring system. The heterocyclic groups include benzo-fused ring systems.

An example of a 3-membered heterocyclic group is aziridinyl. An example of a 4-membered heterocyclic group is azetidinyl (derived from azetidine). An example of a 5-membered heterocyclic group is thiazolyl. An example of a 6-membered heterocyclic group is pyridyl, and an example of a 10-membered heterocyclic group is quinolinyl.

Examples of non-aromatic heterocyclic groups are pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3H-indolyl and quinolizinyl.

Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups may be C-attached or N-attached where such is possible. For instance, a group derived from pyrrole may be pyrrol-1-yl (N-attached) or pyrrol-3-yl (C-attached). Further, a group derived from imidazole may be imidazol-1-yl or imidazol-3-yl (both N-attached) or imidazol-2-yl, imidazol-4-yl or imidazol-5-yl (all C-attached). The heterocyclic groups include benzo-fused ring systems and ring systems substituted with one or two oxo (=O) moieties such as pyrrolidin-2-one. Depending on the structure, a heterocycle group can be a monoradical or a diradical (i.e., a heterocyclene group).

A "heteroalicyclic" or "heterocycloalkyl" group refers to a cycloalkyl group that includes at least one ring atom that is not a carbon, i.e. at least one ring atom is a heteroatom selected from nitrogen, oxygen and sulfur. The heterocycloalkyl radicals may be fused with an aryl or heteroaryl. The term heteroalicyclic also includes all ring forms of the carbohydrates, including but not limited to the monosaccharides, the disaccharides and the oligosaccharides. Heterocycloalkyls have from 2 to 10 carbons in the ring. A "lower heterocycloalkyl" has 2 to 8 ring carbon atoms. It is understood that when referring to the number of carbon atoms in a heterocycloalkyl, the number of carbon atoms in the heterocycloalkyl is not the same at the total number of atoms (including the heteroatoms) that make up the heterocycloalkyl (i.e skeletal atoms of the heterocycloalkyl ring).

The terms "halo", "halide", and "halogen" mean fluoro, chloro, bromo and iodo.

The terms "haloalkyl," "haloalkenyl," "haloalkynyl" and "haloalkoxy" include alkyl, alkenyl, alkynyl and alkoxy structures that are substituted with one or more halogens. The halogens may the same or they may be different. A "lower haloalkyl" has 1 to 6 carbon atoms in the chain. A "lower haloalkenyl" has 2 to 6 carbon atoms in the chain. A "lower haloalkynyl" has 2 to 6 carbon atoms in the chain. A "lower haloalkoxy" has 1 to 6 carbon atoms in the chain.

The terms "fluoroalkyl" and "fluoroalkoxy" include haloalkyl and haloalkoxy groups, respectively, in which the halo is fluorine. A "lower fluoroalkyl" and a "lower fluoroalkoxy" have 1 to 6 carbon atoms in the chain.

The terms "heteroalkyl" "heteroalkenyl" and "heteroalkynyl" include optionally substituted alkyl, alkenyl and alkynyl radicals and which have one or more skeletal chain atoms selected from an atom other than carbon, e.g., oxygen, nitrogen, sulfur, phosphorus, silicon, or combinations thereof. The heteroatom(s) may be placed at any interior position of the heteroalkyl group. Examples include, but are not limited to, —$CH_2$—O—$CH_3$, —$CH_2$—$CH_2$—O—$CH_3$, —$CH_2$—NH—$CH_3$, —$CH_2$—$CH_2$—NH—$CH_3$, —$CH_2$—N($CH_3$)—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. In addition, up to two heteroatoms may be consecutive, such as, by way of example, —$CH_2$—NH—$OCH_3$ and —$CH_2$—O—Si($CH_3$)$_3$. A "lower heteroalkyl" has 1 to 6 carbon atoms in the chain. A "lower heteroalkenyl" has 2 to 6 carbon atoms in the chain. A "lower heteroalkynyl" has 2 to 6 carbon atoms in the chain.

The term "bond" or "single bond" refers to a chemical bond between two atoms, or two moieties when the atoms joined by the bond are considered to be part of larger substructure.

The term "moiety" refers to a specific segment or functional group of a molecule. Chemical moieties are often recognized chemical entities embedded in or appended to a molecule.

A "cyano" group refers to a —CN group.
An "isocyanato" group refers to a —NCO group.
An "isothiocyanato" group refers to a —NCS group.
"Acyl" refers to a RC(=O)— group.
"Acyloxy" refers to a RC(=O)O— group.
"Sulfanyl" refers to a —S— moiety.
"Sulfinyl" or "sulfoxide" refers to a —S(=O)— moiety.
"Sulfonyl" refers to a —S(=O)$_2$— moiety.
A "mercaptyl" group or "thioalkoxy" or "alkylthio" refers to a (alkyl)S— group.
A "thiocyanato" group refers to a —CNS group.

As used herein, the substituent "R" appearing by itself and without a number designation refers to a substituent selected from among from alkyl, cycloalkyl, aryl, heteroaryl (bonded through a ring carbon) and non-aromatic heterocycle (bonded through a ring carbon).

The term "optionally substituted" or "substituted" means that the referenced group may be substituted with one or more additional group(s) individually and independently selected from $C_1$-$C_6$alkyl, $C_3$-$C_8$cycloalkyl, aryl, heteroaryl, $C_2$-$C_6$heteroalicyclic, hydroxy, $C_1$-$C_6$alkoxy, aryloxy, $C_1$-$C_6$alkylthio, arylthio, $C_1$-$C_6$alkylsulfoxide, arylsulfoxide, $C_1$-$C_6$alkylsulfone, arylsulfone, cyano, halo, $C_2$-$C_8$acyl, $C_2$-$C_8$acyloxy, nitro, $C_1$-$C_6$haloalkyl, $C_1$-$C_6$fluoroalkyl, and amino, including $C_1$-$C_6$alkylamino, and the protected derivatives thereof.

By way of example only, an optional substituents may be $L^sR^s$, wherein each $L^s$ is independently selected from a bond, —O—, —C(=O)—, —S—, —S(=O)—, —S(=O)$_2$—, —NH—, —NHC(=O)—, —C(=O)NH—, S(=O)$_2$NH—, —NHS(=O)$_2$—, —OC(=O)NH—, —NHC(=O)O—, —($C_1$-$C_6$alkyl)-, or —($C_2$-$C_6$alkenyl)-; and each $R^s$ is independently selected from H, ($C_1$-$C_4$alkyl), ($C_3$-$C_8$cycloalkyl), heteroaryl, aryl, and $C_1$-$C_6$heteroalkyl. Optionally substituted non-aromatic groups may be substituted with one or more oxo (=O). The protecting groups that may form the protective derivatives of the above substituents are known to those of skill in the art.

The compounds presented herein may possess one or more stereocenters and each center may exist in the R or S configuration. The compounds presented herein include all diastereomeric, enantiomeric, and epimeric forms as well as the appropriate mixtures thereof. Stereoisomers may be obtained, if desired, by methods known in the art such as, for example, the separation of individual stereoisomers by chiral chromatographic columns or by stereoselective synthesis.

The methods and formulations described herein include the use of N-oxides, crystalline forms (also known as polymorphs), or pharmaceutically acceptable salts of compounds having the structure of any of Formula I, Formula Ia, Formula Ib, Formula Ic, Formula Id, Formula Ie, Formula If, Formula Ig, Formula Ih, Formula II, Formula IIa, Formula IIb, Formula IIc, Formula IId, Formula IIe, Formula IIf, Formula IIg, Formula IIh, Formula III, Formula IIIa, Formula IIIb, Formula IIIc, Formula IIId, Formula IIIe, Formula IIIf, Formula IIIg, Formula IIIh, Formula IV, Formula V, Formula VI, Formula VII, Formula VIII, as well as active metabolites of these compounds having the same type of activity. In some situations, compounds may exist as tautomers. All tautomers are included within the scope of the compounds presented herein. In addition, the compounds described herein can exist in unsolvated as well as solvated forms with pharmaceutically acceptable solvents such as water, ethanol, and the like. The solvated forms of the compounds presented herein are also considered to be disclosed herein.

The term "acceptable" with respect to a formulation, composition or ingredient, as used herein, means having no persistent detrimental effect on the general health of the subject being treated.

As used herein, amelioration of the symptoms of a particular disease, disorder or condition by administration of a particular compound or pharmaceutical composition refers to any lessening of severity, delay in onset, slowing of progression, or shortening of duration, whether permanent or temporary, lasting or transient that can be attributed to or associated with administration of the compound or composition.

The term "modulate," as used herein, means to interact with a target either directly or indirectly so as to alter the activity of the target, including, by way of example only, to enhance the activity of the target, to inhibit the activity of the target, to limit the activity of the target, or to extend the activity of the target.

As used herein, the term "modulator" refers to a compound that alters an activity of a molecule. For example, a modulator can cause an increase or decrease in the magnitude of a certain activity of a molecule compared to the magnitude of the activity in the absence of the modulator. In certain embodiments, a modulator is an inhibitor, which decreases the magnitude of one or more activities of a molecule. In certain embodiments, an inhibitor completely prevents one or more activities of a molecule. In certain embodiments, a modulator is an activator, which increases the magnitude of at least one activity of a molecule. In certain embodiments the presence of a modulator results in an activity that does not occur in the absence of the modulator.

As used herein, the term "target activity" refers to a biological activity capable of being modulated by a selective modulator. Certain exemplary target activities include, but are not limited to, binding affinity, signal transduction, enzymatic activity, tumor growth, inflammation or inflammation-related processes, and amelioration of one or more symptoms associated with a disease or condition.

The term "cancer," as used herein refers to an abnormal growth of cells, which tend to proliferate in an uncontrolled way and, in some cases, to metastasize (spread). The types of cancer include, but is not limited to, solid tumors (such as those of the bladder, bowel, brain, breast, endometrium, heart, kidney, lung, lymphatic tissue (lymphoma), ovary, pancreas or other endocrine organ (thyroid), prostate, skin (melanoma) or hematological tumors (such as the leukemias). See, Ding X Z et al., Anticancer Drugs. 2005 June; 16(5):467-73. Review; Chen X et al., Clin Cancer Res. 2004 Oct. 1; 10(19):6703-9, each of which are incorporated by reference herein in their entirety.

The term "carrier," as used herein, refers to relatively nontoxic chemical compounds or agents that facilitate the incorporation of a compound into cells or tissues.

The terms "co-administration" or the like, as used herein, are meant to encompass administration of the selected therapeutic agents to a single patient, and are intended to include treatment regimens in which the agents are administered by the same or different route of administration or at the same or different time.

The term "diluent" refers to chemical compounds that are used to dilute the compound of interest prior to delivery. Diluents can also be used to stabilize compounds because they can provide a more stable environment. Salts dissolved in buffered solutions (which also can provide pH control or maintenance) are utilized as diluents in the art, including, but not limited to a phosphate buffered saline solution.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The terms "kit" and "article of manufacture" are used as synonyms.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyl transferases catalyze the transfer of an activated glucuronic-acid molecule to aromatic alcohols, aliphatic alcohols, carboxylic acids, amines and free sulfhydryl groups. Further information on metabolism may be obtained from The Pharmacological Basis of Therapeutics, 9th Edition, McGraw-Hill (1996). Metabolites of the compounds disclosed herein can be identified either by administration of compounds to a host and analysis of tissue samples from the host, or by incubation of compounds with hepatic cells in vitro and analysis of the resulting compounds. Both methods are well known in the art.

By "pharmaceutically acceptable," as used herein, refers a material, such as a carrier or diluent, which does not abrogate the biological activity or properties of the compound, and is relatively nontoxic, i.e., the material may be administered to an individual without causing undesirable biological effects or interacting in a deleterious manner with any of the components of the composition in which it is contained.

The term "pharmaceutically acceptable salt" refers to a formulation of a compound that does not cause significant irritation to an organism to which it is administered and does not abrogate the biological activity and properties of the compound.

The term "subject" or "patient" encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods and compositions provided herein, the mammal is a human.

The terms "treat," "treating" or "treatment," as used herein, include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Exemplary Pharmaceutical Compositions/Formulations

For convenience, the pharmaceutical compositions and formulations described in this section and other parts herein use a single formula, such as "Formula I," by way of example. In addition, the pharmaceutical compositions and formulations described herein apply equally well to all formulae presented herein that fall within the scope of Formula (I). For example, the pharmaceutical compositions and formulations described herein can be applied to compounds having the structure of any of Formula I, Formula Ia, Formula Ib, Formula Ic, Formula Id, Formula Ie, Formula If, Formula Ig, Formula Ih, Formula II, Formula IIa, Formula IIb, Formula IIc, Formula IId, Formula IIe, Formula IIf, Formula IIg, Formula IIh, Formula III, Formula IIIa, Formula IIIb, Formula IIIc, Formula IIId, Formula IIIe, Formula IIIf, Formula IIIg, Formula IIIh, Formula IV, Formula V, Formula VI, Formula VII, Formula VIII, as well as to all of the specific compounds that fall within the scope of these generic formulae.

Pharmaceutical compositions may be formulated in a conventional manner using one or more physiologically acceptable carriers including excipients and auxiliaries which facilitate processing of the active compounds into preparations which can be used pharmaceutically. Proper formulation is dependent upon the route of administration chosen. Any of the well-known techniques, carriers, and excipients may be used as suitable and as understood in the art. A summary of pharmaceutical compositions described herein may be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference in their entirety.

Provided herein are pharmaceutical compositions that include a compound described herein and a pharmaceutically acceptable diluent(s), excipient(s), and/or carrier(s). In addition, the compounds described herein can be administered as pharmaceutical compositions in which compounds described herein are mixed with other active ingredients, as in combination therapy.

A pharmaceutical composition, as used herein, refers to a mixture of a compound described herein with other chemical components, such as carriers, stabilizers, diluents, dispersing agents, suspending agents, thickening agents, and/or excipients. The pharmaceutical composition facilitates administration of the compound to an organism. In practicing the methods of treatment or use provided herein, therapeutically effective amounts of compounds described herein are administered in a pharmaceutical composition to a mammal having a disease or condition to be treated. Preferably, the mammal is a human. A therapeutically effective amount can vary widely depending on the severity of the disease, the age and relative health of the subject, the potency of the compound used and other factors. The compounds can be used singly or in combination with one or more therapeutic agents as components of mixtures.

For intravenous injections, compounds described herein may be formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants are generally known in the art. For other parenteral injections, appropriate formulations may include aqueous or nonaqueous solutions, preferably with physiologically compatible buffers or excipients. Such excipients are generally known in the art.

For oral administration, compounds described herein can be formulated readily by combining the active compounds with pharmaceutically acceptable carriers or excipients well known in the art. Such carriers enable the compounds described herein to be formulated as tablets, powders, pills, dragees, capsules, liquids, gels, syrups, elixirs, slurries, suspensions and the like, for oral ingestion by a patient to be treated.

Pharmaceutical preparations for oral use can be obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients include, but are not limited to, fillers such as sugars, including lactose, sucrose, mannitol, or sorbitol; cellulose preparations such as: for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. If desired, disintegrating agents may be added, such as the cross-linked croscarmellose sodium, polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal or sublingual administration, the compositions may take the form of tablets, lozenges, or gels formulated in a conventional manner. Parental injections may involve bolus injection or continuous infusion. Formulations for injection may be presented in unit dosage form, e.g., in ampoules or in multi-dose containers, with an added preservative. The pharmaceutical composition of the compounds described herein may be in a form suitable for parenteral injection as a sterile suspensions, solutions or emulsions in oily or aqueous vehicles, and may contain formulatory agents such as suspending, stabilizing and/or dispersing agents. Pharmaceutical formulations for parenteral administration include aqueous solutions of the active compound(s) in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. Alternatively, the active ingredient may be in powder form for constitution with a suitable vehicle, e.g., sterile pyrogen-free water, before use.

The compounds described herein can be administered topically and can be formulated into a variety of topically administrable compositions, such as solutions, suspensions, lotions, gels, pastes, medicated sticks, balms, creams or ointments. Such pharmaceutical compounds can contain solubilizers, stabilizers, tonicity enhancing agents, buffers and preservatives.

Formulations suitable for transdermal administration of compounds described herein may employ transdermal delivery devices and transdermal delivery patches and can be lipophilic emulsions or buffered, aqueous solutions, dissolved and/or dispersed in a polymer or an adhesive. Such patches may be constructed for continuous, pulsatile, or on demand delivery of pharmaceutical agents. Still further, transdermal delivery of the compounds described herein can be accomplished by means of iontophoretic patches and the like. Additionally, transdermal patches can provide controlled delivery of the compounds described herein. The rate of absorption can be slowed by using rate-controlling membranes or by trapping the compound within a polymer matrix or gel. Conversely, absorption enhancers can be used to increase absorption. An absorption enhancer or carrier can include absorbable pharmaceutically acceptable solvents to assist passage through the skin. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

For administration by inhalation, the compounds described herein may be in a form as an aerosol, a mist, or a powder. Pharmaceutical compositions of compounds described herein are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide, or other suitable gas. In the case of a pressurized aerosol the dosage unit may be determined by providing a valve to deliver a metered amount. Capsules and cartridges of, such as, by way of example only, gelatin for use in an inhaler or insufflator may be formulated containing a powder mix of the compound and a suitable powder base such as lactose or starch.

The compounds described herein may also be formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

Pharmaceutical compositions may be formulated in conventional manner using one or more physiologically acceptable carriers comprising excipients and auxiliaries which facilitate processing of the active compounds into preparations which can be used pharmaceutically. Proper formulation is dependent upon the route of administration chosen. Any of the well-known techniques, carriers, and excipients may be used as suitable and as understood in the art. Pharmaceutical compositions that include a compound described herein may be manufactured in a conventional manner, such as, by way of example only, by means of conventional mixing, dissolving, granulating, dragee-making, levigating, emulsifying, encapsulating, entrapping or compression processes.

The pharmaceutical compositions will include at least one pharmaceutically acceptable carrier, diluent and/or excipient and a compound described herein as an active ingredient in free-acid or free-base form, or in a pharmaceutically acceptable salt form. In addition, the methods and pharmaceutical compositions described herein include the use of N-oxides, crystalline forms (also known as polymorphs), as well as active metabolites of these compounds having the same type of activity.

In some situations, compounds may exist as tautomers. All tautomers are included within the scope of the compounds presented herein. In some embodiments, cyclic compounds described herein may exist in equilibrium with open chain forms. Both forms, cyclic and open form, are included. Additionally, the compounds described herein can exist in unsolvated as well as solvated forms with pharmaceutically acceptable solvents such as water, ethanol, and the like. The solvated forms of the compounds presented herein are also considered to be disclosed herein. In addition, the pharmaceutical compositions may include other medicinal or pharmaceutical agents, carriers, adjuvants, such as preserving, stabilizing, wetting or emulsifying agents, solution promoters, salts for regulating the osmotic pressure, and/or buffers. In addition, the pharmaceutical compositions can also contain other therapeutically valuable substances.

Methods for the preparation of compositions that include the compounds described herein include formulating the compounds with one or more inert, pharmaceutically acceptable excipients or carriers to form a solid, semi-solid or liquid. Solid compositions include, but are not limited to, powders, tablets, dispersible granules, capsules, cachets, and suppositories. Liquid compositions include solutions in which a compound is dissolved, emulsions that include a compound described herein, or a solution containing liposomes, micelles, or nanoparticles that include a compound as disclosed herein. Semi-solid compositions include, but are not limited to, gels, suspensions and creams. The compositions may be in liquid solutions or suspensions, solid forms suitable for solution or suspension in a liquid prior to use, or as emulsions. These compositions may also contain minor amounts of nontoxic, auxiliary substances, such as wetting or emulsifying agents, pH buffering agents, and so forth.

A composition that includes a compound described herein can illustratively take the form of a liquid where the agents are present in solution, in suspension, or both. Typically when the composition is administered as a solution or suspension, a first portion of the compound is present in solution and a second portion of the compound is present in particulate form, in suspension in a liquid matrix. In some embodiments, a liquid composition may include a gel formulation. In other embodiments, the liquid composition is aqueous.

Aqueous suspensions can also contain one or more polymers as suspending agents. Useful polymers include water-soluble polymers such as cellulosic polymers, e.g., hydroxypropyl methylcellulose, and water-insoluble polymers such as cross-linked carboxyl-containing polymers. Useful compositions can also include a mucoadhesive polymer, selected from, for example, carboxymethylcellulose, carbomer (acrylic acid polymer), poly(methylmethacrylate), polyacrylamide, polycarbophil, acrylic acid/butyl acrylate copolymer, sodium alginate, and dextran.

Compositions may also include solubilizing agents to aid in the solubility of a compound described herein. The term "solubilizing agent" generally includes agents that result in formation of a micellar solution or a true solution of the agent. Certain acceptable nonionic surfactants, for example polysorbate 80, can be useful as solubilizing agents, as can ophthalmically acceptable glycols, polyglycols, e.g., polyethylene glycol 400, and glycol ethers.

Compositions may also include one or more pH adjusting agents or buffering agents, including acids such as acetic acid, boric acid, citric acid, lactic acid, phosphoric acid and hydrochloric acid; bases such as sodium hydroxide, sodium carbonate, sodium bicarbonate, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

Compositions may also include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

Other compositions may also include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

Still other compositions may include one or more surfactants to enhance physical stability or for other purposes. Suitable nonionic surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

Still other compositions may include one or more antioxidants to enhance chemical stability where required. Suitable antioxidants include, by way of example only, ascorbic acid and sodium metabisulfite.

Aqueous suspension compositions can be packaged in single-dose non-reclosable containers. Alternatively, multiple-dose reclosable containers can be used, in which case it is typical to include a preservative in the composition.

Alternatively, other delivery systems for hydrophobic pharmaceutical compounds may be employed. Liposomes and emulsions are well known examples of delivery vehicles or carriers for hydrophobic drugs. Certain organic solvents such as N-methylpyrrolidone also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds over the course of 4-24 hours. Depending on the chemical nature and the biological stability of the therapeutic reagent, additional strategies for protein stabilization may be employed.

All of the formulations described herein may benefit from antioxidants, metal chelating agents, thiol containing compounds and other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

Exemplary Methods of Dosing and Treatment Regimens

For convenience, the methods of dosing and treatment regimens described in this section and other parts herein use a single formula by way of example. In addition, the methods of dosing and treatment regimens described herein apply equally well to all formulae presented herein that fall within the scope of Formula (I). For example, the methods of dosing and treatment regimens described herein can be applied to compounds having the structure of any of Formula I, Formula Ia, Formula Ib, Formula Ic, Formula Id, Formula Ie, Formula If, Formula Ig, Formula Ih, Formula II, Formula IIa, Formula IIb, Formula IIc, Formula IId, Formula IIe, Formula IIf, Formula IIg, Formula IIh, Formula III, Formula IIIa, Formula IIIb, Formula IIIc, Formula IIId, Formula IIIe, Formula IIIf, Formula IIIg, Formula IIIh, Formula IV, Formula V, Formula VI, Formula VII, Formula VIII, as well as to all of the specific compounds that fall within the scope of these generic formulae.

The compounds described herein can be used in the preparation of medicaments for the treatment or prevention of a specific disease or condition. In addition, a method for treating any of the diseases or conditions described herein in a subject in need of such treatment, involves administration of pharmaceutical compositions containing at least one compound described herein or a pharmaceutically acceptable salt, pharmaceutically acceptable N-oxide, pharmaceutically active metabolite, pharmaceutically acceptable prodrug, or pharmaceutically acceptable solvate thereof, in therapeutically effective amounts to said subject The compositions containing the compound(s) described herein can be administered for prophylactic and/or therapeutic treatments. In therapeutic applications, the compositions are administered to a patient already suffering from a disease or condition, in an amount sufficient to cure or at least partially arrest the symptoms of the disease or condition. Amounts effective for this use will depend on the severity and course of the disease or condition, previous therapy, the patient's health status, weight, and response to the drugs, and the judgment of the treating physician. It is considered well within the skill of the art for one to determine such therapeutically effective amounts by routine experimentation (including, but not limited to, a dose escalation clinical trial).

In prophylactic applications, compositions containing the compounds described herein are administered to a patient susceptible to or otherwise at risk of a particular disease, disorder, or condition. Such an amount is defined to be a "prophylactically effective amount or dose." In this use, the precise amounts also depend on the patient's state of health, weight, and the like. It is considered well within the skill of the art for one to determine such prophylactically effective amounts by routine experimentation (e.g., a dose escalation clinical trial). When used in a patient, effective amounts for this use will depend on the severity and course of the disease, disorder or condition, previous therapy, the patient's health status and response to the drugs, and the judgment of the treating physician.

In the case wherein the patient's condition does not improve, upon the doctor's discretion the administration of the compounds described herein may be administered chronically, that is, for an extended period of time, including throughout the duration of the patient's life in order to ameliorate or otherwise control or limit the symptoms of the patient's disease or condition.

In the case wherein the patient's status does improve, upon the doctor's discretion the administration of the compounds described herein may be given continuously; alternatively, the dose of the compounds described herein being administered may be temporarily reduced or temporarily suspended for a certain length of time (i.e., a "drug holiday"). The length of the drug holiday can vary between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, and 365 days. The dose reduction during a drug holiday may be from 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

Once improvement of the patient's conditions has occurred, a maintenance dose is administered if necessary. Subsequently, the dosage or the frequency of administration, or both, can be reduced, as a function of the symptoms, to a level at which the improved state of the disease, disorder or condition is maintained. Patients can, however, require intermittent treatment on a long-term basis upon any recurrence of symptoms.

The amount of a given agent that will correspond to such an amount will vary depending upon factors such as the particular compound, disease condition and its severity, the identity (e.g., age, weight, gender, etc.) of the subject or host in need of treatment, but can nevertheless be routinely determined in a manner known in the art according to the particular circumstances surrounding the case, including, e.g., the specific agent being administered, the route of administration, the condition being treated, and the subject or host being treated. In general, however, doses employed for adult human treatment will typically be in the range of 0.02-5000 mg per day, in some embodiments 1-1500 mg per day. The desired dose may conveniently be presented in a single dose or as divided doses administered simultaneously (or over a short period of time) or at appropriate intervals, for example as two, three, four or more sub-doses per day.

The pharmaceutical composition described herein may be in unit dosage forms suitable for single administration of precise dosages. In unit dosage form, the formulation is divided into unit doses containing appropriate quantities of one or more compound. The unit dosage may be in the form of a package containing discrete quantities of the formulation. Non-limiting examples are packaged tablets or capsules, and powders in vials or ampoules. Aqueous suspension compositions can be packaged in single-dose non-reclosable containers. Alternatively, multiple-dose reclosable containers can be used, in which case it is typical to include a preservative in the composition. By way of example only, formulations for parenteral injection may be presented in unit dosage form, which include, but are not limited to ampoules, or in multi-dose containers, with an added preservative.

The daily dosages appropriate for the compounds described herein are from about 0.01 to 2.5 mg/kg per body weight. An indicated daily dosage in the larger mammal, including, but not limited to, humans, is in the range from about 0.5 mg to about 100 mg, conveniently administered in divided doses, including, but not limited to, up to four times a day or in extended release form. Suitable unit dosage forms for oral administration include from about 1 mg to about 50 mg active ingredient. The foregoing ranges are merely suggestive, as the number of variables in regard to an individual treatment regime is large, and considerable excursions from these recommended values are not uncommon. Such dosages may be altered depending on a number of variables, not limited to the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens can be determined by standard pharmaceutical procedures in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index and it can be expressed as the ratio between $LD_{50}$ and $ED_{50}$. Compounds exhibiting high therapeutic indices are preferred. The data obtained from cell culture assays and animal studies can be used in formulating a range of dosage for use in human. The dosage of such compounds lies preferably within a range of circulating concentrations that include the $ED_{50}$ with minimal toxicity. The dosage may vary within this range depending upon the dosage form employed and the route of administration utilized.

In effecting treatment of a patient in need of such treatment, a compound of the invention can be administered in any form and route which makes the compound bioavailable. The compounds of the invention can be administered by a variety of routes, including oral and parenteral routes, more particularly by inhalation, subcutaneously, intramuscularly, intravenously, transdermally, intranasally, rectally, vaginally, occularly, topically, sublingually, and buccally, intraperitoneally, intravenously, intraarterially, transdermally, sublingually, intramuscularly, rectally, transbuccally, intranasally, intraadiposally, intrathecally and via local delivery for example by catheter or stent.

One skilled in the art can readily select the proper form and route of administration depending upon the particular characteristics of the compound selected, the disorder or condition to be treated, the stage of the disorder or condition, and other relevant circumstances. The pharmaceutical compositions of the invention may be administered to the patient, for example, in the form of tablets, capsules, cachets, papers, lozenges, wafers, elixirs, ointments, transdermal patches, aerosols, inhalants, suppositories, solutions, and suspensions.

The pharmaceutical compositions of the present invention are prepared in a manner well known in the pharmaceutical art and include at least one of the compounds of the invention as the active ingredient. The amount of a compound of the present invention may be varied depending upon its particular form and may conveniently be between 1% to about 70% of the weight of the unit dosage form. The term "pharmaceutically acceptable excipient" refers to those typically used in preparing pharmaceutical compositions and should be pharmaceutically pure and non-toxic in the amounts used. They generally are a solid, semi-solid, or liquid material which can serve as a vehicle or medium for the active ingredient.

Some examples of pharmaceutically acceptable excipients are found in Remington's Pharmaceutical Sciences and the Handbook of Pharmaceutical Excipients and include diluents, vehicles, carriers, ointment bases, binders, disintegrates, lubricants, glidants, sweetening agents, flavoring agents, gel bases, sustained release matrices, stabilizing agents, preservatives, solvents, suspending agents, buffers, emulsifiers, dyes, propellants, coating agents, and others.

The present pharmaceutical compositions are preferably formulated in a unit dosage form, each dosage typically containing from about 0.5 mg to about 1000 mg of the compounds of the invention. The term "unit dosage form" refers to a physically discrete unit suitable as a single dosage, each unit containing a predetermined quantity of active ingredient, in association with a suitable pharmaceutical excipient, by which one or more is used throughout the dosing regimen to produce the desired therapeutic effect.

In one particular variation, the composition is a pharmaceutical composition adapted for oral administration, such as a liquid formulation, for example, a solution or suspension, adapted for oral administration or a tablet or a capsule. In still another particular variation, the pharmaceutical composition is a liquid formulation adapted for parenteral administration.

In another embodiment, the invention provides methods of treating conditions associated with JAK, comprising: administering to a patient in need thereof an effective amount of a compound of the invention. In another embodiment, the invention provides a method of inhibiting a JAK: comprising, contacting the enzyme with a compound of the invention. In a further embodiment, the invention provides a method of inhibiting a JAK: comprising, administering a first compound to a subject that is converted in vivo to a compound of the invention.

"Conditions associated with JAK" include disorders and diseases in which the inhibition of JAK provides a therapeutic benefit, such as cancer, allergy/asthma, diseases and conditions of the immune system, inflammation, disease and conditions of the central nervous system (CNS), cardiovascular disease, viral infections, dermatological disease, and diseases and conditions related to uncontrolled angiogenesis, and the like. Where general terms are used herein to describe conditions associated with JAK it is understood that the more specifically described conditions mentioned in the various diagnostic manuals and other materials are included within the scope of this invention.

For example, it is understood that the treatment of cancer includes treatment of all neoplasia, regardless of their histopathological appearance. Particularly, the cancers that can be treated include, but are not limited to, cancer of blood, including myelofibrosis, leukemia (including acute myelogenous leukemia, chronic myelogenous leukemia, acute lymphocytic leukemia, chronic lymphocytic leukemia), cancer of the skin, including melanoma, basal cell carcinoma, and squamous cell carcinoma, bone, liver, lung (including small-cell lung tumor, non small-cell lung cancer and bronchioalveolar cancer), brain, breast, prostate, larynx, gall bladder, pancreas, rectum, bile duct, parathyroid, thyroid, adrenal, neural tissue, bladder, spleen, head and neck, included the jaw, mouth, and nose, colon, stomach, testes, esophagus, uterus, cervix and vulva, colorectal, bronchi, bile duct, bladder, kidney, ovary, pancreas, multiple myeloma, lymphomas, basal cell carcinoma, squamous cell carcinoma of both ulcerating and papillary type, osteo sarcoma, Ewing's sarcoma, veticulum cell sarcoma, myeloma, giant cell tumor, islet cell tumor, acute and chronic lymphocytic and granulocytic tumors, hairy-cell tumor, adenoma, hyperplasia, medullary carcinoma, pheochromocytoma, mucosal neuronms, intestinal ganglioneuromas, hyperplastic corneal nerve tumor, marfanoid habitus tumor, Wilm's tumor, seminoma, ovarian tumor, leiomyomater tumor, cervical dysplasia and in situ carcinoma, neuroblastoma, retinoblastoma, myelodysplastic syndrome, mycosis fungicide, rhabdomyosarcoma, astrocytoma, non-Hodgkin's lymphoma, Kaposi's sarcoma, osteogenic and other sarcoma, malignant hypercalcemia, polycythermia vera, adenocarcinoma, glioblastoma multiforma, glioma, lymphomas, epidermoid carcinomas, and other carcinomas and sarcomas.

Benign tumors may also be treated by the compounds of the present invention and include, but are not limited to, hemangiomas, hepatocellular adenoma, cavernous haemangioma, focal nodular hyperplasia, acoustic neuromas, neurofibroma, bile duct adenoma, bile duct cystanoma, fibroma, lipomas, leiomyomas, mesotheliomas, teratomas, myxomas, nodular regenerative hyperplasia, trachomas, pyogenic granulomas, and the like, and hamartoma conditions such as Peutz-Jeghers Syndrome (PJS), Cowden disease, Bannayan-Riley-Ruvalcaba Syndrome (BRRS), Proteus syndrome, Lhermitte-Duclos disease and Tuberous Sclerosis (TSC).

The compounds of the present invention may also be used to treat abnormal cell proliferation due to insults to body tissue during surgery. These insults may arise as a result of a variety of surgical procedures such as joint surgery, bowel surgery, and cheloid scarring. Diseases that produce fibrotic tissue include emphysema. Repetitive motion disorders that may be treated using the present invention include carpal tunnel syndrome.

The compounds of the invention may also be useful in the prevention of restenosis that is the control of undesired proliferation of normal cells in the vasculature in response to the introduction of stents in the treatment of vasculature disease.

Proliferative responses associated with organ transplantation that may be treated using JAK inhibitors of the invention include proliferative responses contributing to potential organ rejections or associated complications. Specifically, these proliferative responses may occur during transplantation of the heart, lung, liver, kidney, and other body organs or organ systems.

The compounds of the invention may also be useful the treatment of abnormal angiogenesis including the abnormal angiogenesis accompanying rheumatoid arthritis, ischemic-reperfusion related brain edema and injury, cortical ischemia, ovarian hyperplasia and hypervascularity, (polycystic ovary syndrome), endometriosis, psoriasis, diabetic retinopathy, and other ocular angiogenic diseases such as retinopathy of prematurity (retrolental fibroplastic), macular degeneration, corneal graft rejection, neuroscular glaucoma, Oster Webber syndrome, retinal/choroidal neuvascularization and corneal neovascularization, Best's disease, myopia, optic pits, Stargart's diseases, Pagets disease, vein occlusion, artery occlusion, sickle cell anemia, sarcoid, syphilis, pseudoxanthoma elasticum carotid abstructive diseases, chronic uveitis/vitritis, mycobacterial infections, Lyme's disease, systemic lupus erythematosis, retinopathy of prematurity, Eales disease, diabetic retinopathy, macular degeneration, Bechets diseases, infections causing a retinitis or chroiditis, presumed ocular histoplasmosis, pars planitis, chronic retinal detachment, hyperviscosity syndromes, toxoplasmosis, trauma and post-laser complications, diseases associated with rubesis (neovascularization of the angle), diseases caused by the abnormal proliferation of fibrovascular or fibrous tissue including all forms of proliferative vitreoretinopathy, atopic keratitis, superior limbic keratitis, pterygium keratitis sicca, sjogrens, acne rosacea, phylectenulosis, diabetic retinopathy, retinopathy of prematurity, corneal graft rejection, Mooren's ulcer, Terrien's marginal degeneration, marginal keratolysis, polyarteritis, Wegener sarcoidosis, scleritis, periphigoid radial keratotomy, neovascular glaucoma and retrolental fibroplasia, syphilis, Mycobacteria infections, lipid degeneration, chemical burns, bacterial ulcers, fungal ulcers, Herpes simplex infections, Herpes zoster infections, protozoan infections, and Kaposi sarcoma, Alzheimer's disease, Parkinson's disease amyotrophic lateral sclerosis (ALS), epilepsy, seizures, Huntington's disease, polyglutamine diseases, traumatic brain injury, ischemic and hemorrhaging stroke, cerebral ischemias or neurodegenerative disease, including apoptosis-driven neurodegenerative disease, caused by traumatic injury, acute hypoxia, ischemia or glutamate neurotoxicity.

For example, it is understood that treatments of inflammation include, but are not limited to, acute pancreatitis, chronic pancreatitis, asthma, allergies, chronic obstructive pulmonary disease, adult respiratory distress syndrome and chronic inflammatory diseases associated with uncontrolled angiogenesis, inflammatory bowel diseases such as Crohn's disease and ulcerative colitis, psoriasis, sarcoidois, and rheumatoid arthritis, sarcoidosis, and multisystem granulomatous disorder.

For example, it is understood that treatment of autoimmune includes, but is not limited to, glomerulonephritis, rheumatoid arthritis, systemic lupus erythematosus, scleroderma, chronic thyroiditis, Graves' disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, graft vs. host disease, multiple sclerosis, or Sjoegren's syndrome.

The compounds of the present invention are also useful for treating obesity, diabetes, insulin resistance, metabolic syndrome, and hyperlipidemia.

A wide variety of therapeutic agents may have a therapeutic additive or synergistic effect with the compounds according to the present invention. Combination therapies that comprise one or more compounds of the present invention with one or more other therapeutic agents can be used, for example, to: (1) enhance the therapeutic effect(s) of the one or more compounds of the present invention and/or the one or more other therapeutic agents; (2) reduce the side effects exhibited by the one or more compounds of the present invention and/or the one or more other therapeutic agents; and/or (3) reduce the effective dose of the one or more compounds of the present invention and/or the one or more other therapeutic agents. It is noted that combination therapy is intended to cover when agents are administered before or after each other (sequential therapy) as well as when the agents are administered at the same time.

Examples of such therapeutic agents that may be used in combination with the present compounds include, but are not limited to, anti-cell proliferation agents, anticancer agents, alkylating agents, antibiotic agents, antimetabolic agents, hormonal agents, plant-derived agents, and biologic agents.

Examples of such therapeutic agents that may be used in combination with the compounds disclosed herein include, but are not limited to, anti-cell proliferation agents, anticancer agents, alkylating agents, antibiotic agents, antimetabolic agents, hormonal agents, plant-derived agents, and biologic agents.

Anti-cell proliferation agents useful in combination with the compounds of the present invention include, but are not limited to, retinoid acid and derivatives thereof, 2-methoxyestradiol, ANGIOSTATIN™ protein, ENDOSTATIN™ protein, suramin, squalamine, tissue inhibitor of metalloproteinase-I, tissue inhibitor of metalloproteinase-2, plasminogen activator inhibitor-1, plasminogen activator inhibitor-2, cartilage-derived inhibitor, paclitaxel, platelet factor 4, protamine sulphate (clupeine), sulphated chitin derivatives (prepared from queen crab shells), sulphated polysaccharide peptidoglycan complex (sp-pg), staurosporine, modulators of matrix metabolism, including for example, proline analogs ((1-azetidine-2-carboxylic acid (LACA), cishydroxyproline, d,l-3,4-dehydroproline, thiaproline, beta-aminopropionitrile fumarate, 4-propyl-5-(4-pyridinyl)-2(3H)-oxazolone, methotrexate, mitoxantrone, heparin, interferons, 2 macroglobulin-serum, chimp-3, chymostatin, beta.-cyclodextrin tetradecasulfate, eponemycin; fumagillin, gold sodium thiomalate, d-penicillamine (CDPT), beta-1-anticollagenase-serum, alpha-2-antiplasmin, bisantrene, lobenzarit disodium, n-(2-carboxyphenyl-4-chloroanthronilic acid disodium or "CCA", thalidomide, angostatic steroid, cargboxynaminolmidazole, metalloproteinase inhibitors such as BB94. Other anti-angiogenesis agents that may be used include antibodies, preferably monoclonal antibodies against these angiogenic growth factors: bFGF, aFGF, FGF-5, VEGF isoforms, VEGF-C, HGF/SF and Ang-1/Ang-2.

Inhibitors of mTOR, PI3K, MEK, MAPK, or ERK kinases are useful in combination with the compounds of the present invention. Specifically, (R)-3-(2,3-Dihydroxypropyl)-6-fluoro-5-(2-fluoro-4-iodophenylamino)-8-methylpyrido[2,3-d]pyrimidine-4,7(3H,8H)-dione useful in combination with the compounds of the present invention Inhibitors of Hedgehog kinase are useful in combination with the compounds of the present invention. Proteasome inhibitors, in particular bortezomib is useful in combination with the compounds of the present invention.

NAE inhibitors, VPS34 inhibitors, Aurora kinase, including Aurora A inhibitors, and EGFR inhibitors (both antibodies and kinase inhibitors) are useful in combination with the compounds of the present invention.

Alkylating agents useful in combination with the compounds disclosed herein include, but are not limited to, bischloroethylamines (nitrogen mustards, e.g. chlorambucil, cyclophosphamide, ifosfamide, mechlorethamine, melphalan, uracil mustard), aziridines (e.g. thiotepa), alkyl alkone sulfonates (e.g. busulfan), nitrosoureas (e.g. carmustine, lomustine, streptozocin), nonclassic alkylating agents (altretamine, dacarbazine, and procarbazine), platinum compounds (carboplastin and cisplatin). Combination therapy including a JAK inhibitor and an alkylating agent is expected to have therapeutic synergistic effects in the treatment of cancer and reduce sides affects associated with these chemotherapeutic agents.

Examples of antibiotic agents useful in combination with the compounds disclosed herein include, but are not limited to, anthracyclines (e.g. doxorubicin, daunorubicin, epirubicin, idarubicin and anthracenedione), mitomycin C, bleomycin, dactinomycin, plicatomycin. These antibiotic agents interfere with cell growth by targeting different cellular components.

Antimetabolic agents useful in combination with the compounds disclosed herein include, but are not limited to, fluorouracil (5-FU), floxuridine (5-FUdR), methotrexate, leucovorin, hydroxyurea, thioguanine (6-TG), mercaptopurine (6-MP), cytarabine, pentostatin, fludarabine phosphate, cladribine (2-CDA), asparaginase, and gemcitabine. Combination therapy including a compound disclosed herein and an antimetabolic agent is expected to have therapeutic synergistic effects on cancer and reduce sides affects associated with these chemotherapeutic agents.

Hormonal agents useful in combination with the compounds disclosed herein include synthetic estrogens (e.g. diethylstibestrol), antiestrogens (e.g. tamoxifen, toremifene, fluoxymesterol and raloxifene), antiandrogens (bicalutamide, nilutamide, and flutamide), aromatase inhibitors (e.g., aminoglutethimide, anastrozole and tetrazole), ketoconazole, goserelin acetate, leuprolide, megestrol acetate and mifepristone. Combination therapy including a compound disclosed herein and a hormonal agent is expected to have therapeutic synergistic effects on cancer and reduce sides affects associated with these chemotherapeutic agents.

Plant-derived agents useful in combination with the compounds disclosed herein include, but are not limited to, *vinca* alkaloids (e.g., vincristine, vinblastine, vindesine, vinzolidine and vinorelbine), podophyllotoxins (e.g., etoposide (VP-16) and teniposide (VM-26)), taxanes (e.g., paclitaxel and docetaxel). These plant-derived agents generally act as antimitotic agents that bind to tubulin and inhibit mitosis. Podophyllotoxins such as etoposide are believed to interfere with DNA synthesis by interacting with topoisomerase II, leading to DNA strand scission. Combination therapy including a compound disclosed herein and a plant-derived agent is expected to have therapeutic synergistic effects on cancer and reduce sides affects associated with these chemotherapeutic agents As used herein, the term "effective amount" refers to the amount of compound of the invention which treats, upon single or multiple dose administration, a patient suffering from the mentioned condition. An effective amount can be readily determined by the attending diagnostician, as one skilled in the art, by the use of known techniques and by observing results obtained under analogous circumstances.

In determining the effective amount, the dose, a number of factors are considered by the attending diagnostician, including, but not limited to: the species of patient; its size, age, and general health; the specific condition, disorder, or disease involved; the degree of or involvement or the severity of the condition, disorder, or disease, the response of the individual patient; the particular compound administered; the mode of administration; the bioavailability characteristics of the preparation administered; the dose regimen selected; the use of concomitant medication; and other relevant circumstances. An effective amount of the present use invention, including a compound of the invention, is expected to vary from about 0.1 milligram per kilogram of body weight per day (mg/kg/day) to about 40 mg/kg/day. Specific amounts can be determined by the skilled person.

In a particular embodiment the present invention provides a method for treating cancer, comprising: administering to a patient in need thereof an effective amount of a compound of invention.

The invention also provides an article of manufacture: comprising at least one compound of the invention and a label. The label may include information about the manufacturer, doses, conditions to be treated, and the use of the compound or pharmaceutical composition.

In another embodiment the invention provides a kit: comprising, at least one compound of the invention, a label, and apparatus for administration. The apparatus may include mixing vials, liquids for forming solutions or suspensions, tubing, syringes, and the like.

COMPOUNDS

Throughout the specification, groups and substituents thereof can be chosen by one skilled in the field to provide stable moieties and compounds.

Exemplary Further Forms of Compounds

Compounds described herein may possess one or more stereocenters and each center may exist in the R or S configuration. The compounds presented herein include all diastereomeric, enantiomeric, and epimeric forms as well as the appropriate mixtures thereof. Separation of steroisomers may be performed by chromatography. Alternatively, individual stereoisomers may be obtained by reacting a racemic mixture of the compound with an optically active resolving agent to form a pair of diastereoisomeric compounds, separating the diastereomers and recovering the optically pure enantiomers.

While resolution of enantiomers can be carried out using covalent diastereomeric derivatives of the compounds described herein, dissociable complexes are also possible (e.g., crystalline diastereomeric salts). Diastereomers have distinct physical properties (e.g., melting points, boiling points, solubilities, reactivity, etc.) and can be readily separated by taking advantage of these dissimilarities. The diastereomers can be separated by chiral chromatography, or by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques, Andre Collet, Samuel H. Wilen, "Enantiomers, Racemates and Resolutions", John Wiley And Sons, Inc., 1981, herein incorporated by reference in its entirety. Stereoisomers may also be obtained by stereoselective synthesis.

In some situations, compounds may exist as tautomers. All tautomers are included within the formulas described herein.

In some cases, cyclic compounds described herein may be in equilibrium with open chain forms. Closed cyclic forms as well as the corresponding open chain forms, which are in equilibrium with the closed cyclic forms, are considered part of the present disclosure.

The methods and formulations described herein include the use of N-oxides, crystalline forms (also known as polymorphs), or pharmaceutically acceptable salts of compounds described herein, as well as active metabolites of these compounds having the same type of activity. In some situations, compounds may exist as tautomers. All tautomers are included within the scope of the compounds presented herein. In addition, the compounds described herein can exist in unsolvated as well as solvated forms with pharmaceutically acceptable solvents such as water, ethanol, and the like. The solvated forms of the compounds presented herein are also considered to be disclosed herein.

In some embodiments, compounds described herein are prepared as prodrugs. A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. An example, without limitation, of a prodrug would be a compound described herein, which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety. In certain embodiments, upon in vivo administration, a prodrug is chemically converted to the biologically, pharmaceutically or therapeutically active form of the compound. In certain embodiments, a prodrug is enzymatically metabolized by one or more steps or processes to the biologically, pharmaceutically or therapeutically active form of the compound.

To produce a prodrug, a pharmaceutically active compound is modified such that the active compound will be regenerated upon in vivo administration. The prodrug can be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound. See, e.g., Nogrady (1985) Medicinal Chemistry A Biochemical Approach, Oxford University Press, New York, pages 388-392; Silverman (1992), The Organic Chemistry of Drug Design and Drug Action, Academic Press, Inc., San Diego, pages 352-401, Saulnier et al., (1994), Bioorganic and Medicinal Chemistry Letters, Vol. 4, p. (1985), each of which is incorporated by reference herein in its entirety.

Prodrug forms of the herein described compounds, wherein the prodrug is metabolized in vivo to produce a derivative as set forth herein are included within the scope of the claims. In some cases, some of the herein-described compounds may be a prodrug for another derivative or active compound.

Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. Prodrugs may be designed as reversible drug derivatives, for use as modifiers to enhance drug transport to site-specific tissues. In some embodiments, the design of a prodrug increases the effective water solubility. See, e.g., Fedorak et al., Am. J. Physiol., 269:G210-218 (1995); McLoed et al., Gastroenterol, 106:405-413 (1994); Hochhaus et al., Biomed. Chrom., 6:283-286 (1992); J. Larsen and H. Bundgaard, Int. J. Pharmaceutics, 37, 87 (1987); J. Larsen et al., Int. J. Pharmaceutics, 47, 103 (1988); Sinkula et al., J. Pharm. Sci., 64:181-210 (1975); T. Higuchi and V. Stella, Pro-drugs as Novel Delivery Systems, Vol. 14 of the A.C.S. Symposium Series; and Edward B. Roche, Bioreversible Carriers in Drug Design, American Pharmaceutical Association and Pergamon Press, 1987, all incorporated by reference herein in their entirety.

Sites on the aromatic ring portion of compounds described herein can be susceptible to various metabolic reactions, therefore incorporation of appropriate substituents on the aromatic ring structures, such as, by way of example only, halogens can reduce, minimize or eliminate this metabolic pathway.

The compounds described herein may be labeled isotopically (e.g. with a radioisotope) or by other means, including, but not limited to, the use of chromophores or fluorescent moieties, bioluminescent labels, or chemiluminescent labels.

Compounds described herein include isotopically-labeled compounds, which are identical to those recited in the various formulae and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, fluorine and chlorine, such as, for example, $_2$H, $_3$H, $_{13}$C, $_{14}$C, $_{15}$N, $_{18}$O, $_{17}$O, $_{35}$S, $_{18}$F, $_{36}$Cl, respectively. Certain isotopically-labeled compounds described herein, for example those into which radioactive isotopes such as $_3$H and $_{14}$C are incorporated, are useful in drug and/or substrate tissue distribution assays. Further, substitution with isotopes such as deuterium, i.e., $_2$H, can afford certain therapeutic advantages resulting from greater metabolic stability, for example increased in vivo half-life or reduced dosage requirements.

In additional or further embodiments, the compounds described herein are metabolized upon administration to an organism in need to produce a metabolite that is then used to produce a desired effect, including a desired therapeutic effect.

Compounds described herein may be formed as, and/or used as, pharmaceutically acceptable salts. The type of pharmaceutical acceptable salts, include, but are not limited to: (1) acid addition salts, formed by reacting the free base form of the compound with a pharmaceutically acceptable: inorganic acid, such as, for example, hydrochloric acid, hydrobromic acid, sulfuric acid, nitric acid, phosphoric acid, metaphosphoric acid, and the like; or with an organic acid, such as, for example, acetic acid, propionic acid, hexanoic acid, cyclopentanepropionic acid, glycolic acid, pyruvic acid, lactic acid, malonic acid, succinic acid, malic acid, maleic acid, fumaric acid, trifluoroacetic acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; (2) salts formed when an acidic proton present in the parent compound either is replaced by a metal ion, e.g., an alkali metal ion (e.g. lithium, sodium, potassium), an alkaline earth ion (e.g. magnesium, or calcium), or an aluminum ion; or coordinates with an organic base. Acceptable organic bases include ethanolamine, diethanolamine, triethanolamine, tromethamine, N-methylglucamine, dicyclohexylamine, tris(hydroxymethyl)methylamine, and salts with amino acids such as arginine, lysine, and the like. Acceptable inorganic bases used to form salts with compounds that include an acidic proton, include, but are not limited to, aluminum hydroxide, calcium hydroxide, potassium hydroxide, sodium carbonate, sodium hydroxide, and the like.

It should be understood that a reference to a pharmaceutically acceptable salt includes the solvent addition forms or crystal forms thereof, particularly solvates or polymorphs. Solvates contain either stoichiometric or non-stoichiometric amounts of a solvent, and may be formed during the process of crystallization with pharmaceutically acceptable solvents such as water, ethanol, and the like. Hydrates are formed when the solvent is water, or alcoholates are formed when the solvent is alcohol. Solvates of compounds described herein can be conveniently prepared or formed during the processes described herein. In addition, the compounds provided herein can exist in unsolvated as well as solvated forms. In general, the solvated forms are considered equivalent to the unsolvated forms for the purposes of the compounds and methods provided herein.

Compounds described herein may be in various forms, including but not limited to, amorphous forms, milled forms and nano-particulate forms. In addition, compounds described herein include crystalline forms, also known as polymorphs. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

The screening and characterization of the pharmaceutically acceptable salts, polymorphs and/or solvates may be accomplished using a variety of techniques including, but not limited to, thermal analysis, x-ray diffraction, spectroscopy, vapor sorption, and microscopy. Thermal analysis methods address thermo chemical degradation or thermo physical processes including, but not limited to, polymorphic transitions, and such methods are used to analyze the relationships between polymorphic forms, determine weight loss, to find the glass transition temperature, or for excipient compatibility studies. Such methods include, but are not limited to, Differential scanning calorimetry (DSC), Modulated Differential Scanning calorimetry (MDCS), Thermogravimetric analysis (TGA), and Thermogravi-metric and Infrared analysis (TG/IR). X-ray diffraction methods include, but are not limited to, single crystal and powder diffractometers and synchrotron sources. The various spectroscopic techniques used include, but are not limited to, Raman, FTIR, UV-VIS, and NMR (liquid and solid state). The various microscopy techniques include, but are not limited to, polarized light microscopy, Scanning Electron Microscopy (SEM) with Energy Dispersive X-Ray Analysis (EDX), Environmental Scanning Electron Microscopy with EDX (in gas or water vapor atmosphere), IR microscopy, and Raman microscopy.

Throughout the specification, groups and substituents thereof can be chosen by one skilled in the field to provide stable moieties and compounds.

Exemplary Preparation of Compounds

The synthesis of compounds described herein may be accomplished using means described in the chemical literature, using the methods described herein, or by a combination thereof.

Compounds described herein may be synthesized using standard synthetic techniques known to those of skill in the art or using methods known in the art in combination with methods described herein. In addition, solvents, temperatures and other reaction conditions presented herein may vary according to those of skill in the art.

The starting material used for the synthesis of the compounds described herein may be synthesized or can be obtained from commercial sources, such as, but not limited to, Aldrich Chemical Co. (Milwaukee, Wis.), or Sigma Chemical Co. (St. Louis, Mo.). The compounds described herein, and other related compounds having different substituents can be synthesized using techniques and materials described herein as well as those that are known to those of skill in the art, such as described, for example, in March, ADVANCED ORGANIC CHEMISTRY 4.sup.th Ed., (Wiley 1992); Carey and Sundberg, ADVANCED ORGANIC CHEMISTRY 4.sup.th Ed., Vols. A and B (Plenum 2000, 2001), and Green and Wuts, PROTECTIVE GROUPS IN ORGANIC SYNTHESIS 3.sup.rd Ed., (Wiley 1999), each of which is incorporated by reference herein in its entirety.

General methods for the preparation of compound as disclosed herein may be derived from known reactions in the field, and the reactions may be modified by the use of appropriate reagents and conditions, as would be recognized by the skilled person, for the introduction of the various moieties found in the formulae as provided herein. As a guide the following synthetic methods may be utilized.

In various embodiments, provided herein are compounds of the Formula I:

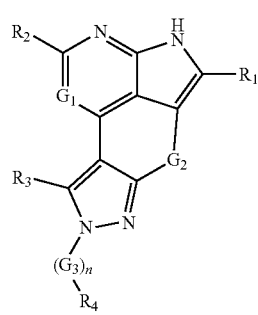

I or Formula II:

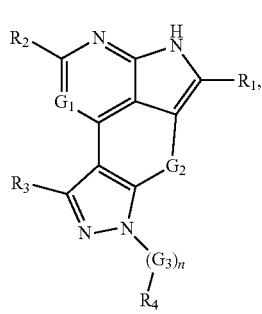

II or a pharmaceutically acceptable salt, solvate, analog, prodrug, isomer or tautomer thereof, wherein $R_1$, $R_2$, $R_3$, $R_4$, $G_1$, $G_2$, $G_3$, and n are as defined herein. These embodiments of the invention can be synthesized using methods known in the art. A specific synthetic method for preparing compounds of Formula I and Formula II is shown in Scheme A below:

formula (d) is well understood in the art. For example, see Nucleosides and Nucleotides, 1997, vol. 16, #3, pages 315-338, which is incorporated by reference herein in its entirety.

Step 4 depicts the reaction of a compound of formula (d) with a compound of formula (e) to give a compound of formula (f), where $R_1$, $R_2$, $R_3$, and $G_1$ are as desired in the

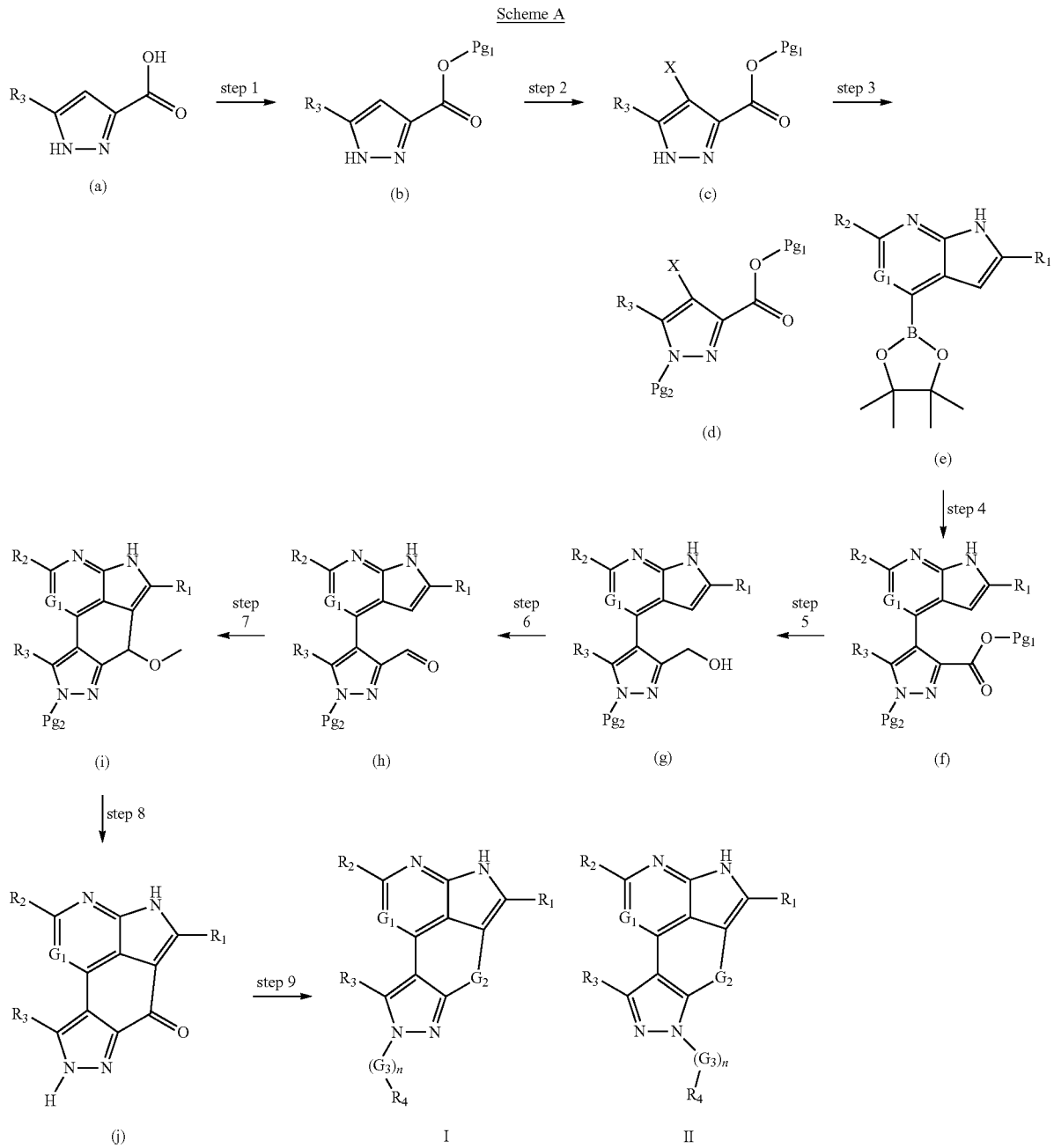

Scheme A

In Scheme A, Step 1 and Step 2 depict the reactions of a compound of formula (a), where $R_3$ is as desired in the final compound of the compound, with a compound of formula (b), where $R_3$ is as desired in the final compound $Pg_1$ is a $C_{1-4}$ alkyl alkly group, to give a compound of formula (c).

Step 3 depicts the reaction of an appropriate compound of formula (c) to give a compound of formula (d), in which $Pg_2$ is a protecting group. The synthesis of a compound of final compound of Formula I and $Pg_1$ and $Pg_2$ are protecting groups. Such Suzuki coupling reactions are well understood and appreciated.

Step 5 depicts the reduction of a compound of formula (f) to give a compound of formula (g). Such reduction reactions of esters to the corresponding alcohols are well understood and appreciated.

Step 6 depicts the oxidation of a compound of formula (g) to give a compound of formula (h). Such oxidation reactions of alcohols to the corresponding aldehydes are well understood and appreciated.

Step 7 depicts the cyclization reaction of a compound of formula (h) to give a compound of formula (i). Such cyclization reactions can be carried out under a variety of conditions.

Step 8 depicts the oxidation of a compound of formula (i) to give a compound of formula (j). Such deprotection reactions can be carried out under a variety of conditions.

Step 9 depicts the transformation of a compound of formula (j) to give a compound of Formula I or Formula II. As understood by those of skill in the art, such reactions can be carried out under a variety of conditions.

In various embodiments, provided herein are compounds of the Formula III:

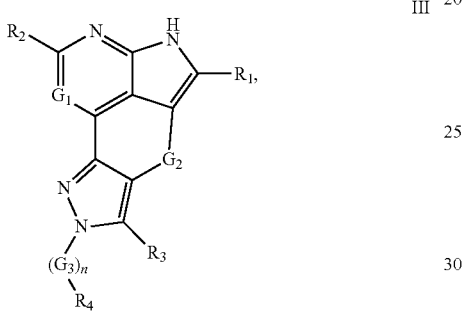

III or a pharmaceutically acceptable salt, solvate, analog, prodrug, isomer or tautomer thereof, wherein $R_1$, $R_2$, $R_3$, $R_4$, $G_1$, $G_2$, $G_3$, and n are as defined herein. These embodiments of the invention can be synthesized using methods known in the art. A specific synthetic method for preparing compounds of Formula III is shown in Scheme B below:

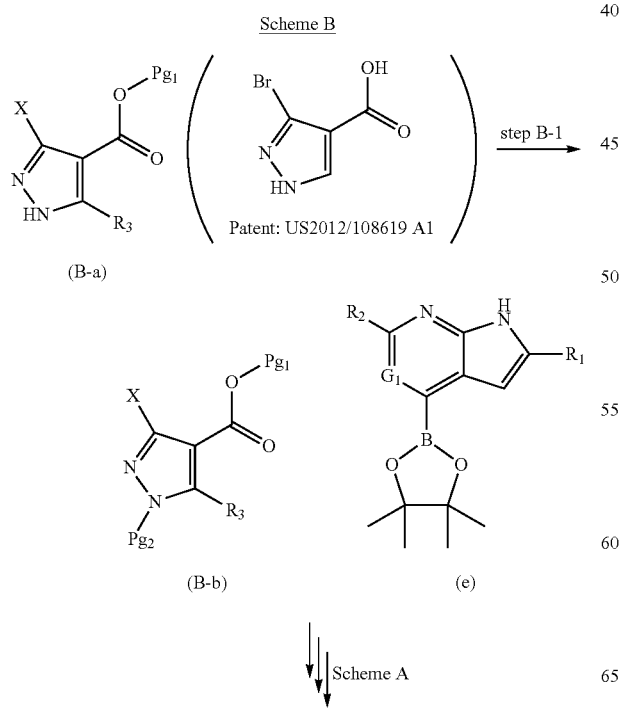

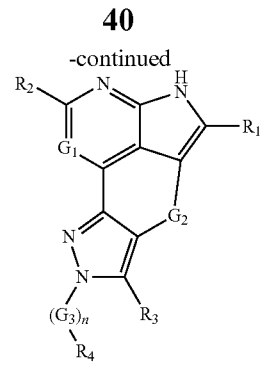

III

Scheme B depicts the transformation of an appropriate compound of formula (B-a) to give a compound of formula III, following chemistry analogous to that described above in Scheme A.

In various embodiments, provided herein are compounds of Formula Ia:

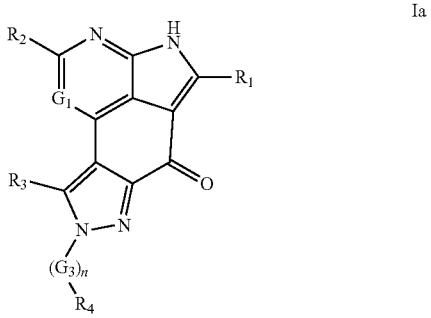

Ia and Formula IIa:

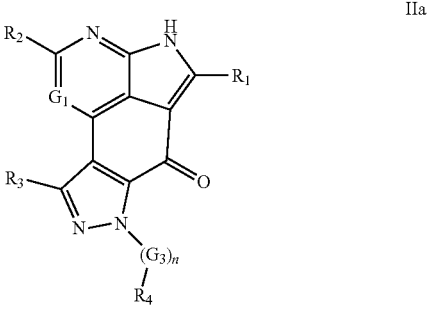

IIa or a pharmaceutically acceptable salt, solvate, analog, prodrug, isomer or tautomer thereof. These embodiments of the invention can be synthesized using methods known in the art. A specific synthetic method for preparing compounds of Formula Ia and Formula IIa is shown in Scheme A.

In various embodiments, provided herein are compounds of Formula IIIa:

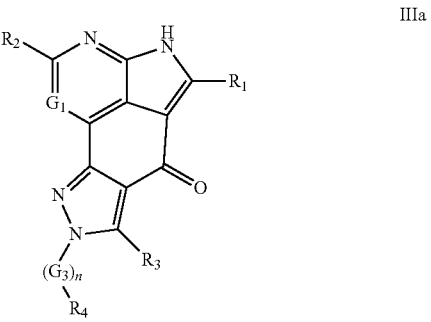

IIIa or a pharmaceutically acceptable salt, solvate, analog, prodrug, isomer or tautomer thereof. These embodiments of the invention can be synthesized using methods known in the art. A specific synthetic method for preparing compounds of Formula IIIa is shown in Scheme B.

In various embodiments, provided herein are compounds of Formula Ib:

and Formula IIb:

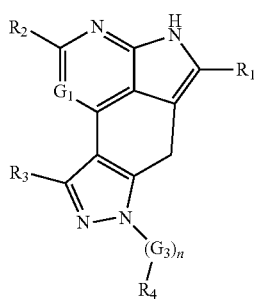

IIb or a pharmaceutically acceptable salt, solvate, analog, prodrug, isomer or tautomer thereof. These embodiments of the invention can be synthesized using methods known in the art. A specific synthetic method for preparing compounds of Formula Ib and Formula IIb is shown in Scheme C below:

Scheme C

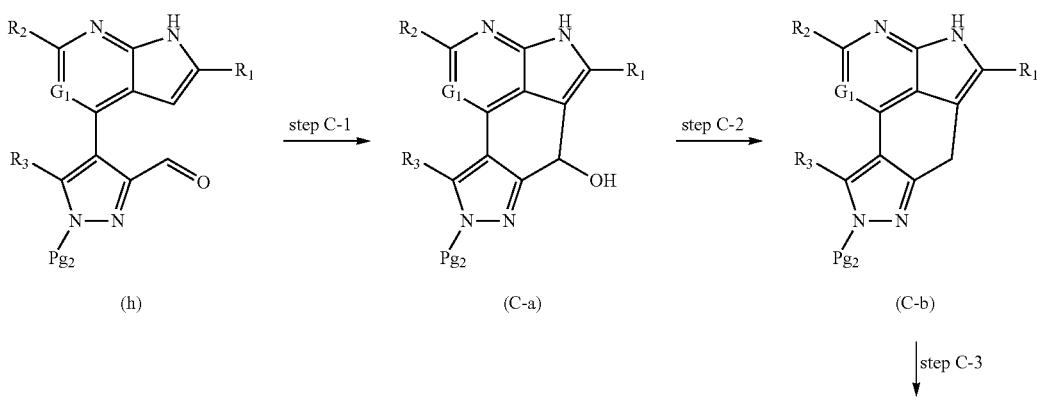

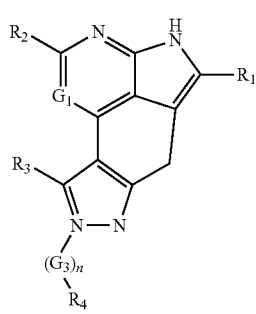

Ib

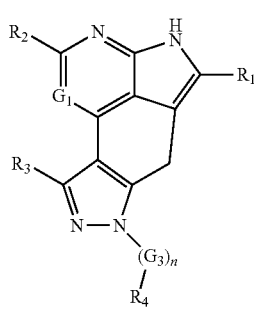

IIb

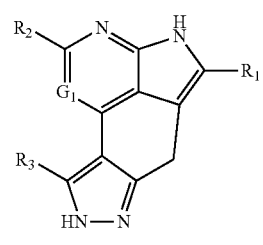

(C-c)

As illustrated in Scheme C, these compounds can be synthesized by using compounds having formula (h) as starting materials. Step C-1 depicts the cyclization reaction of a compound of formula (h) to give a compound of formula (C-a). Such cyclization reactions can be carried out under a variety of conditions known in the art.

Step C-2 depicts a reduction reaction of a compound of formula (C-a) to give a compound of formula (C-b). Such reduction reactions can be carried out under a variety of conditions such as Et$_3$SiH, TFA. Step C-3 depicts a reduction reaction of a compound of formula (C-b) to give a compound of formula (C-c). Step C-4 depicts the transformation of a compound of formula (C-c) to give a compound of Formula Ib or Formula IIb. Such reactions are carried out under a variety of conditions known in the art.

In various embodiments, provided herein are compounds of Formula IIIb:

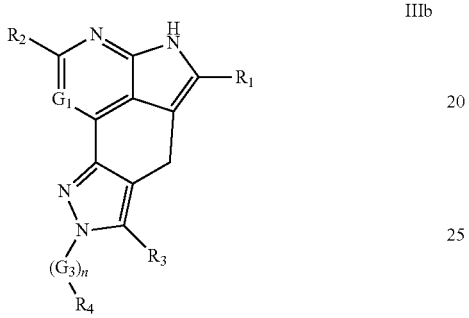

IIIb or a pharmaceutically acceptable salt, solvate, analog, prodrug, isomer or tautomer thereof. These embodiments of the invention can be synthesized using methods known in the art, as illustrated in Scheme B and C.

In various embodiments, provided herein are compounds of Formula Ic:

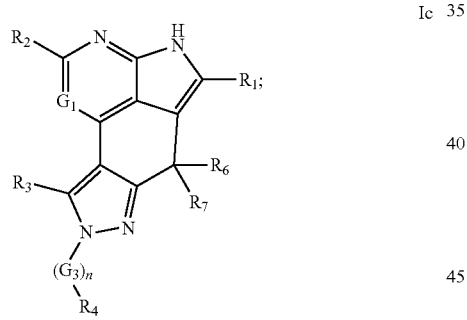

Ic

Formula IIc:

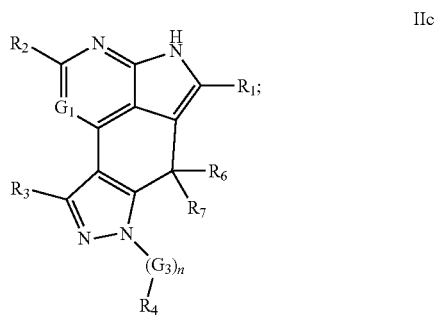

IIc and Formula IIIc:

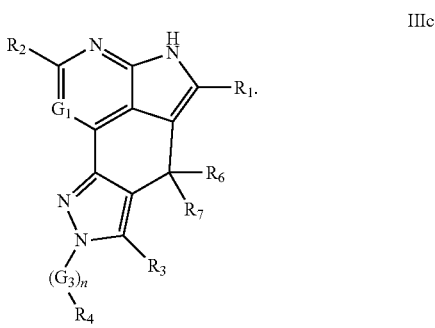

IIIc

These embodiments of the invention can be synthesized using methods known in the art. A specific synthetic method for preparing compounds of Formula Ic; Formula IIc and Formula IIIc is shown in Scheme D below:

Scheme D

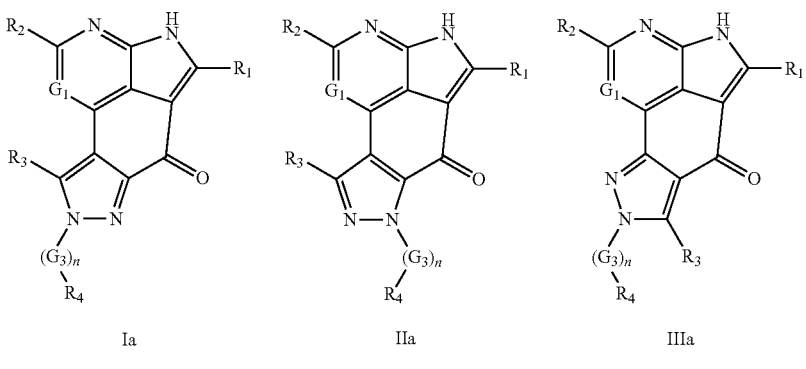

Ia    IIa    IIIa

↓ step D-1

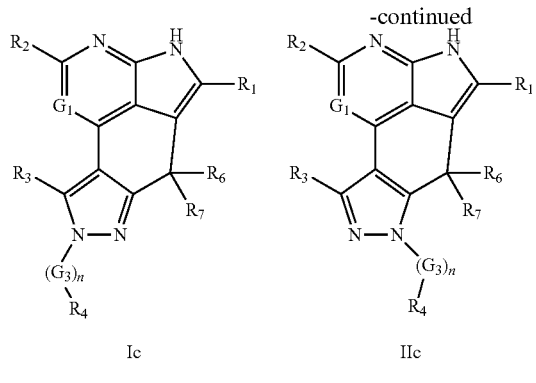

Ic    IIc    IIIc

Step D-1 depicts a nucleophilic addition reaction of a nucleophile, such as a Grignard reagent, onto a carbonyl. Such reduction reactions of ketones to the corresponding alcohols are well understood in the field.

In various embodiments, provided herein are compounds of Formula Id:

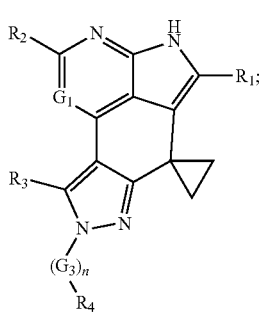

Id

Formula IId:

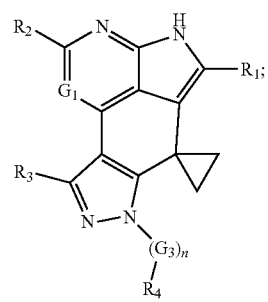

IId and Formula IIId:

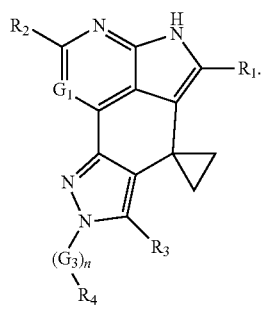

IIId

These embodiments of the invention can be synthesized using methods known in the art. A specific synthetic method for preparing compounds of Formula Id; Formula IId and Formula IIId is shown in Scheme E below:

Scheme E

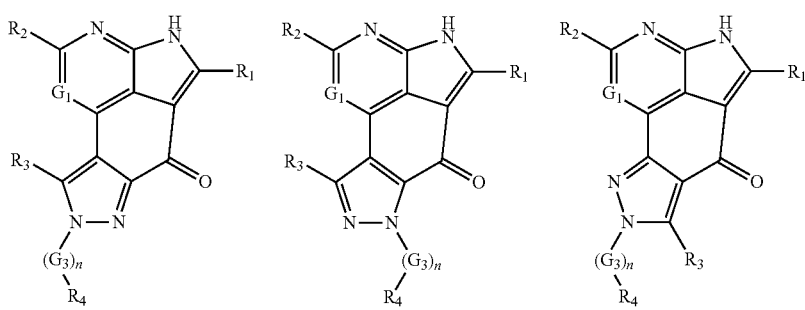

Ia    IIa    IIIa

↓ step E-1

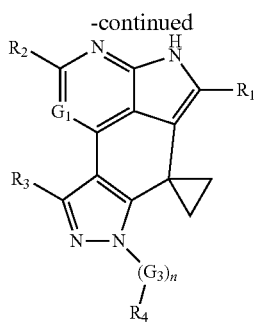
Id

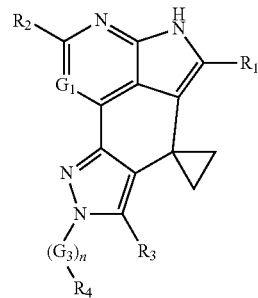
IId

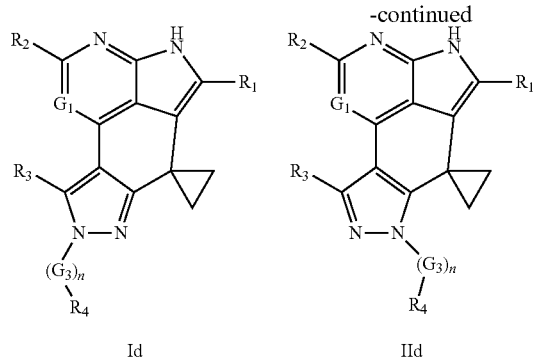
IIId

Step E-1 depicts a transformation of a ketone to the corresponding cyclopropyl group. Such reactions are well understood in the field. See, e.g., US Publication No. US2010/292128, which is incorporated by reference herein in its entirety.

In various embodiments, provided herein are compounds of Formula Ie:

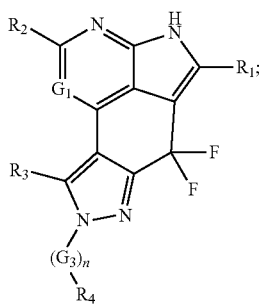
Ie

Formula IIe:

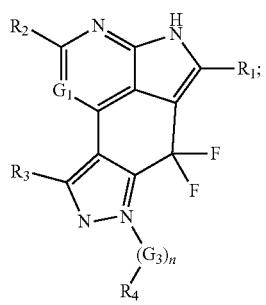
IIe and Formula IIIe:

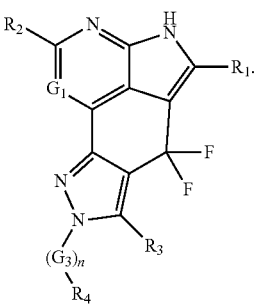
IIIe

These embodiments of the invention can be synthesized using methods known in the art. A specific synthetic method for preparing compounds of Formula Ie; Formula IIe and Formula IIIe is shown in Scheme F below:

Scheme F

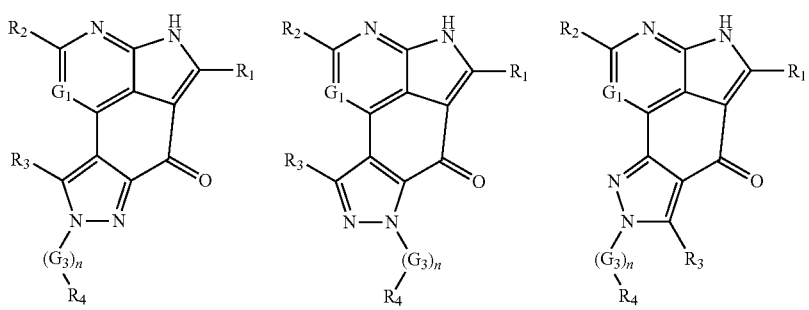

Ia     IIa     IIIa

↓ step F-1

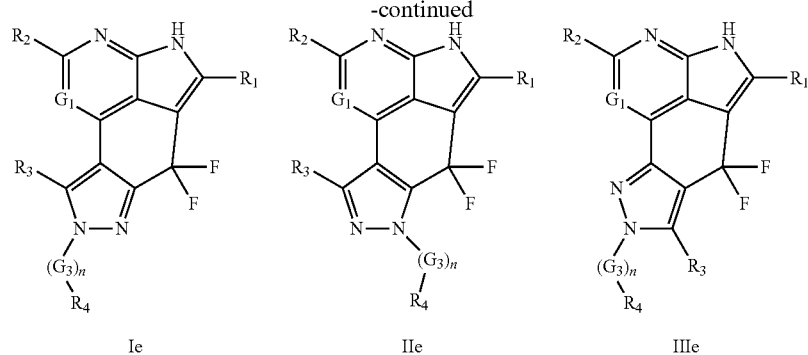

Ie IIe IIIe

Step F-1 depicts a transformation of a ketone to the corresponding difluoride. Such reactions are well understood in the field. See, e.g., U.S. Pat. No. 7,265,247, which is incorporated by reference herein in its entirety.

In various embodiments, provided herein are compounds of Formula If, Formula IIf, Formula IIIf, Formula If, Formula IIg and Formula IIIg. These embodiments of the invention can be synthesized using methods known in the art. A specific synthetic method for preparing these compounds is provided in Scheme G below.

Scheme G

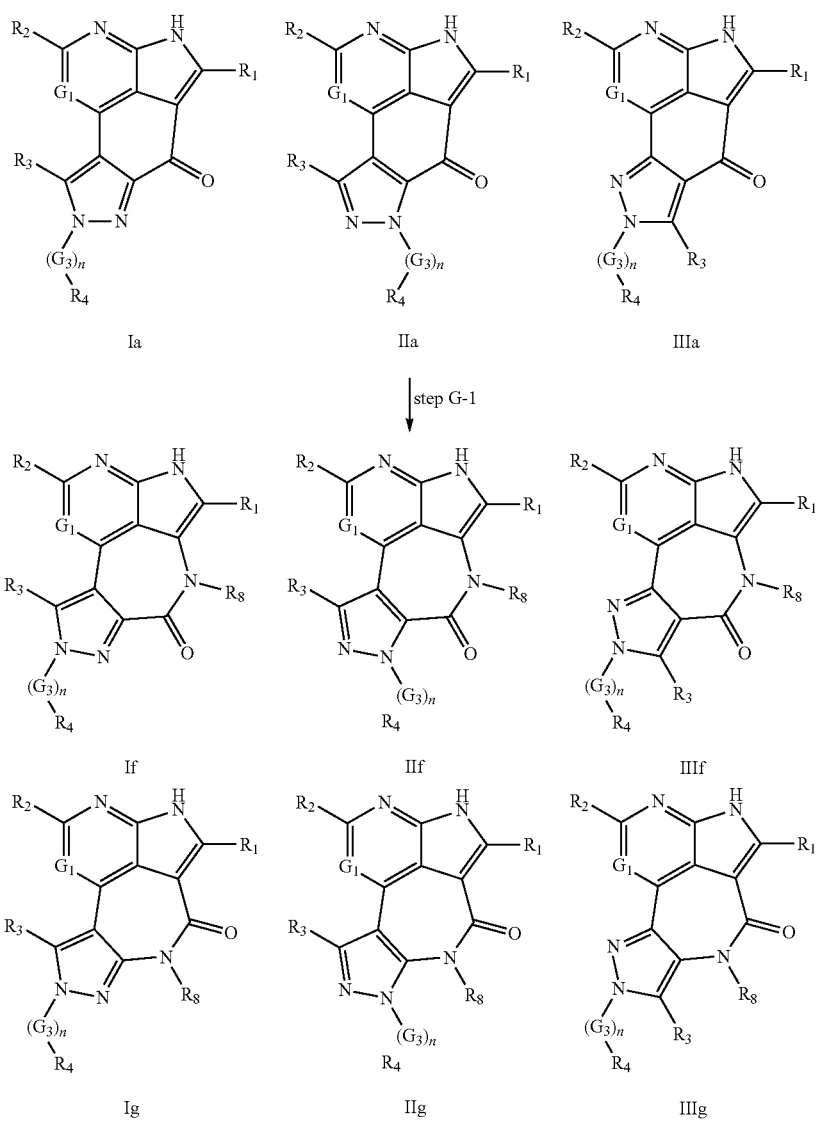

Step G-1 depicts a ring expansion reaction of a ketone to the corresponding lactam. Such reactions are well understood and appreciated. They can be carried out under a variety of conditions, such as Schmidt reaction or Beckmann rearrangement (via an oxime intermediate) conditions.

In various embodiments, provided herein are compounds of Formula Ih, Formula IIh, and Formula IIIb. These embodiments of the invention can be synthesized using methods known in the art. A specific synthetic method for preparing these compounds is provided in Scheme H below.

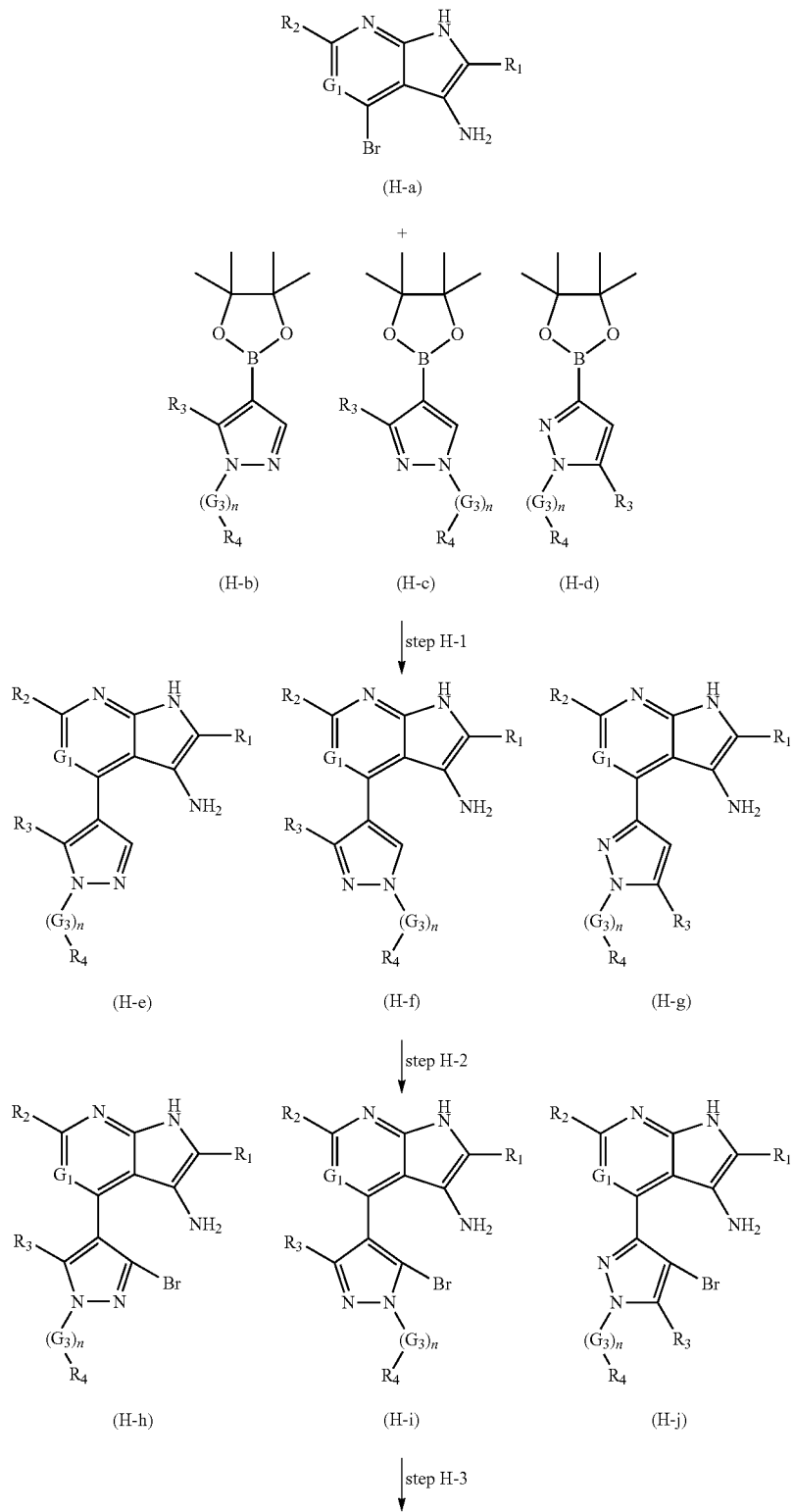

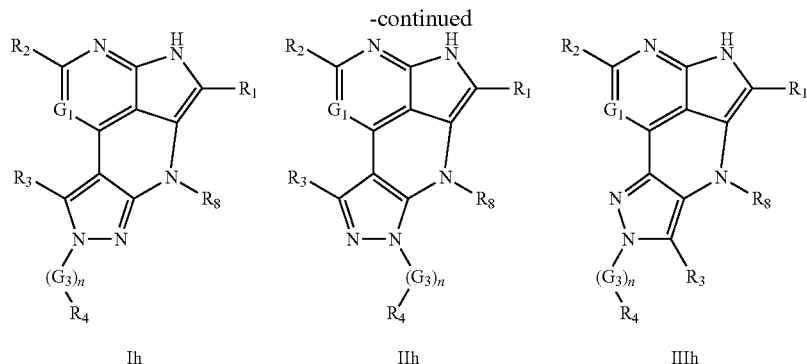

Step H-1 depicts a Suzuki coupling reaction between compounds having a formula (H-a) and (H-b), (H-c), (H-d) to give compounds having formula (H-e), (H-f), (H-g). Step H-2 depicts a bromination reaction. Such reactions are well understood in the field. Step 3 depicts a transition metal catalyzed C—N bond formation. Such reactions are well understood by those of skill in the art and can be carried out under a variety of conditions, such as the Buchwald-Hartwig amination conditions In various embodiments, provided herein are compounds of the Formula IV:

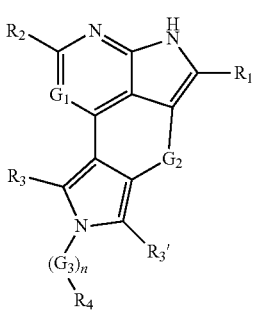

or Formula V:

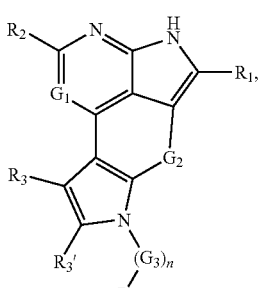

wherein $R_1$, $R_2$, $R_3$, $R_{3'}$, $R_4$, $G_1$, $G_2$, $G_3$, and n are as defined herein. These embodiments of the invention can be synthesized using methods known in the art. A specific synthetic method for preparing compounds of Formula IV and Formula V is shown in Scheme I below:

Scheme I

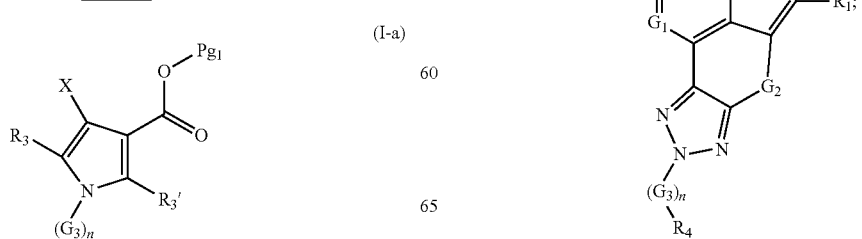

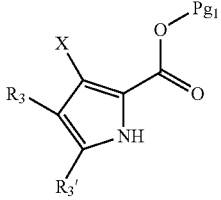

(I-b)

Scheme A

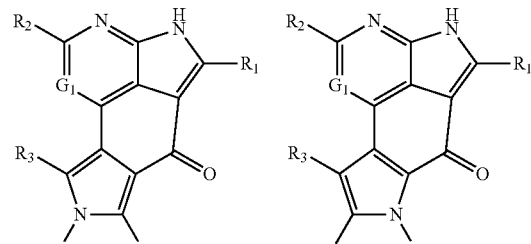

Scheme I depicts the transformation of a compound of Formula (I-a) or Formula (I-b) to give a compound of Formula IV or Formula V following similar chemistry depicted in Scheme A.

In various embodiments, provided herein are compounds of the Formula VI:

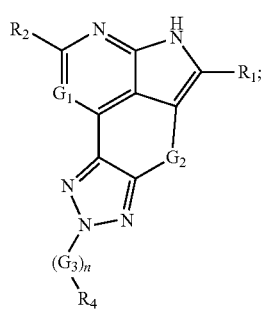

Formula VII:
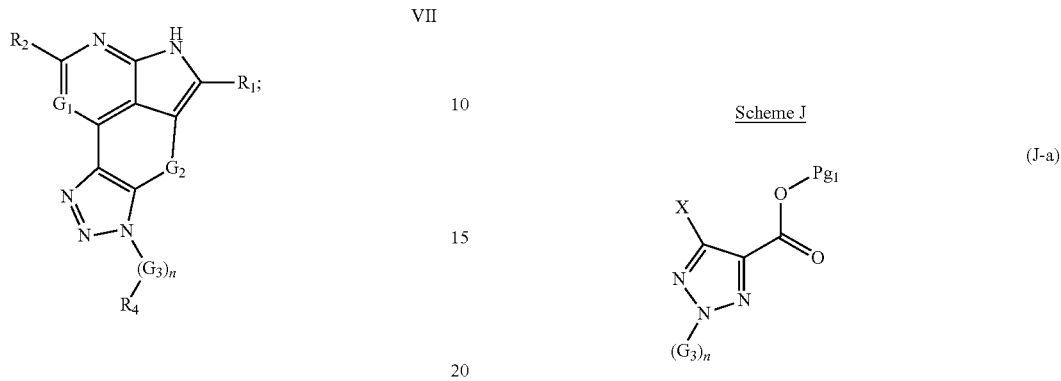
or Formula VIII
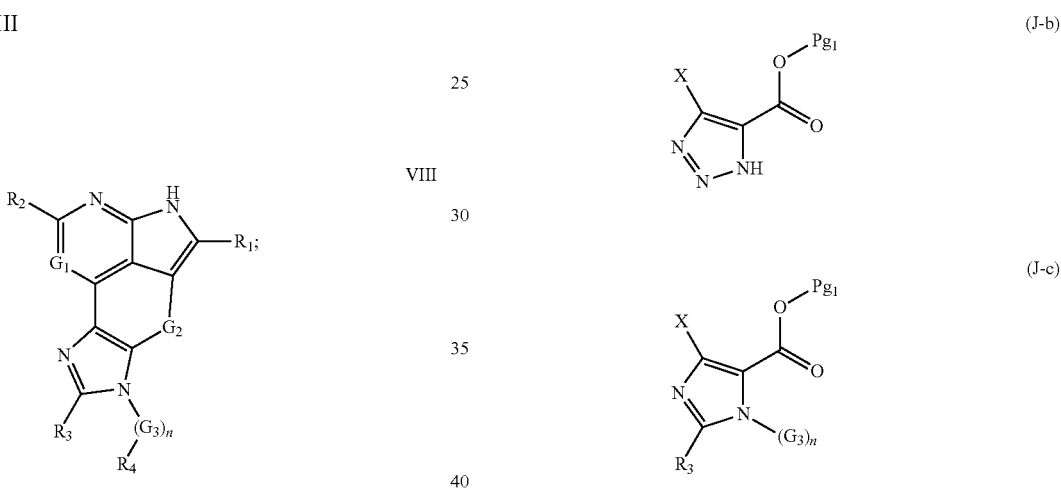
wherein $R_1$, $R_2$, $R_4$, $G_1$, $G_2$, $G_3$, and n are as defined herein. These embodiments of the invention can be synthesized using methods known in the art. A specific synthetic method for preparing compounds of Formula VI, Formula VII and Formula VIII is shown in Scheme J below:
Scheme J
Scheme A
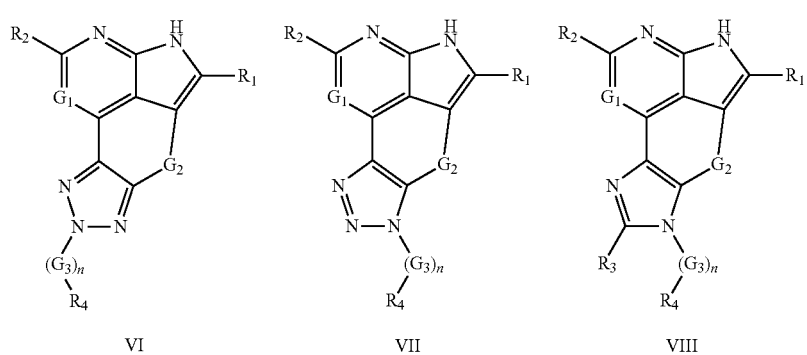

Scheme J depicts the transformation of a compound of Formula (J-a), Formula (J-b) or Formula (J-c) to give a compound of Formula VI, Formula VII or Formula VIII following similar chemistry depicted in Scheme A.

It will be recognized by one of ordinary skill in the art that the steps in Scheme A to I may be varied to provide compounds of Formula I, II, III, IV, V, VI, VII, VIII and Ia-h, IIa-h, IIIa-h. In particular, the order of the steps required to produce the compounds of Formula I, II, III, IV, V, VI, VII, VIII and Ia-h, IIa-h, IIIa-h is dependent upon the particular compound being synthesized, the starting compound, and the relative lability of the substituted moieties. For example, a compound of formula (i) can be converted to a compound of formula (j) in a two-step sequence: First, conversion of the —OMe group to —OH; and then the oxidation of the —OH group to a ketone. Also for example, the $Pg_2$ group of a compound of formula (d), (f), (g), (h), (i) can be replaced with the -$(G_3)_n$-$R_4$ group, which is desired in the final compound of Formula I, II, III, IV, V, VI, VII, VIII and Ia-h, IIa-h, IIIa-h.

It is also understood that some compounds of Formula I, II, III, IV, V, VI, VII, VIII and Ia-h, IIa-h, IIIa-h may be elaborated to other compounds of Formula I, II, III, IV, V, VI, VII, VIII and Ia-h, IIa-h, IIIa-h, in additional steps not shown. For example, a compound of Formula I, II, III in which $G_2$ is a C═O, can undergo addition reaction by a nucleophile (such as a Grignard reagent) to give a tertiary alcohol, or be converted to a germinal dihalide. Compounds of Formula I, II, III, IV, V, VI, VII, VIII and Ia-h, IIa-h, IIIa-h may be elaborated in a variety of other ways. Such reactions include hydrolysis, oxidation, reduction, alkylation, amidations, sulfonations, alkynations, alkyenations, and the like. Also, in an optional step (not shown) the compounds of Formula I, II, III, IV, V, VI, VII, VIII and Ia-h, IIa-h, IIIa-h can be converted to pharmaceutically acceptable salts by methods well known and appreciated in the art.

Exemplary Compounds

Specific non-limiting examples of compounds falling within Formula IV are:

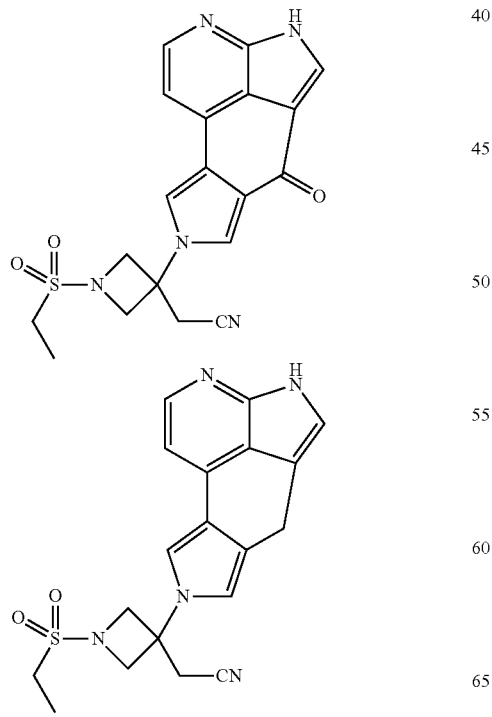

-continued

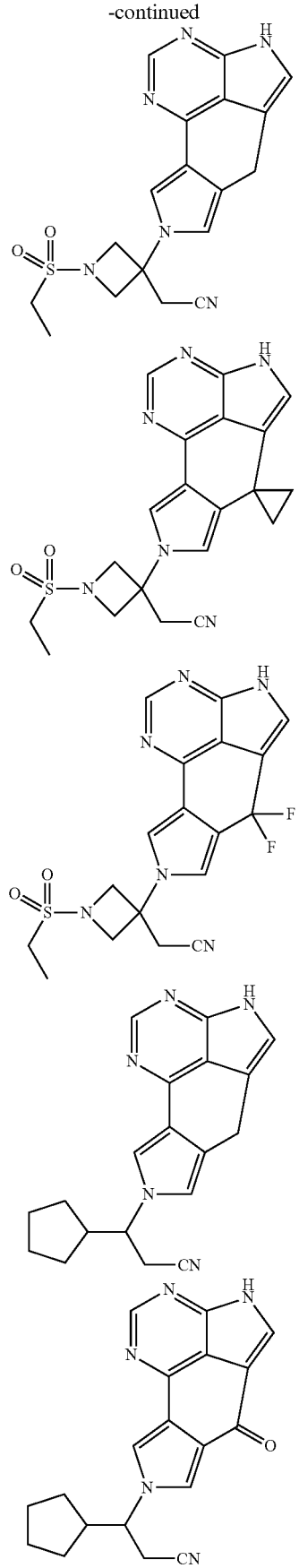

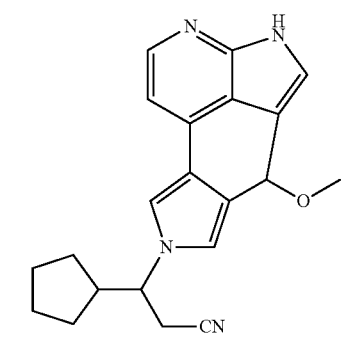
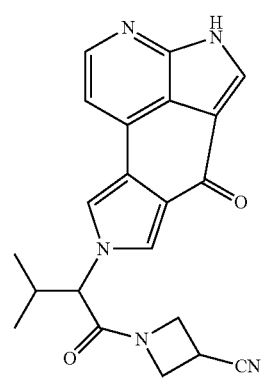
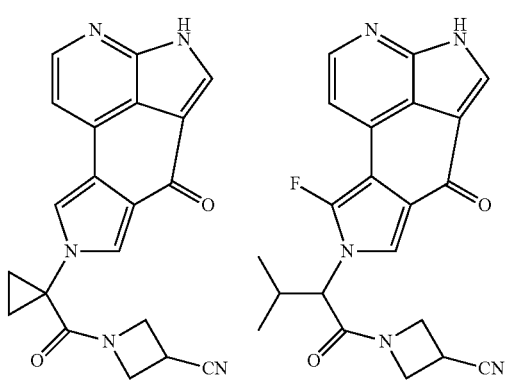
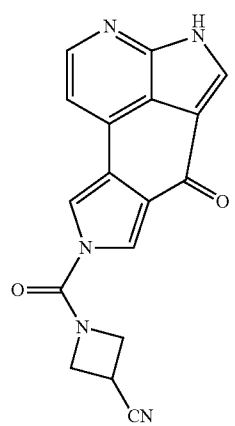
Specific non-limiting examples of compounds falling within Formula V are:
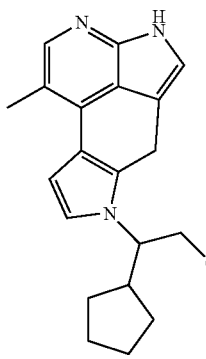 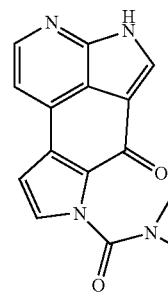
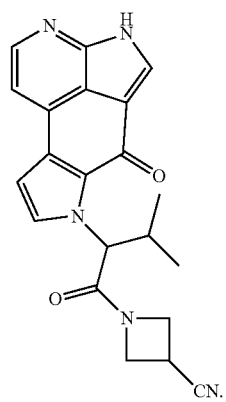
Specific non-limiting examples of compounds falling within Formula VI are:
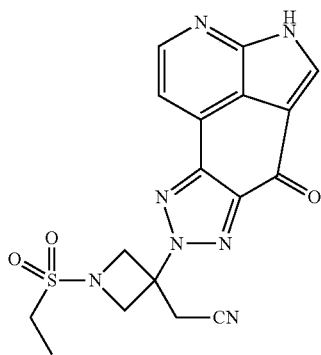
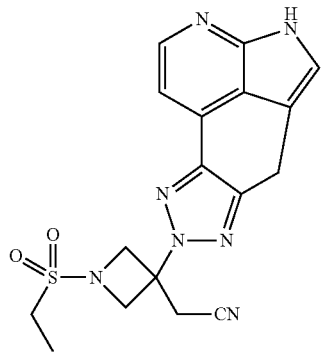

61
-continued
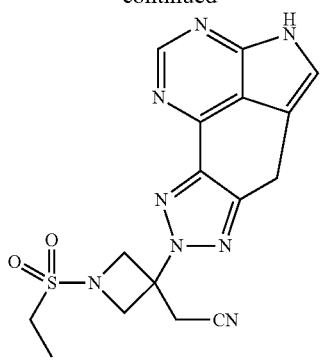
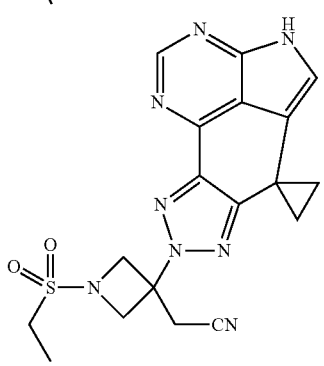
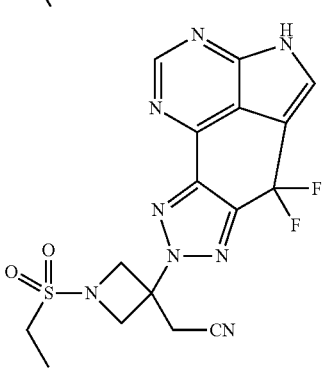
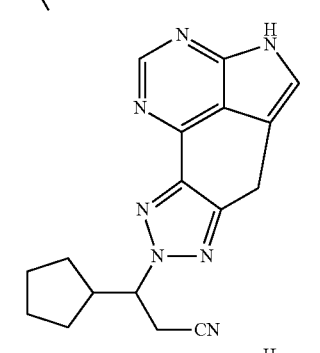
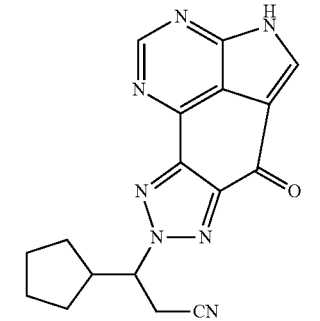
62
-continued
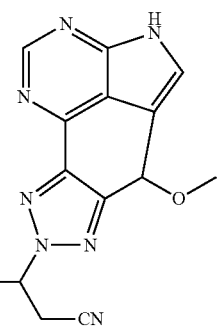
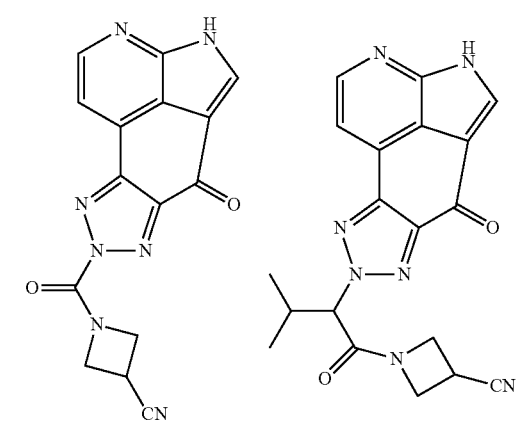
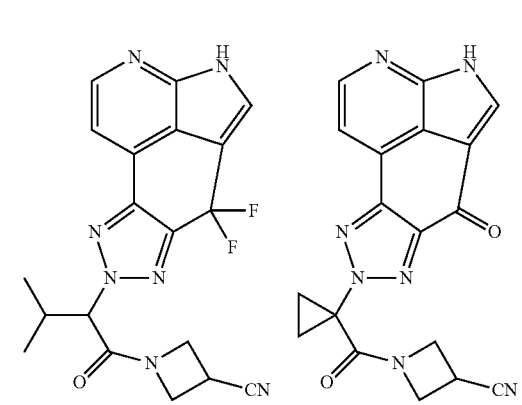
Specific non-limiting examples of compounds falling within Formula VII are:
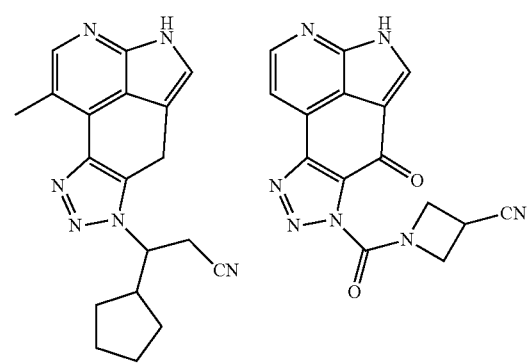

-continued
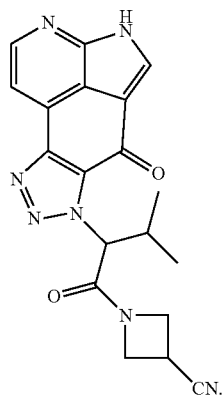
Specific non-limiting examples of compounds falling within Formula VIII are:
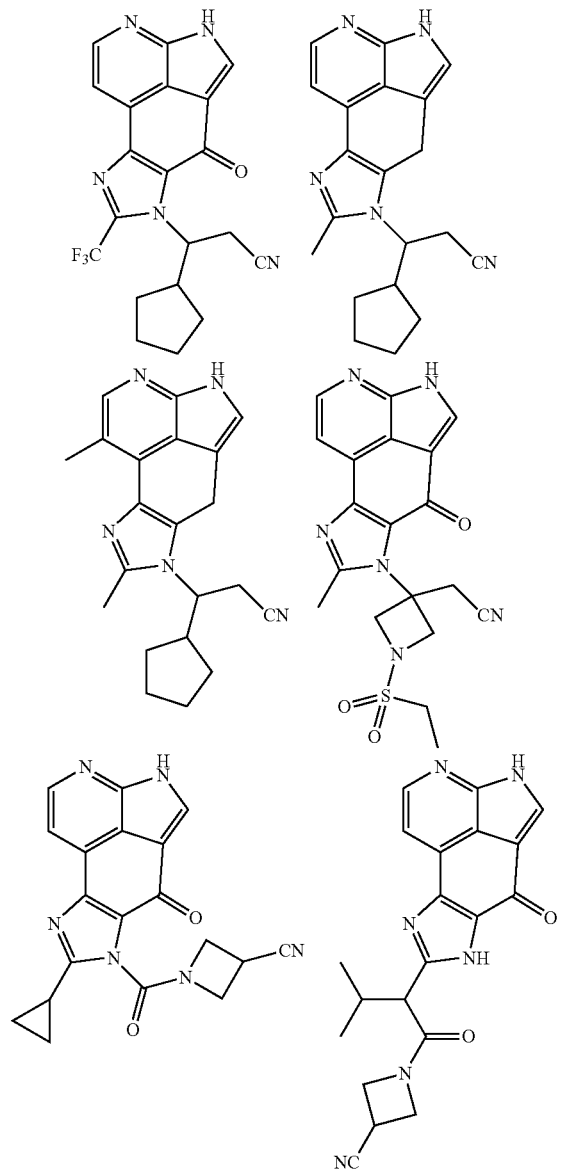
-continued
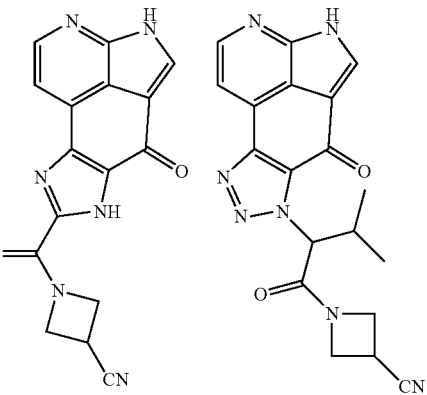
In some specific embodiments, provided herein are compounds of Formula Ia:
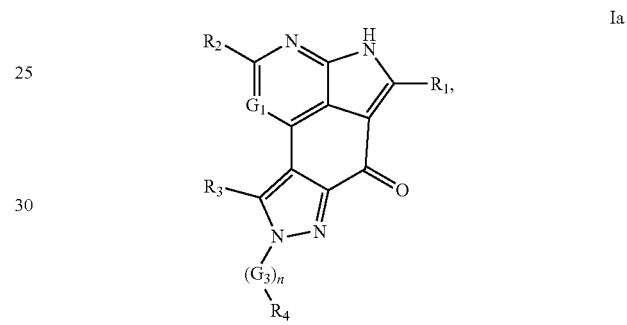
wherein $R_1$, $R_2$, $R_3$, $R_4$, $G_1$, $G_3$, and n are as defined herein. Specific non-limiting examples of compounds falling within Formula Ia are:
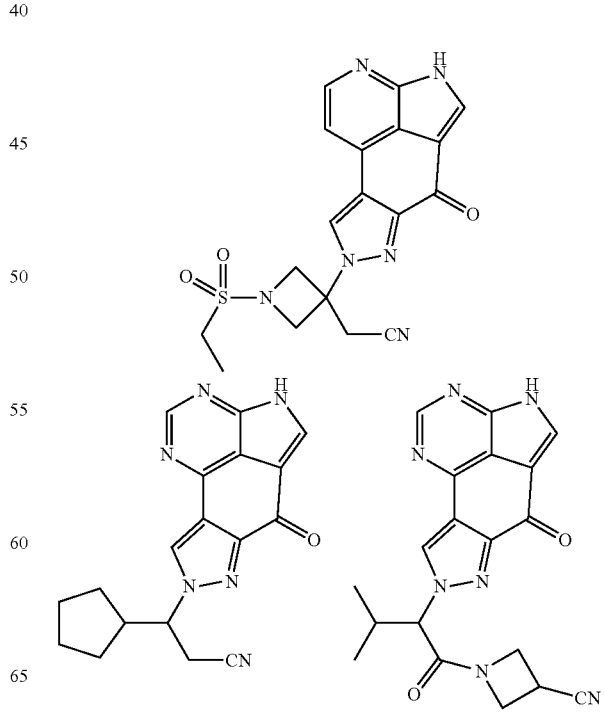

-continued

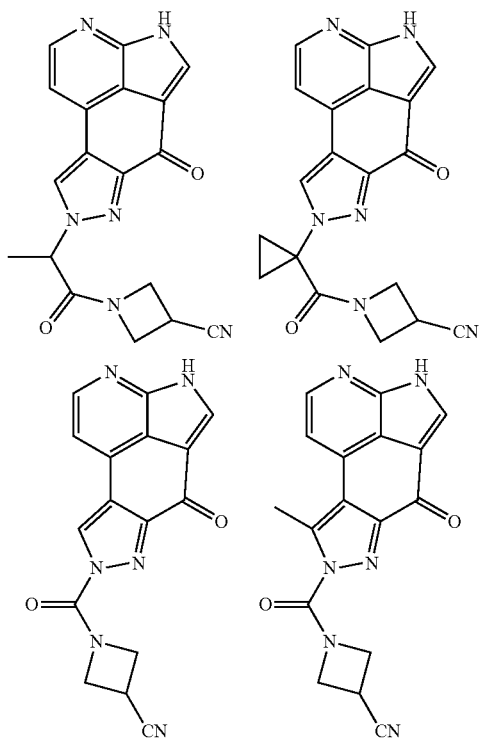

In some specific embodiments, provided herein are compounds of Formula Ib:

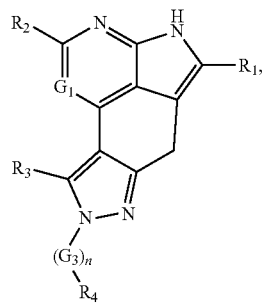
Ib wherein $R_1$, $R_2$, $R_3$, $R_4$, $G_1$, $G_3$, and n are as defined herein. Specific non-limiting examples of compounds falling within Formula Ib are:

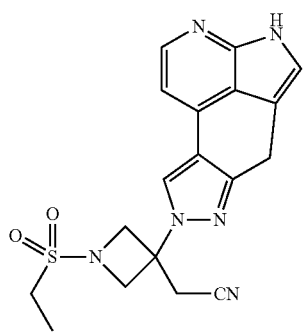

-continued

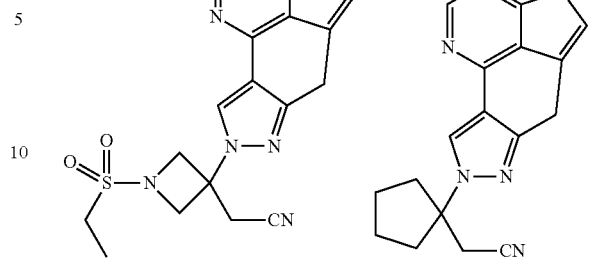

In some specific embodiments, provided herein are compounds of Formula Ic:

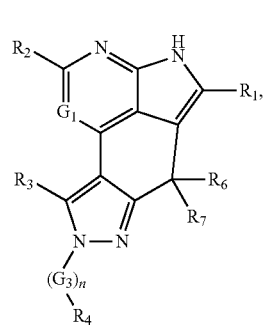
Ic wherein $R_1$, $R_2$, $R_3$, $R_4$, $R_6$, $R_7$, $G_1$, $G_3$, and n are as defined herein. Specific non-limiting examples of compounds falling within Formula Ic are:

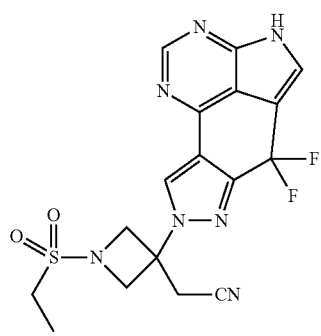

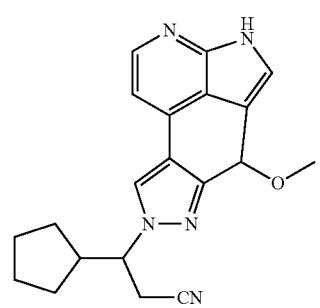

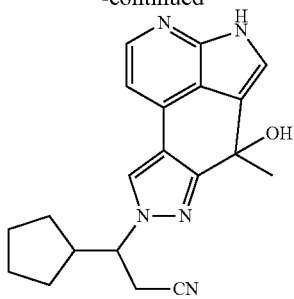

In some specific embodiments, provided herein are compounds of Formula Id:

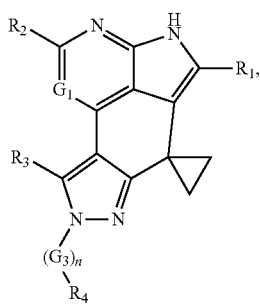

wherein $R_1$, $R_2$, $R_3$, $R_4$, $G_1$, $G_3$, and n are as defined herein. Specific non-limiting examples of compounds falling within Formula Id are:

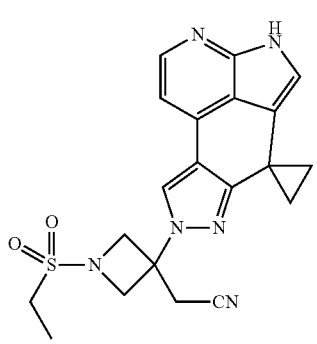

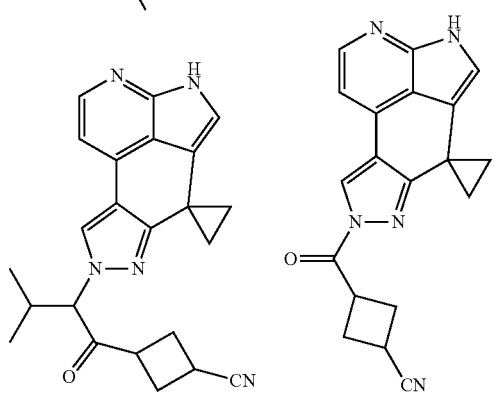

In some specific embodiments, provided herein are compounds of Formula Ie:

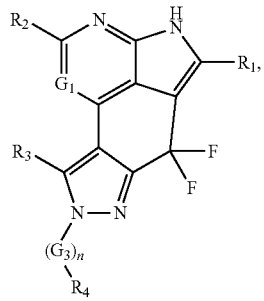

wherein $R_1$, $R_2$, $R_3$, $R_4$, $G_1$, $G_3$, and n are as defined herein.

In some specific embodiments, provided herein are compounds of Formula If:

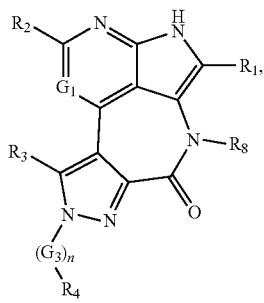

wherein $R_1$, $R_2$, $R_3$, $R_4$, $R_8$, $G_1$, $G_3$, and n are as defined herein. A specific non-limiting examples of a compound that falls within Formula If is:

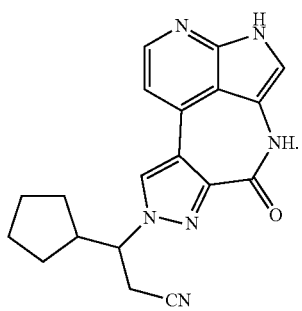 [SMILES: N#CCC(C1CCCC1)n1cc2c(n1)C(=O)Nc1c[nH]c3nccc-2c13]

In some specific embodiments, provided herein are compounds of Formula Ig:

wherein $R_1$, $R_2$, $R_3$, $R_4$, $R_8$, $G_1$, $G_3$, and n are as defined herein. A specific non-limiting example of a compound falling within Formula Ig is:

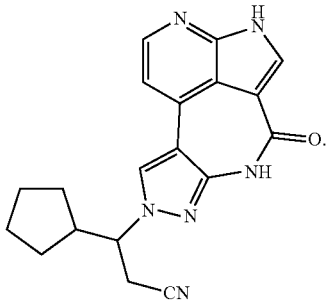 [SMILES: N#CCC(C1CCCC1)n1cc2c(n1)NC(=O)c1c[nH]c3nccc-2c13]

In some specific embodiments, provided herein are compounds of Formula Ih:

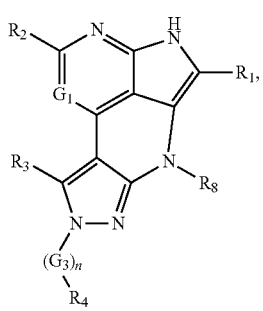

Ih wherein $R_1$, $R_2$, $R_3$, $R_4$, $R_8$, $G_1$, $G_3$, and n are as defined herein.

In some specific embodiments, provided herein are compounds of Formula IIa:

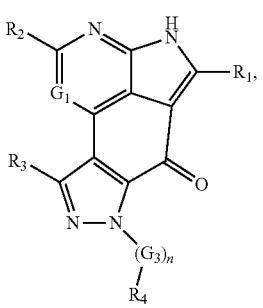

IIa wherein $R_1$, $R_2$, $R_3$, $R_4$, $G_1$, $G_3$, and n are as defined herein. Specific non-limiting examples of compounds falling within Formula IIa are:

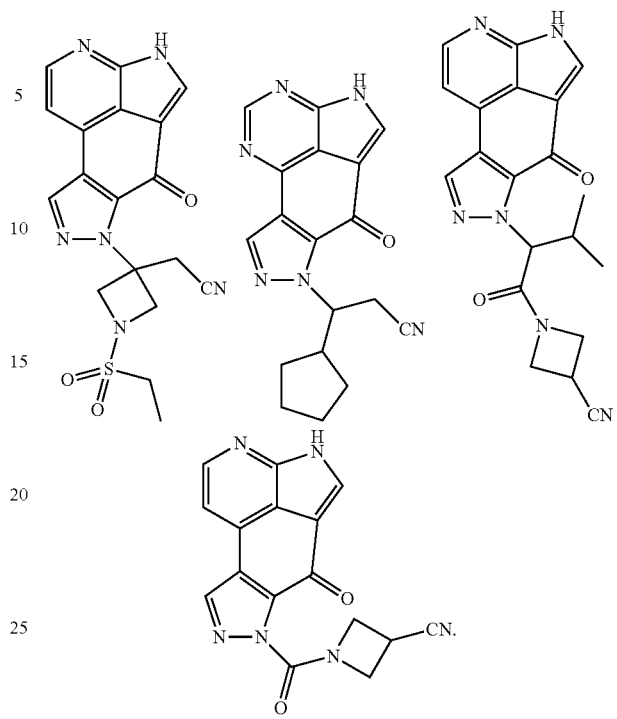

In some specific embodiments, provided herein are compounds of Formula IIb:

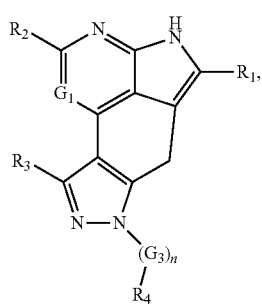

IIb wherein $R_1$, $R_2$, $R_3$, $R_4$, $G_1$, $G_3$, and n are as defined herein. Specific non-limiting examples of compounds falling within Formula IIb are:

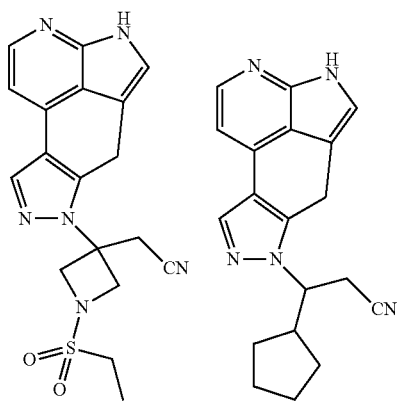

-continued

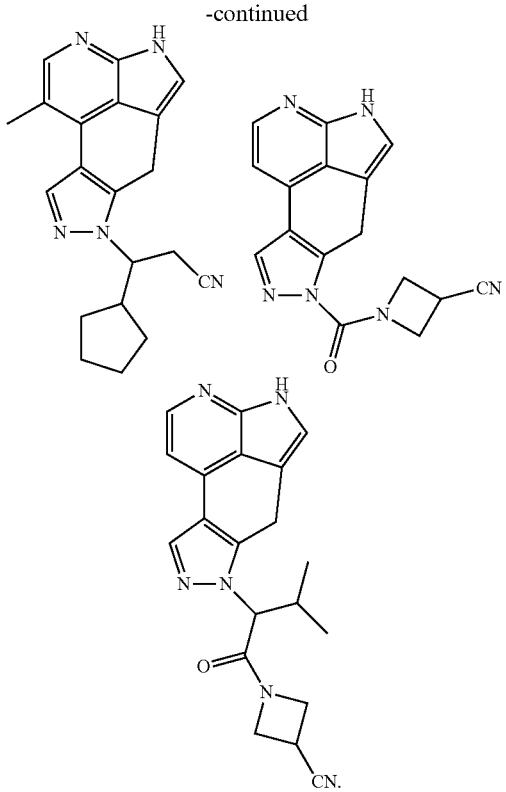

In some specific embodiments, provided herein are compounds of Formula IIc:

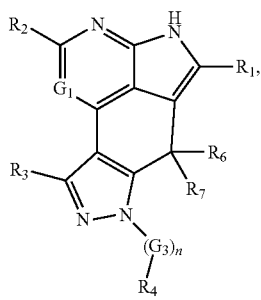

wherein $R_1$, $R_2$, $R_3$, $R_4$, $R_6$, $R_7$, $G_1$, $G_3$, and n are as defined herein.

In some specific embodiments, provided herein are compounds of Formula IId:

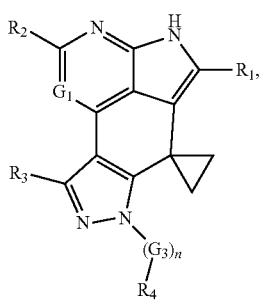

wherein $R_1$, $R_2$, $R_3$, $R_4$, $G_1$, $G_3$, and n are as defined herein. A specific non-limiting example of a compound falling within Formula IId is:

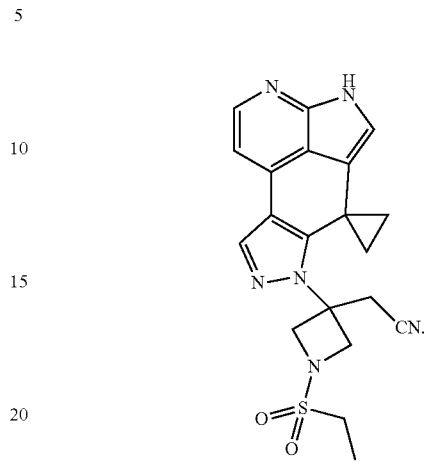

In some specific embodiments, provided herein are compounds of Formula IIe:

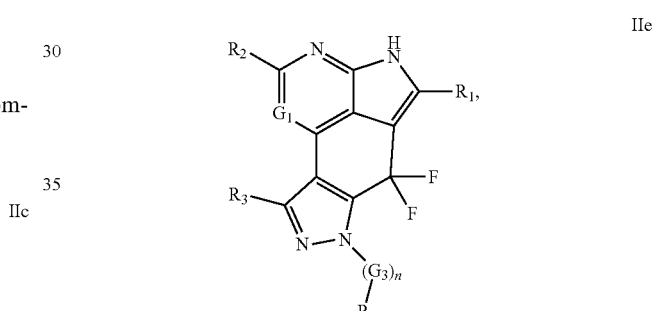

wherein $R_1$, $R_2$, $R_3$, $R_4$, $G_1$, $G_3$, and n are as defined herein. Specific non-limiting examples of compounds falling within Formula IIe are:

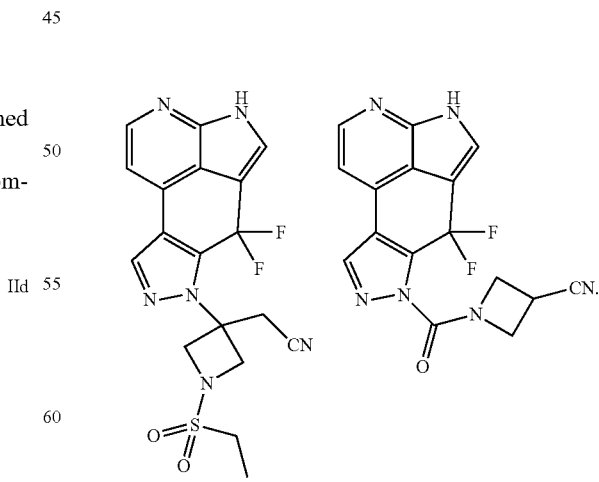

In some specific embodiments, provided herein are compounds of Formula IIf:

IIf

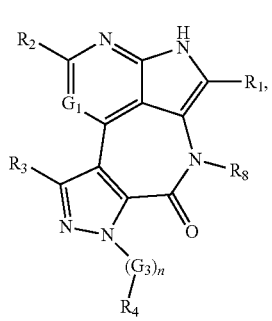

wherein $R_1$, $R_2$, $R_3$, $R_4$, $R_8$, $G_1$, $G_3$, and n are as defined herein. A specific non-limiting example of a compound falling within Formula IIf is:

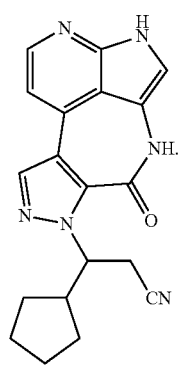 [SMILES: N#CCC(C1CCCC1)n1ncc2c1C(=O)Nc1c[nH]c3nccc-2c13]

In some specific embodiments, provided herein are compounds of Formula IIg:

IIg

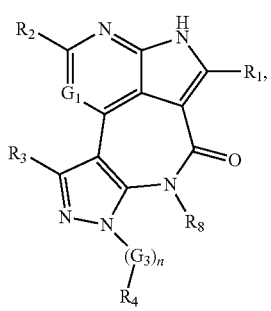

wherein $R_1$, $R_2$, $R_3$, $R_4$, $R_8$, $G_1$, $G_3$, and n are as defined herein. A specific non-limiting example of a compound falling within Formula IIg is:

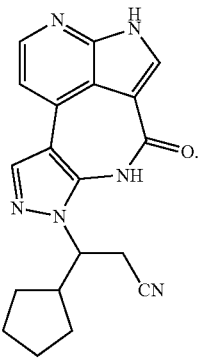 [SMILES: N#CCC(C1CCCC1)n1ncc2c1NC(=O)c1c[nH]c3nccc-2c13]

In some specific embodiments, provided herein are compounds of Formula IIh:

IIh

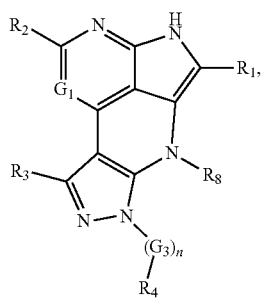

wherein $R_1$, $R_2$, $R_3$, $R_4$, $R_8$, $G_1$, $G_3$, and n are as defined herein.

In some specific embodiments, provided herein are compounds of Formula IIIa:

IIIa

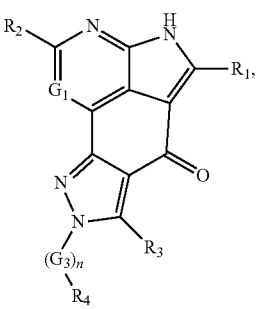

wherein $R_1$, $R_2$, $R_3$, $R_4$, $G_1$, $G_3$, and n are as defined herein. Specific non-limiting examples of compounds falling within Formula IIIa are:

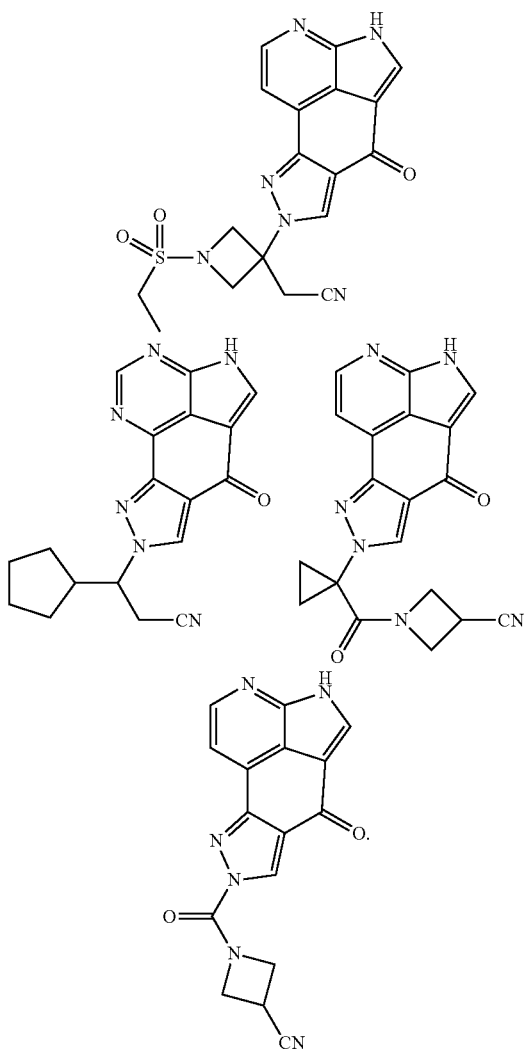

In some specific embodiments, provided herein are compounds of Formula IIIb:

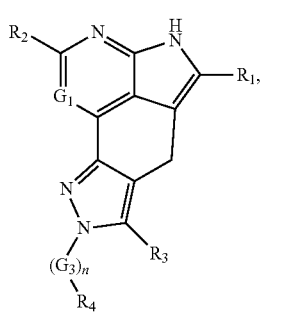

wherein $R_1$, $R_2$, $R_3$, $R_4$, $G_1$, $G_3$, and n are as defined herein. Specific non-limiting examples of compounds falling within Formula IIIb are:

In some specific embodiments, provided herein are compounds of Formula IIIc:

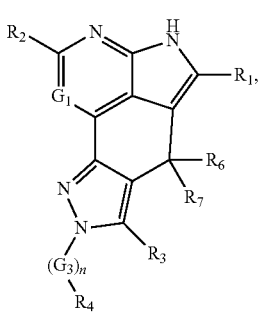

wherein $R_1$, $R_2$, $R_3$, $R_4$, $R_6$, $R_7$, $G_1$, $G_3$, and n are as defined herein. Specific non-limiting examples of compounds falling within Formula IIIc are:

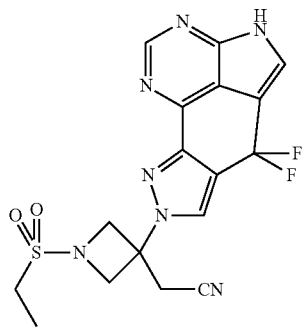

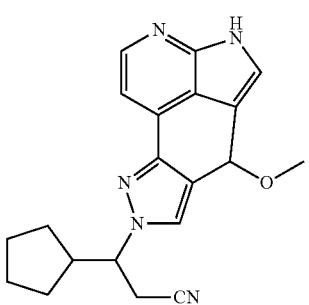

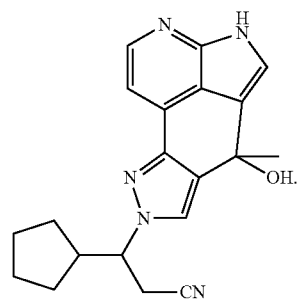

In some specific embodiments, provided herein are compounds of Formula IIId:

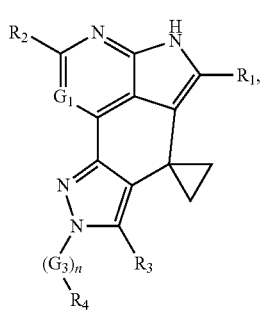

IIId wherein $R_1$, $R_2$, $R_3$, $R_4$, $G_1$, $G_3$, and n are as defined herein. A specific non-limiting example of a compound falling within Formula IIId is:

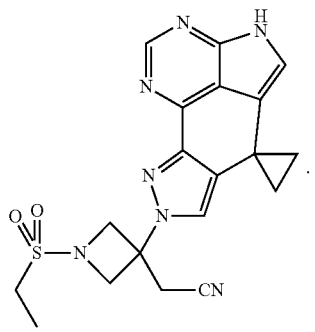 [SMILES: CCS(=O)(=O)N1CC(CC#N)(n2cc3c(n2)-c2ncnc4[nH]cc(c24)C32CC2)C1]

In some specific embodiments, provided herein are compounds of Formula IIIe:

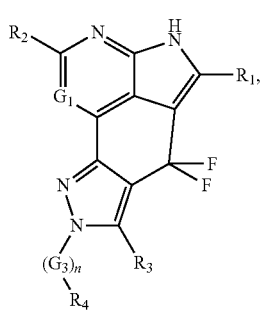

IIIe wherein $R_1$, $R_2$, $R_3$, $R_4$, $G_1$, $G_3$, and n are as defined herein.

In some specific embodiments, provided herein are compounds of Formula IIIf:

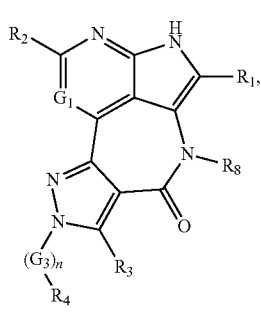

IIIf wherein $R_1$, $R_2$, $R_3$, $R_4$, $R_8$, $G_1$, $G_3$, and n are as defined herein. A specific non-limiting example of a compound falling within Formula IIIf is:

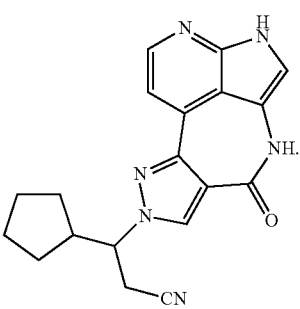 [SMILES: N#CCC(C1CCCC1)n1cc2c(n1)-c1ccnc3[nH]cc(c13)NC2=O]

In some specific embodiments, provided herein are compounds of Formula IIIg:

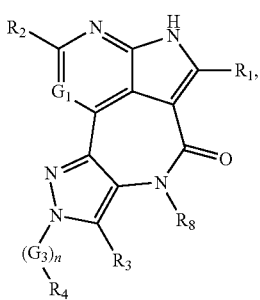

IIIg wherein $R_1$, $R_2$, $R_3$, $R_4$, $R_8$, $G_1$, $G_3$, and n are IIIg are as defined herein. A specific non-limiting example of a compound falling within Formula IIIg is:

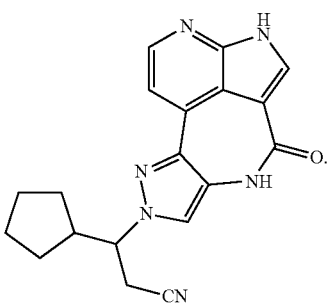 [SMILES: N#CCC(C1CCCC1)n1cc2c(n1)-c1ccnc3[nH]cc(c13)C(=O)N2]

In some specific embodiments, provided herein are compounds of Formula IIIh:

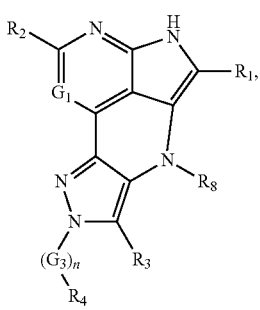

IIIh wherein $R_1$, $R_2$, $R_3$, $R_4$, $R_8$, $G_1$, $G_3$, and n are as defined herein.

Having now generally described the invention, the same will be more readily understood through reference to the following examples which are provided by way of illustration, and are not intended to be limiting of the present invention, unless specified.

EXAMPLES

Preparation A: ethyl 1-(oxan-2-yl)-4-{1H-pyrrolo[2,3-b]pyridin-4-yl}-1H-pyrazole-3-carboxylate

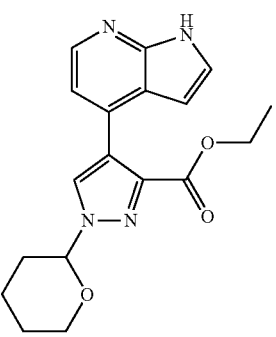 [SMILES: CCOC(=O)c1nn(C2CCCCO2)cc1-c1ccnc2[nH]ccc12]

Ethyl 4-bromo-1-(oxan-2-yl)-1H-pyrazole-3-carboxylate (as a mixture of regioisomers of the tetrahydropyran group at the nitrogen atoms of the pyrazole) (7.9 g, 26.23 mmol), 4-(tetramethyl-1,3,2-dioxaborolan-2-yl)-1H-pyrrolo[2,3-b]pyridine (6.4 g, 26.23 mmol), and Pd(PPh$_3$)$_4$ (1.8 g, 1.57 mmol) were taken up in a degassed DMF (100 mL) and NaHCO$_3$ (saturated, 50 mL) under an atmosphere of nitrogen.

The resulting mixture was stirred at 100° C. for 5 hours, cooled to room temperature and filtered through a thin pad of Celite (eluting with ethyl acetate). The organic layer was washed with water, brine, dried over Na$_2$SO$_4$, filtered and concentrated under vacuum. The residue was purified by flash chromatography (eluting with petroleum ether: ethyl acetate=2:1) to give 7.8 g of the title compound as a yellow solid. [M+H] found 341.

Preparation B: [1-(oxan-2-yl)-4-{1H-pyrrolo[2,3-b]pyridin-4-yl}-1H-pyrazol-3-yl]methanol

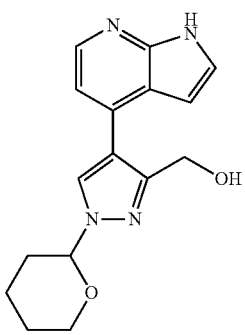 [SMILES: OCc1nn(C2CCCCO2)cc1-c1ccnc2[nH]ccc12]

To a stirred solution of ethyl 1-(oxan-2-yl)-4-{1H-pyrrolo[2,3-b]pyridin-4-yl}-1H-pyrazole-3-carboxylate (7.8 g, 22.94 mmol) in THF (100 mL), was added LiALH$_4$ (3 g, 70 mmol) in three portions at 0° C. The resulting mixture was stirred at room temperature for overnight. When the reaction was deemed complete, it was quenched by water (3 mL), extracted with ethyl acetate. The combined organic layer was dried ove Na₂SO₄, filtered and concentrated in vacuo to give 5.5 g of the title compound as an off-white solid. [M+H] found 299.

Preparation C: 1-(oxan-2-yl)-4-{1H-pyrrolo[2,3-b]pyridin-4-yl}-1H-pyrazole-3-carbaldehyde

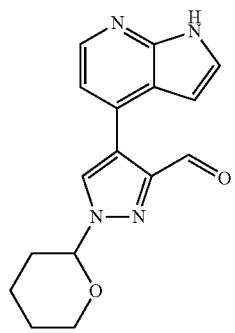 [SMILES: O=Cc1nn(C2CCCCO2)cc1-c1ccnc2[nH]ccc12]

To a stirred solution of [1-(oxan-2-yl)-4-{1H-pyrrolo[2,3-b]pyridin-4-yl}-1H-pyrazol-3-yl]methanol (5.5 g, 18.46 mmol) in dichloromethane (40 mL) was added the Dess-Martin reagent (11.7 g, 27.68 mmol). The reaction mixture was stirred at room temperature for three hours. When TLC showed completion of reaction, it was quenched with aqueous NaHCO₃ (saturated, 100 mL) and extracted with ethyl acetate.

The combined organic layer was washed with brine, dried over Na₂SO₄, and concentrated to give a crude product. It was purified by column chromatography (eluting with DCM:MeOH=20:1) to give 4.6 g of the title compound as a yellow solid. [M+H] found 297.

Preparation D: 7-methoxy-4-(oxan-2-yl)-4,5,10,12-tetraazatetracyclo[6.6.1.0²,⁶.0¹¹,¹⁵]pentadeca-1(15),2,5,8,11,13-hexaene

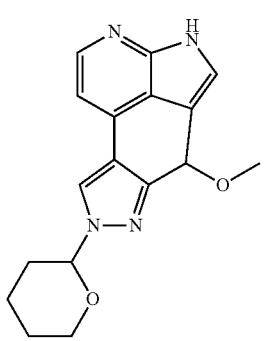

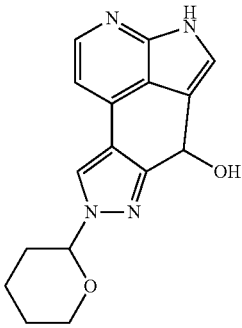

To a stirred solution of 1-(oxan-2-yl)-4-{1H-pyrrolo[2,3-b]pyridin-4-yl}-1H-pyrazole-3-carbaldehyde (1.88 g, 6.35 mmol) in MeOH (280 mL, a concentration of 0.023 mol/L), was added KOH (3.56 g, 27.68 mmol). The reaction mixture was stirred at room temperature for 42 hours. When TLC showed completion of reaction, the pH was adjusted to 7 by addition of HCl (4 M in MeOH).

The reaction mixture was concentrated and purified by chromatography column, eluting with ethyl acetate to give 370 mg of the title compound. By LC-MS the product contained ~30% of the corresponding alcohol as shown above. [M+H] found 311.

Preparation E: 4,5,10,12-tetraazatetracyclo[6.6.1.0²,⁶.0¹¹,¹⁵]pentadeca-1(15),2,5,8,11,13-hexaen-7-one

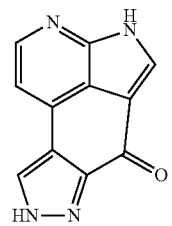 [SMILES: O=C1c2n[nH]cc2-c2ccnc3[nH]cc1c23]

To a stirred solution of 7-methoxy-4-(oxan-2-yl)-4,5,10,12-tetraazatetracyclo[6.6.1.0²,⁶.0¹¹,¹⁵]pentadeca-1(15),2,5,8,11,13-hexaene (1.0 g, containing ~30% of the alcohol by-product) in CH₃CN/H2O (30 mL, 2:1, V:V) was added cerium ammonium nitrate (4.6 g, 27.68 mmol). The reaction mixture was stirred at 0° C. for 3 hours. When TLC showed completion of the reaction, the pH was adjusted to 9-10 by adding saturated aqueous Na₂CO₃.

The reaction mixture was freeze-dried, and the residue purified by chromatography column, eluting with DCM:MeOH=20:1 to 5:1 to give 150 mg of the title compound. [M+H] found 211.

Example 1

3-cyclopentyl-3-{7-oxo-4,5,10,12-tetraazatetracyclo[6.6.1.0$^{2,6}$.0$^{11,15}$]pentadeca-1(15),2,5,8,11,13-hexaen-4-yl}propanenitrile

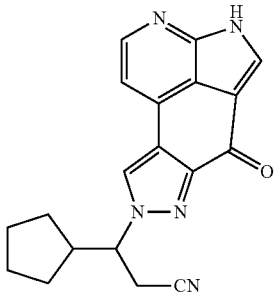 [SMILES: N#CCC(C1CCCC1)n1cc2c(n1)C(=O)c1c[nH]c3nccc-2c13]

Example 2

3-cyclopentyl-3-{7-oxo-4,5,10,12-tetraazatetracyclo[6.6.1.0$^{2,6}$.0$^{11,15}$]pentadeca-1(15),2(6),3,8,11,13-hexaen-5-yl}propanenitrile

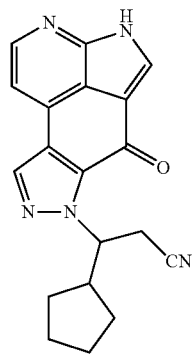 [SMILES: N#CCC(C1CCCC1)n1ncc2c1C(=O)c1c[nH]c3nccc-2c13]

To a stirred solution of 4,5,10,12-tetraazatetracyclo[6.6.1.0$^{2,6}$.0$^{11,15}$]pentadeca-1(15),2,5,8,11,13-hexaen-7-one (0.15 g, 0.71 mmol) in DMSO (2 mL) was added 3-cyclopentylacrylonitrile (0.09 g, 0.71 mmol), K$_2$CO$_3$ (15 mg, 0.15 equiv). The reaction mixture was stirred at room temperature for 3 days. When TLC showed completion of reaction, water was added. The mixture was extracted with ethyl acetate. The combined organic layer was washed with water, brine, dried over Na$_2$SO$_4$, and concentrated under vacuum.

The resulting residue was purified by prep-TLC, eluting with Hexanes: EtOAc (10:1) to give 80 mg of 3-cyclopentyl-3-{7-oxo-4,5,10,12-tetraazatetracyclo[6.6.1.0$^{2,6}$.0$^{11,15}$]pentadeca-1(15),2,5,8,11,13-hexaen-4-yl}propanenitrile, [M+H] found 332; and 40 mg of 3-cyclopentyl-3-{7-oxo-4,5,10,12-tetraazatetracyclo[6.6.1.0$^{2,6}$.0$^{11,15}$]pentadeca-1(15),2(6),3,8,11,13-hexaen-5-yl}propanenitrile, [M+H] found 332.

Example 3

(3S)-3-cyclopentyl-3-{7-oxo-4,5,10,12-tetraazatetracyclo[6.6.1.0$^{2,6}$.0$^{11,15}$]pentadeca-1(15),2,5,8,11,13-hexaen-4-yl}propanenitrile

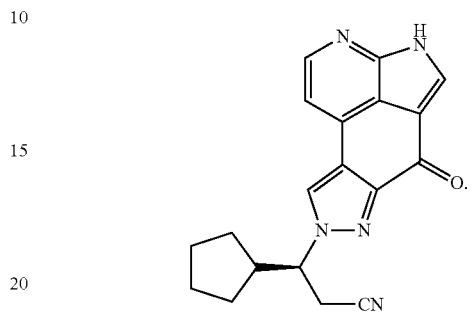

Example 4

(3R)-3-cyclopentyl-3-{7-oxo-4,5,10,12-tetraazatetracyclo[6.6.1.0$^{2,6}$.0$^{11,15}$]pentadeca-1(15),2,5,8,11,13-hexaen-4-yl}propanenitrile

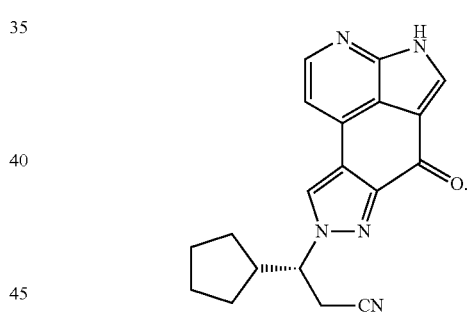

3-cyclopentyl-3-{7-oxo-4,5,10,12-tetraazatetracyclo[6.6.1.02,6.011,15] pentadeca-1(15),2,5,8,11,13-hexaen-4-yl}propanenitrile (Example 1) was separated by chiral SFC [ChiralPak AD-H, 250×30 mm I.D. column, flowrate=50 mL/min, mobile phase: A for liquid CO2 and B for IPA, gradient: B 40%] to give Example 3 ((3S)-3-cyclopentyl-3-{7-oxo-4,5,10,12-tetraazatetracyclo[6.6.1.02,6.011,15]pentadeca-1(15),2,5,8,11,13-hexaen-4-yl}propanenitrile, 50 mg) and Example 4 ((3R)-3-cyclopentyl-3-{7-oxo-4,5,10,12-tetraazatetracyclo[6.6.1.02,6.011,15]pentadeca-1(15),2,5,8,11,13-hexaen-4-yl}propanenitrile, 58 mg).

On the chiral analytical column [ChiralPak AD-H, 250×4 6 mm column, flowrate=2.4 mL/min, mobile phase: A for CO$_2$ and B for IPA (0.05% DEA), gradient: B 40%] Example 3 had a retention time of 7.56 min and Example 4 had a retention time of (10.09 min)

Example 5

(3S)-3-cyclopentyl-3-{7-oxo-4,5,10,12-tetraazatetracyclo[6.6.1.0²,⁶.0¹¹,¹⁵]pentadeca-1(15),2(6),3,8,11,13-hexaen-5-yl}propanenitrile

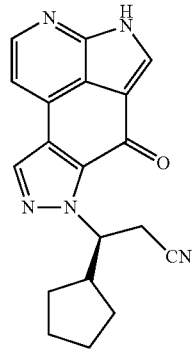

Example 6

(3R)-3-cyclopentyl-3-{7-oxo-4,5,10,12-tetraazatetracyclo[6.6.1.0²,⁶.0¹¹,¹⁵]pentadeca-1(15),2(6),3,8,11,13-hexaen-5-yl}propanenitrile

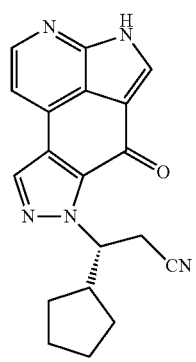

3-cyclopentyl-3-{7-oxo-4,5,10,12-tetraazatetracyclo[6.6.1.0²,⁶.0¹¹,¹⁵]pentadeca-1(15),2(6),3,8,11,13-hexaen-5-yl}propanenitrile (Example 2) was separated by chiral SFC [ChiralPak AS-H, 250×30 mm I D column, flowrate=50 mL/min, mobile phase: A for liquid $CO_2$ and B for EtOH, gradient: B 40%] to give Example 5 ((3S)-3-cyclopentyl-3-{7-oxo-4,5,10,12-tetraazatetracyclo[6.6.1.0²,⁶.0¹¹,¹⁵]pentadeca-1(15),2(6),3,8,11,13-hexaen-5-yl}propanenitrile, 12 mg) and Example 6 ((3R)-3-cyclopentyl-3-{7-oxo-4,5,10,12-tetraazatetracyclo[6.6.1.0²,⁶.0¹¹,¹⁵]pentadeca-1(15),2(6),3,8,11,13-hexaen-5-yl}propanenitrile, 34 mg).

On the chiral analytical column [ChiralPak AS-H, 250×4 6 mm column, flowrate=2.4 mL/min, mobile phase: A for $CO_2$ and B for MeOH (0.05% DEA), gradient: B 5-40%] Example 5 had a retention time of 7.34 min and Example 6 had a retention time of (9.14 min)

Example 7

3-cyclopentyl-3-{7-oxo-4,5,10,12-tetraazatetracyclo[6.6.1.0²,⁶.0¹¹,¹⁵]pentadeca-1(15),2,5,8,11,13-hexaen-4-yl}propanenitrile

Example 8

3-cyclopentyl-3-{4,5,10,12-tetraazatetracyclo[6.6.1.0²,⁶.0¹¹,¹⁵]pentadeca-1(15),2(6),3,8,11,13-hexaen-5-yl}propanenitrile

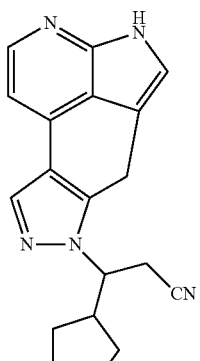

To a solution of 7-methoxy-4-(oxan-2-yl)-4,5,10,12-tetraazatetracyclo[6.6.1.0²,⁶.0¹¹,¹⁵]pentadeca-1(15),2,5,8,11,13-hexaene (1.0 g, 3.22 mmol) in 40 mL methanol at −10° C. was added 5 mL saturated hydrochloric acid methanol solution. The resulting mixture was stirred at 0° C. for 1.0 hour, and then poured into saturated sodium carbonate solution. The resulting suspension was filtered. The filter cake was washed with 10 mL water. The cake was dried at 70° C. to give Compound 7a (0.58 g, 80% yield) as a pale solid. [M+H] found 227.

To a sealed tube was added Compound 7a (1.0 g, 4.42 mmol), hydrochloric acid solution (18 mL, 5.0 M, 90.0 mmol). The resulting mixture was stirred at 100° C. for 3.5 hours, and then cooled to room temperature and poured into saturated sodium carbonate solution. The resulting suspension was filtered. The filter cake was washed with 10 mL water. The cake was dried at 70° C. to give Compound 7b (0.75 g, 80% yield) as an off-white solid. [M+H] found 212.9.

Trifluoroacetic acid (10 mL) and triethylsilane (5 mL) were added to a solution of Compound 7b (500 mg, 2.36 mmol) in 20 mL of dichloromethane. This mixture was magnetically stirred and heated under reflux for 2 hours. Then the solution was evaporated to remove the solvent at below 50° C. To the residue was added 10 mL saturated sodium bicarbonate and stirred at r.t for 0.5 h. The resulting suspension was filtered. The filter cake was washed with 10 mL water. The cake was purified by flash chromatography (5% Methanol/DCM) to give 286 mg of Compound 7c (Yield: 92%) as an off-white solid. [M+H] found 196.9.

To a stirred solution of Compound 7c (0.21 g, 1.0 mmol) in DMSO (8 mL) was added 3-cyclopentylprop-2-enenitrile (0.24 g, 2.0 mmol) and DBU (15 mg, 0.1 mmol). The reaction mixture was stirred at room temperature for 48 hours. 10 mL of water was added. The mixture was extracted with ethyl acetate (6×100 mL), and the combined organic extracts were washed with brine, dried by Na₂SO₄, filtered, and concentrated under vacuum at below 50° C. The crude product was purified by flash chromatography (3% Methanol/DCM) to give 33 mg of Compound 7 (Yield: 10%) and 14 mg of Compound 8 (Yield: 4%) as light yellow solids. [M+H] found 318.0.

Example 9

1-(3-methyl-2-{7-oxo-4,5,10,12-tetraazatetracyclo[6.6.1.0²,⁶.0¹¹,¹⁵]pentadeca-1(15),2,5,8,11,13-hexaen-4-yl}butanoyl)azetidine-3-carbonitrile Example 10

1-(3-methyl-2-{7-oxo-4,5,10,12-tetraazatetracyclo[6.6.1.0²,⁶.0¹¹,¹⁵]pentadeca-1(15),2(6),3,8,11,13-hexaen-5-yl}butanoyl)azetidine-3-carbonitrile

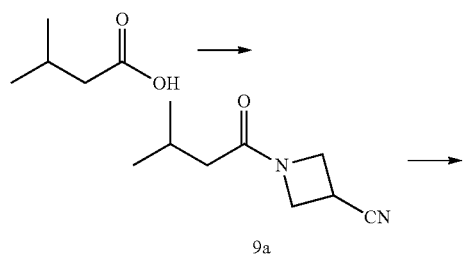

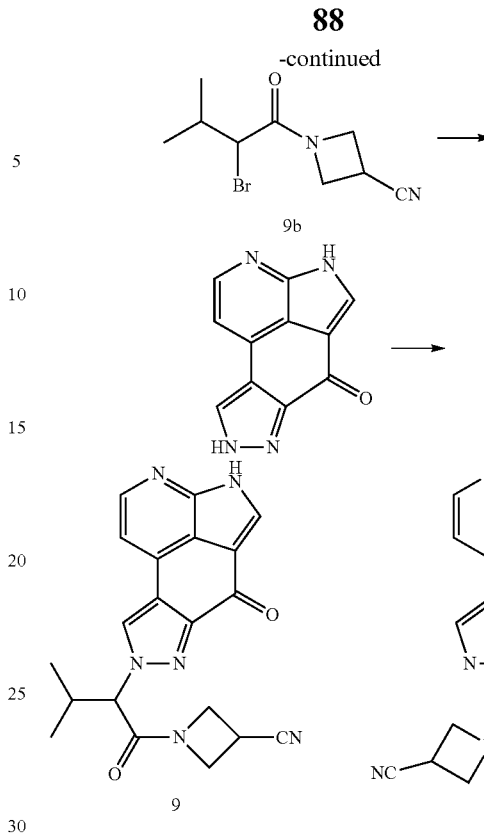

To a stirred solution of isovaleric acid (0.90 g, 8.85 mmol) in DCM (20 mL) was added 0.1 mL of N,N-Dimethylformamide. The solution was cooled to 0° C., followed by the addition of oxalyl chloride (1.45 g, 11.5 mmol). The reaction mixture was warmed to room temperature and stirred for 4.0 h. Then the solution was evaporated to remove the solvent at below 50° C. The residue and azetidine-3-carbonitrile hydrochloride (0.94 g, 7.96 mmol) were dissolved in 20 mL DCM. The solution was cooled to −20° C., followed by the addition of DIPEA (3.83 mL, 26.55 mmol). The reaction mixture was warmed to room temperature and stirred overnight. The resultant was quenched by addition of saturated aqueous NaHCO3. The mixture was extracted with DCM (3×100 mL), and the combined extracts were washed with brine, dried by Na₂SO₄ and filtered, concentrated under vacuum at below 40° C. The crude product was purified by flash chromatography (20% Petroleum ether/ethyl acetate) to give 833 mg of Compound 9a (Yield: 63%) as a light yellow oil. [M+H] found 167.

To a solution of LiHMDS (1.0 M in THF, 8.91 mL, 8.91 mmol) in 40 mL of THF at −78° C. was added trimethylsilyl chloride (1.2 mL, 8.91 mmol) dropwise via syringe pump. Compound 9a (1.23 g, 7.42 mmol) in 5 mL of THF was then added to the mixture dropwise via syringe pump. The mixture was stirred at −78° C. for 1 hours then NBS (1.58 g, 8.91 mmol) in 5 mL of THF was added dropwise via syringe pump. The reaction mixture was allowed to warm slowly to room temperature and was stirred for 3 h. The resultant was quenched by addition of saturated aqueous NH₄Cl. The mixture was extracted with ethyl acetate (3×100 mL), and the combined extracts were washed with brine, dried by Na₂SO₄ and filtered, concentrated under vacuum at below 40° C. The crude product was purified by flash chromatography (10% Petroleum ether/ethyl acetate) to give 363 mg of Compound 9b (Yield: 20%) as light yellow oil. [M+H] found 246.9.

To a stirred solution of compound 4,5,10,12-tetraazatetracyclo[6.6.1.0$^{2,6}$.0$^{11,15}$]pentadeca-1(15),2,5,8,11,13-hexaen-7-one (0.47 mmol, from PREPARATION E) in DMSO (5 mL) was added Compound 9b (175 mg, 0.71 mmol) and DBU (11 mg, 0.07 mmol). The reaction mixture was stirred at room temperature for 48 hours. 10 mL of water was added. The mixture was extracted with ethyl acetate (6×60 mL), and the combined extracts were washed with brine, dried by Na$_2$SO$_4$ and filtered, concentrated under vacuum at below 50° C. The crude product was purified by flash chromatography (3% Methanol/DCM) to give 17 mg of Compound 9 (Yield: 10%) and 6.8 mg of Compound 10 (Yield: 4%) as light yellow solids. [M+H] found 375.

Example 11

JAK Activity

JAK activity was determined using Invitrogen's SelectScreen® Biochemical Kinase Profiling Service using the Z'-LYTE Screening Protocol and Assay Conditions (ATP concentration at Km).

The exemplified compounds inhibited human JAK in the assay of Example A with an IC$_{50}$ of: +++ less than about 10 nM, ++ between 10 and 100 nM, and + greater than 100 nM as shown in Table 1.

TABLE 1

| Example No. | JAK1 IC$_{50}$ (nM) | JAK2 IC$_{50}$ (nM) | JAK3 IC$_{50}$ (nM) |
|---|---|---|---|
| 1 | ++ | +++ | + |
| 2 | + | ++ | + |
| 3 | ND | ND | ND |
| 4 | ++ | +++ | + |
| 5 | ND | ND | ND |
| 6 | ND | ND | ND |

What is claimed is:

1. A compound of Formula I, Formula II, or Formula III:

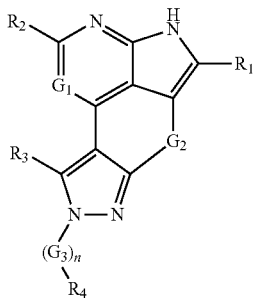

I

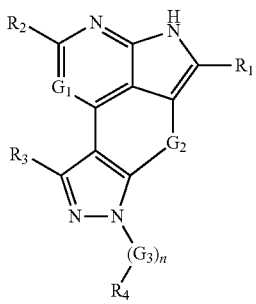

II

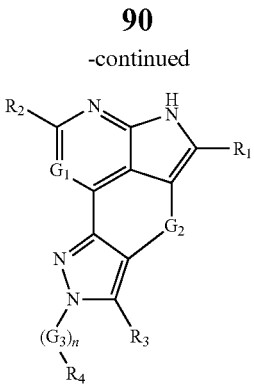

III or pharmaceutically acceptable salt, solvate, prodrug, isomer or tautomer thereof wherein:

G$_1$ is N or CR$_5$;
G$_2$ is —NR$_8$—, C=O, —C(O)—NR$_8$—, —NR$_8$C(O)—, or —CR$_6$R$_7$;
G$_3$ is a bond, hydrogen, —C(O)—, —C(O)—NH—, —C(O)N—R$_8$, —SO$_2$—, —S(O)—, optionally substituted C$_{1-6}$ alkyl, optionally substituted C$_{3-8}$ cycloalkyl, optionally substituted C$_{3-6}$ heterocycloalkyl, optionally substituted C$_{4-14}$ aryl, or optionally substituted C$_{1-10}$ heteroaryl;
n is 0, 1, 2, 3, or 4;
R$_1$ is hydrogen, optionally substituted C$_{1-4}$ alkyl, optionally substituted C$_{3-8}$ cycloalkyl, optionally substituted C$_{3-8}$ heterocycloalkyl, or halogen;
R$_2$ is hydrogen, optionally substituted C$_{1-4}$ alkyl, optionally substituted C$_{1-4}$ alkoxy, optionally substituted C$_{3-8}$ cycloalkyl, optionally substituted C$_{3-8}$ heterocycloalkyl, halogen, hydroxy, or amino;
R$_3$, R$_{3'}$, and R$_5$ are each independently hydrogen, optionally substituted C$_{1-6}$ alkyl, optionally substituted C$_{1-4}$ alkoxy, C$_{1-9}$ amide, C$_{1-5}$ oxycarbonyl, cyano, optionally substituted C$_{3-8}$ cycloalkyl, optionally substituted C$_{4-14}$ aryl, optionally substituted C$_{1-10}$ heteroaryl, or halogen;
R$_8$ is -(G$_3$)n-R$_4$, optionally substituted C$_{1-4}$ alkyl, optionally substituted C$_{3-8}$ cycloalkyl, optionally substituted C$_{3-6}$ heterocycloalkyl, optionally substituted C$_{4-14}$ aryl, or optionally substituted C$_{1-10}$ heteroaryl; R$_4$ is optionally substituted C$_{1-4}$ alkyl, optionally substituted C$_{3-8}$ cycloalkyl, optionally substituted C$_{3-6}$ heterocycloalkyl, optionally substituted C$_{4-14}$ aryl, or optionally substituted C$_{1-10}$ heteroaryl; wherein R$_4$ and R$_8$ can be joined to form a ring; and
R$_6$ and R$_7$ are each independently —OR$_3$, —NHR$_3$, —NR$_3$R$_{3'}$, hydrogen, halo, optionally substituted C$_{1-4}$ alkyl, optionally substituted C$_{3-8}$ cycloalkyl, or optionally substituted C$_{3-8}$ heterocycloalkyl; wherein R$_6$ and R$_7$ can be joined to form a ring.

2. The compound of claim 1 consisting of the following structure:

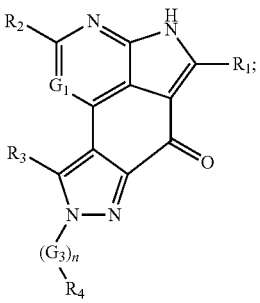

Ia or pharmaceutically acceptable salt, solvate, prodrug, isomer or tautomer thereof.

3. The compound of claim 1 consisting of the following structure:

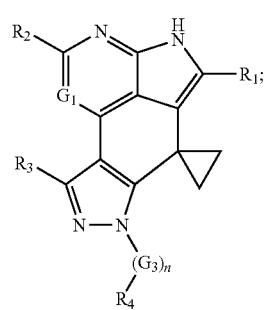
IId
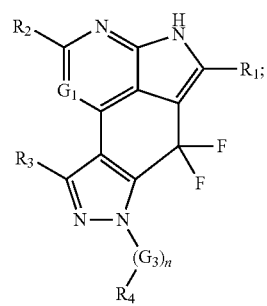
IIe
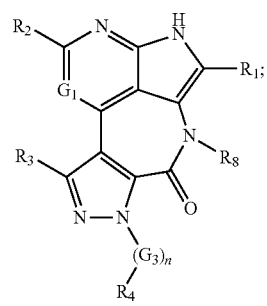
IIf
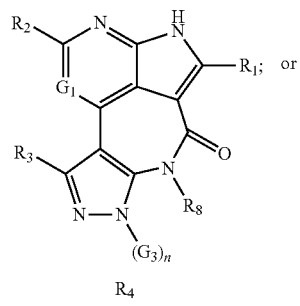
IIg; or
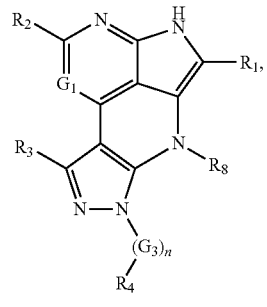
IIh
or pharmaceutically acceptable salt, solvate, prodrug, isomer or tautomer thereof.
4. The compound of claim 1 consisting of the following structure:
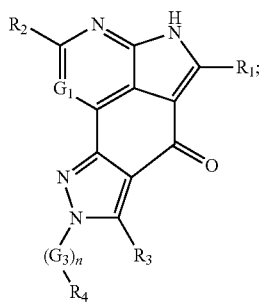
IIIa
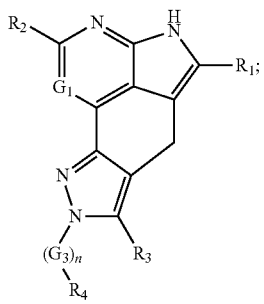
IIIb
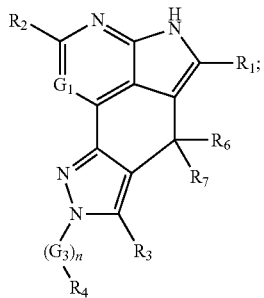
IIIc
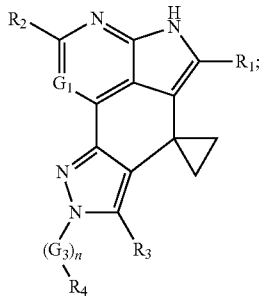
IIId
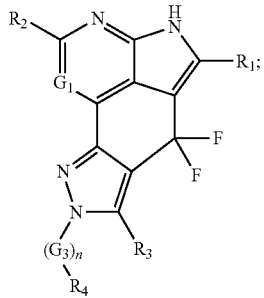
IIIe

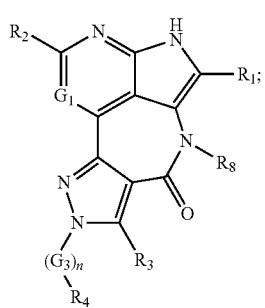

IIIf

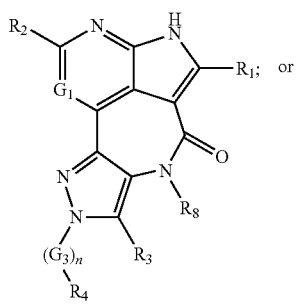

IIIg

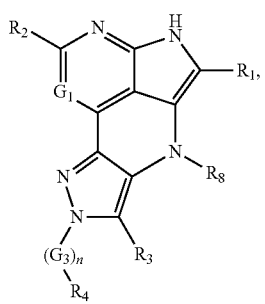

IIIh or pharmaceutically acceptable salt, solvate, prodrug, isomer or tautomer thereof.

5. A compound having Formula IV or V:

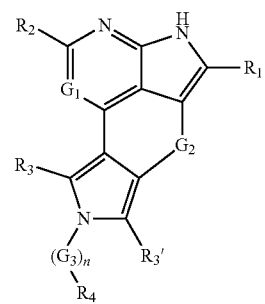

IV

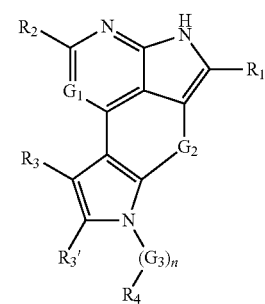

V or pharmaceutically acceptable salt, solvate, prodrug, isomer or tautomer thereof wherein:

$G_1$ is N or $CR_5$;

$G_2$ is $-NR_8-$, C=O, $-C(O)-NR_8-$, $-NR_8C(O)-$, or $-CR_6R_7$;

$G_3$ is a bond, hydrogen, $-C(O)-$, $-C(O)-NH-$, $-C(O)N-R_8$, $-SO_2-$, $-S(O)-$, optionally substituted $C_{1-6}$ alkyl, optionally substituted $C_{3-8}$ cycloalkyl, optionally substituted $C_{3-6}$ heterocycloalkyl, optionally substituted $C_{4-14}$ aryl, or optionally substituted $C_{1-10}$ heteroaryl;

n is 0, 1, 2, 3, or 4;

$R_1$ is hydrogen, optionally substituted $C_{1-4}$ alkyl, optionally substituted $C_{3-8}$ cycloalkyl, optionally substituted $C_{3-8}$ heterocycloalkyl, or halogen;

$R_2$ is hydrogen, optionally substituted $C_{1-4}$ alkyl, optionally substituted $C_{1-4}$ alkoxy, optionally substituted $C_{3-8}$ cycloalkyl, optionally substituted $C_{3-8}$ heterocycloalkyl, halogen, hydroxy, or amino;

$R_3$ and $R_{3'}$ are each independently hydrogen, optionally substituted $C_{1-6}$ alkyl, optionally substituted $C_{1-4}$ alkoxy, $C_{1-9}$ amide, $C_{1-5}$ oxycarbonyl, cyano, optionally substituted $C_{3-8}$ cycloalkyl, optionally substituted $C_{4-14}$ aryl, optionally substituted $C_{1-10}$ heteroaryl, or halogen;

$R_5$ is hydrogen, optionally substituted $C_{1-6}$ alkyl, optionally substituted $C_{1-4}$ alkoxy, $C_{1-9}$ amide, $C_{1-5}$ oxycarbonyl, cyano, optionally substituted $C_{3-8}$ cycloalkyl, optionally substituted $C_{4-14}$ aryl, optionally substituted $C_{1-10}$ heteroaryl, or halogen;

$R_8$ is $-(G_3)n-R_4$, optionally substituted $C_{1-4}$ alkyl, optionally substituted $C_{3-8}$ cycloalkyl, optionally substituted $C_{3-6}$ heterocycloalkyl, optionally substituted $C_{4-14}$ aryl, or optionally substituted $C_{1-10}$ heteroaryl; $R_4$ is optionally substituted $C_{1-4}$ alkyl, optionally substituted $C_{3-8}$ cycloalkyl, optionally substituted $C_{3-6}$ heterocycloalkyl, optionally substituted $C_{4-14}$ aryl, or optionally substituted $C_{1-10}$ heteroaryl; wherein $R_4$ and $R_8$ can be joined to form a ring; and $R_6$ and $R_7$ are each independently $-OR_3$, $-NHR_3$, $-NR_3R_{3'}$, hydrogen, halo, optionally substituted $C_{1-4}$ alkyl, optionally substituted $C_{3-8}$ cycloalkyl, or optionally substituted $C_{3-8}$ heterocycloalkyl; wherein $R_6$ and $R_7$ can be joined to form a ring.

6. A compound having Formula VI, Formula VII or Formula VIII having the following formula:

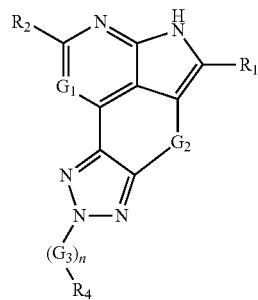

VI

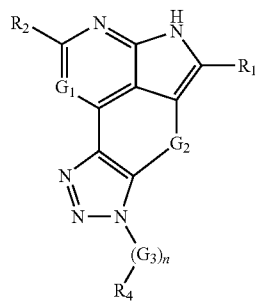

VII

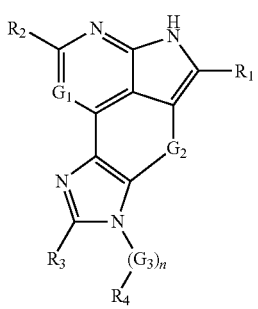

VIII or pharmaceutically acceptable salt, solvate, prodrug, isomer or tautomer thereof wherein:

$G_1$ is N or $CR_5$;

$G_2$ is $-NR_8-$, $C=O$, $-C(O)-NR_8-$, $-NR_8C(O)-$, or $-CR_6R_7$;

$G_3$ is a bond, hydrogen, $-C(O)-$, $-C(O)-NH-$, $-C(O)N-R_8$, $-SO_2-$, $-S(O)-$, optionally substituted $C_{1-6}$ alkyl, optionally substituted $C_{3-8}$ cycloalkyl, optionally substituted $C_{3-6}$ heterocycloalkyl, optionally substituted $C_{4-14}$ aryl, or optionally substituted $C_{1-10}$ heteroaryl;

n is 0, 1, 2, 3, or 4;

$R_1$ is hydrogen, optionally substituted $C_{1-4}$ alkyl, optionally substituted $C_{3-8}$ cycloalkyl, optionally substituted $C_{3-8}$ heterocycloalkyl, or halogen;

$R_2$ is hydrogen, optionally substituted $C_{1-4}$ alkyl, optionally substituted $C_{1-4}$ alkoxy, optionally substituted $C_{3-8}$ cycloalkyl, optionally substituted $C_{3-8}$ heterocycloalkyl, halogen, hydroxy, or amino;

$R_5$ is hydrogen, optionally substituted $C_{1-6}$ alkyl, optionally substituted $C_{1-4}$ alkoxy, $C_{1-9}$ amide, $C_{1-5}$ oxycarbonyl, cyano, optionally substituted $C_{3-8}$ cycloalkyl, optionally substituted $C_{4-14}$ aryl, optionally substituted $C_{1-10}$ heteroaryl, or halogen;

$R_8$ is $-(G_3)n-R_4$, optionally substituted $C_{1-4}$ alkyl, optionally substituted $C_{3-8}$ cycloalkyl, optionally substituted $C_{3-6}$ heterocycloalkyl, optionally substituted $C_{4-14}$ aryl, or optionally substituted $C_{1-10}$ heteroaryl; $R_4$ is optionally substituted $C_{1-4}$ alkyl, optionally substituted $C_{3-8}$ cycloalkyl, optionally substituted $C_{3-6}$ heterocycloalkyl, optionally substituted $C_{4-14}$ aryl, or optionally substituted $C_{1-10}$ heteroaryl; wherein $R_4$ and $R_8$ can be joined to form a ring; and $R_6$ and $R_7$ are each independently $-OR_3$, $-NHR_3$, $-NR_3R_{3'}$, hydrogen, halo, optionally substituted $C_{1-4}$ alkyl, optionally substituted $C_{3-8}$ cycloalkyl, or optionally substituted $C_{3-8}$ heterocycloalkyl; wherein $R_6$ and $R_7$ can be joined to form a ring.

7. The compound of claim 1 having the following formula:

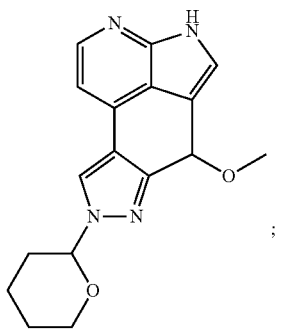

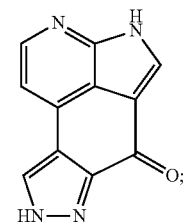

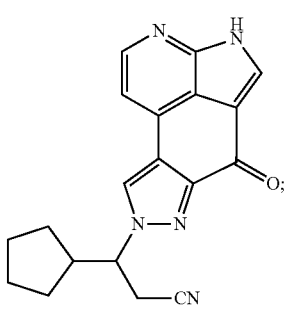

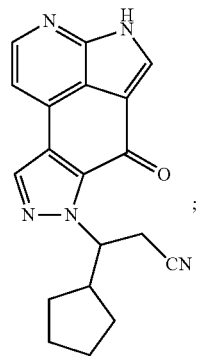

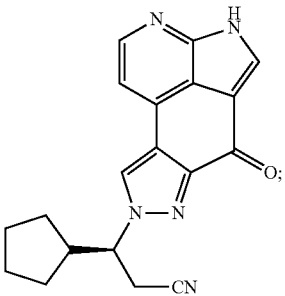 [SMILES: N#CC[C@@H](C1CCCC1)n1cc2c(n1)C(=O)c1c[nH]c3nccc-2c13]

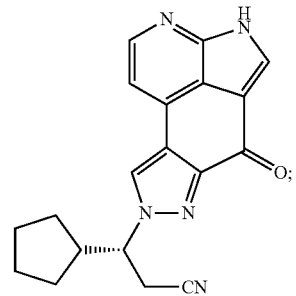 [SMILES: N#CC[C@H](C1CCCC1)n1cc2c(n1)C(=O)c1c[nH]c3nccc-2c13]

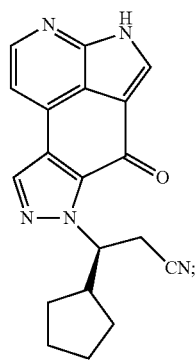

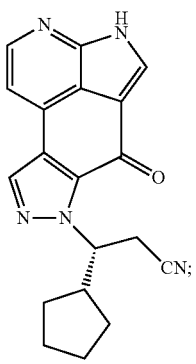

-continued
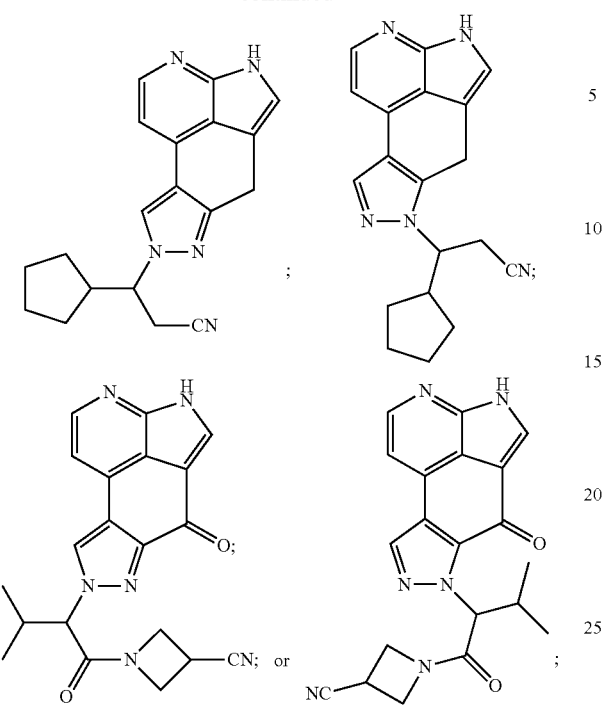
or a pharmaceutically acceptable salt, solvate, prodrug, isomer or tautomer thereof.
* * * * *